C(12) United States Patent
Taft et al.

(10) Patent No.: US 8,956,602 B2
(45) Date of Patent: Feb. 17, 2015

(54) DELIVERY OF DRUGS

(75) Inventors: David Taft, Atherton, CA (US); Steven Bitler, Menlo Park, CA (US); Qiang Zheng, Palo Alto, CA (US); Adam Bell, San Francisco, CA (US); Stelios Tzannis, Newark, CA (US)

(73) Assignee: Landec, Inc., Menlo Park, CA (US)

( * ) Notice: Subject to any disclaimer, the term of this patent is extended or adjusted under 35 U.S.C. 154(b) by 1512 days.

(21) Appl. No.: 11/999,415

(22) Filed: Dec. 4, 2007

(65) Prior Publication Data

US 2008/0269105 A1    Oct. 30, 2008

Related U.S. Application Data

(60) Provisional application No. 60/873,234, filed on Dec. 5, 2006.

(51) Int. Cl.
A61K 31/74 (2006.01)
A61K 9/00 (2006.01)
A61K 9/14 (2006.01)

(52) U.S. Cl.
CPC ............ *A61K 9/0024* (2013.01); *A61K 9/0019* (2013.01); *A61K 9/146* (2013.01)
USPC ..................................................... 424/78.17

(58) Field of Classification Search
None
See application file for complete search history.

(56) References Cited

U.S. PATENT DOCUMENTS

| 3,608,549 | A |   | 9/1971  | Merrill           |         |
|-----------|---|---|---------|-------------------|---------|
| 4,558,690 | A |   | 12/1985 | Joyce             |         |
| 4,808,412 | A |   | 2/1989  | Smith             |         |
| 4,830,855 | A |   | 5/1989  | Stewart           |         |
| 5,120,349 | A | * | 6/1992  | Stewart et al.    | 504/234 |
| 5,129,180 | A |   | 7/1992  | Stewart           |         |
| 5,143,730 | A |   | 9/1992  | Fues et al.       |         |
| 5,156,911 | A |   | 10/1992 | Stewart           |         |
| 5,213,808 | A |   | 5/1993  | Bar-Shalom et al. |         |
| 5,308,623 | A |   | 5/1994  | Fues et al.       |         |
| 5,384,333 | A |   | 1/1995  | Davis et al.      |         |
| 5,387,450 | A |   | 2/1995  | Stewart           |         |
| 5,412,035 | A | * | 5/1995  | Schmitt et al.    | 525/93  |
| 5,429,654 | A |   | 7/1995  | Swarup            |         |
| 5,469,867 | A |   | 11/1995 | Schmitt           |         |
| 5,589,192 | A | * | 12/1996 | Okabe et al.      | 424/486 |
| 5,644,049 | A | * | 7/1997  | Giusti et al.     | 536/53  |
| 5,662,711 | A |   | 9/1997  | Douglas           |         |
| 5,665,822 | A | * | 9/1997  | Bitler et al.     | 525/92 C|
| 5,687,718 | A |   | 11/1997 | Fischer et al.    |         |
| 5,725,881 | A |   | 3/1998  | Buchholz et al.   |         |

(Continued)

FOREIGN PATENT DOCUMENTS

AR    P 070104879    5/2009
EP    0064379 A1    11/1982

(Continued)

OTHER PUBLICATIONS

Focosi, "Hyaluronate and risperidone for hemorrhagic cystitis", 2006, Bone Marrow Transplantation, 39, pp. 57.*

(Continued)

*Primary Examiner* — Paul Dickinson
(74) *Attorney, Agent, or Firm* — James S. McDonald; Timothy Richardson

(57) ABSTRACT

Formulations of drugs and crystalline side chain polymers to provide controlled and/or sustained release drug formulations.

58 Claims, 29 Drawing Sheets

(56) References Cited

U.S. PATENT DOCUMENTS

| | | |
|---|---|---|
| 5,783,302 A | 7/1998 | Bitler |
| 5,792,477 A * | 8/1998 | Rickey et al. ............... 424/501 |
| 5,826,584 A | 10/1998 | Schmitt |
| 5,852,117 A | 12/1998 | Schoenberg et al. |
| 5,895,404 A | 4/1999 | Ruiz |
| 5,945,457 A | 8/1999 | Plate et al. |
| 5,985,850 A * | 11/1999 | Falk et al. ............... 514/54 |
| 6,001,395 A | 12/1999 | Coombes et al. |
| 6,004,549 A | 12/1999 | Reichert et al. |
| 6,199,318 B1 | 3/2001 | Stewart |
| 6,214,901 B1 | 4/2001 | Chudzik |
| 6,224,793 B1 | 5/2001 | Hoffman |
| 6,255,367 B1 | 7/2001 | Bitler |
| 6,297,337 B1 | 10/2001 | Marchant et al. |
| 6,319,521 B1 | 11/2001 | Randolph |
| 6,344,035 B1 | 2/2002 | Cudzik |
| 6,352,667 B1 | 3/2002 | English |
| 6,423,345 B2 | 7/2002 | Berstein et al. |
| 6,469,133 B2 | 10/2002 | Baker et al. |
| 6,497,867 B2 * | 12/2002 | Meffert et al. ............ 424/78.03 |
| 6,524,274 B1 | 2/2003 | Rosenthal |
| 6,528,080 B2 | 3/2003 | Dunn et al. |
| 6,540,984 B2 | 4/2003 | Stewart |
| 6,569,128 B1 | 5/2003 | Christensen et al. |
| 6,576,254 B1 | 6/2003 | Uchegbu |
| 6,653,395 B1 | 11/2003 | Bergstrom et al. |
| 6,656,385 B2 | 12/2003 | Lynch |
| 6,657,042 B2 | 12/2003 | Rafler et al. |
| 6,699,952 B2 | 3/2004 | Chaikof |
| 6,730,322 B1 | 5/2004 | Berstein et al. |
| 6,780,930 B2 | 8/2004 | Lewis |
| 6,831,116 B2 | 12/2004 | Bitler |
| 6,858,634 B2 | 2/2005 | Asrar et al. |
| 6,866,860 B2 | 3/2005 | Nathan |
| 6,887,960 B2 | 5/2005 | Parker et al. |
| 6,890,583 B2 | 5/2005 | Chudzik |
| 6,951,642 B2 | 10/2005 | Scholz et al. |
| 6,964,778 B1 | 11/2005 | Hui |
| 6,967,234 B2 | 11/2005 | Nathan |
| 6,989,417 B2 | 1/2006 | Bitler et al. |
| 7,008,667 B2 | 3/2006 | Chudnik |
| 7,030,084 B2 | 4/2006 | Ekwuribe et al. |
| 7,083,572 B2 | 8/2006 | Unger et al. |
| 7,220,430 B2 | 5/2007 | Ishibashi et al. |
| 2002/0037318 A1 | 3/2002 | Meffert |
| 2002/0106406 A1 | 8/2002 | McHugh et al. |
| 2002/0114827 A1 | 8/2002 | Zhang |
| 2002/0161437 A1 | 10/2002 | Zhou et al. |
| 2003/0049308 A1 * | 3/2003 | Theobald et al. ............ 424/449 |
| 2003/0082217 A1 | 5/2003 | Afriat |
| 2003/0185872 A1 * | 10/2003 | Kochinke .................. 424/426 |
| 2003/0224974 A1 | 12/2003 | Bolotin |
| 2004/0052746 A1 | 3/2004 | Tamareselvy |
| 2004/0117006 A1 | 6/2004 | Lewis et al. |
| 2004/0208844 A1 | 10/2004 | Ignatious |
| 2004/0236013 A1 | 11/2004 | Lewis |
| 2004/0254419 A1 | 12/2004 | Wang et al. |
| 2005/0019923 A1 | 1/2005 | Uchegbu et al. |
| 2005/0169977 A1 | 8/2005 | Kanios et al. |
| 2005/0197251 A1 | 9/2005 | Ding et al. |
| 2005/0249697 A1 | 11/2005 | Uhrich et al. |
| 2005/0249799 A1 | 11/2005 | Jacob |
| 2006/0018948 A1 | 1/2006 | Guire |
| 2006/0024361 A1 | 2/2006 | Odidi |
| 2006/0034891 A1 | 2/2006 | Lawin et al. |
| 2006/0148982 A1 | 7/2006 | Uchegbu et al. |
| 2006/0167116 A1 | 7/2006 | Uchegbu et al. |
| 2006/0286064 A1 | 12/2006 | Turnell et al. |
| 2006/0292222 A1 | 12/2006 | Jonasee |
| 2007/0016284 A1 | 1/2007 | Pacetti |
| 2007/0134310 A1 | 6/2007 | Nedberge et al. |
| 2007/0142461 A1 | 6/2007 | Baker et al. |
| 2007/0259584 A1 | 11/2007 | Whitehouse |
| 2009/0124996 A1 | 5/2009 | Krumme |
| 2009/0177158 A1 | 7/2009 | Krumme |
| 2009/0198183 A1 | 8/2009 | Krumme |
| 2009/0240200 A1 | 9/2009 | Krumme |

FOREIGN PATENT DOCUMENTS

| | | |
|---|---|---|
| EP | 0568345 A1 | 11/1993 |
| EP | 0778304 | 6/1997 |
| EP | 1348451 A1 | 10/2003 |
| EP | 1430916 A1 | 6/2004 |
| EP | 1629835 A1 | 3/2006 |
| GB | 2160100 A | 12/1985 |
| GB | 2161819 A | 1/1986 |
| JP | 62042918 A | 2/1987 |
| JP | 3123730 A | 5/1991 |
| RU | 2092161 | 10/1997 |
| TW | 096141574 | 5/2008 |
| WO | WO 91/04015 A1 | 4/1991 |
| WO | WO 92/13901 | 8/1992 |
| WO | WO 94/07940 A1 | 4/1994 |
| WO | WO 96/18417 A1 | 6/1996 |
| WO | WO 99/36058 | 7/1999 |
| WO | WO 99/47543 A2 | 9/1999 |
| WO | WO 99/56731 | 11/1999 |
| WO | WO 01/54671 A1 | 8/2001 |
| WO | WO 01/87276 | 11/2001 |
| WO | WO 02/45685 A2 | 6/2002 |
| WO | WO 03/022323 A1 | 3/2003 |
| WO | WO 03/028653 | 4/2003 |
| WO | WO 03/033027 | 4/2003 |
| WO | WO 2004/024779 | 3/2004 |
| WO | WO 2004/026912 | 4/2004 |
| WO | WO 2004/052339 | 6/2004 |
| WO | WO 2005/051358 A1 | 6/2005 |
| WO | WO 2005/084639 | 9/2005 |
| WO | WO 2006/039152 | 4/2006 |
| WO | WO 2006/128471 A2 | 12/2006 |
| WO | PCT 07/023226 | 6/2008 |
| WO | WO 2008/066657 A2 | 6/2008 |

OTHER PUBLICATIONS

Beckmann, H., et al., "High Dose Diazepam in Schizophrenia", 1980, Psychopharmacology, 71, pp. 79-82.*

U.S. Appl. No. 60/856,430, filed May 3, 2008, Schmitt.

U.S. Appl. No. 60/857,546, filed May 8, 2008, Schmitt.

U.S. Appl. No. 60/857,755, filed May 8, 2008, Krumme.

U.S. Appl. No. 60/964,066, filed Feb. 8, 2009, Krumme.

U.S. Appl. No. 60/993,541, filed Mar. 12, 2009, Krumme.

U.S. Appl. No. 61/016,223, filed Jun. 21, 2009, Krumme.

Lee, J. et al, "Thermosenstive Permeation From Side-Chain Crystalline Ionomers", Journal of Polymer Science: Part B: Polymer Physics, vol. 38, pp. 823-830; 2000.

Mohr, J.M., et al., "Drug Delivery with Side Chain Crystallizable Polymer Blends", 1991; Proceedings of the 18th International Symposium on Controlled Release of Bioactive Materials, pp. 409-410; Controlled Release Society, U.S.A.

Mohr, J.M., et al, "Pulsatile Transdermal Drug Delivery", 1992; Proceedings of the 19th International Symposium on Controlled Release of Bioactive Materials, pp. 377-378; Controlled Release Society, U.S.A.

Brannon-Peppas, L., "Polymers in Controlled Drug Delivery", Medical Plastics and Biomaterials, p. 34, Nov. 1997.

Birnbaum, D., et al., "Microparticle Drug Delivery Systems" Drug Delivery Systems in Cancer Therapy, Chapter 6, pp. 117-135; Sep. 2003.

Du, J., et al., "pH Sensitive Vesicles Based on a Biocompatible Zwitterionic Diblock Copolymer", Journal of American Chemistry Society, vol. 127, #51, pp. 17982-17983; 2005.

Kaneko, T.; Miyazaki, T.; Yamaoka, K.; Katayama, Y.; Matsuda, A.; Gong, J.; and Osada, Y.; "Shape-Memory Gels with Multi-Stimuli Responses"; Proceedings of SPIE, vol. 3669, pp. 199-208, Smart Structures and Materials; May 1999: Electroactive Polymer Actuators and Devices.

(56) References Cited

OTHER PUBLICATIONS

Wei, J-S.; Zeng, H-B.; Liu, S-Q.; Wang, X-G.; Tay, E.H.; and Yang, Y-Y.; Temperature and pH Sensitive Core-Shell Nanoparticles Self-Assembled From Poly(N-Isopropylacrylamide-Co-Acrylic Acid-CO-Cholesteryl Acrylate) For Intracellular Delivery of Anticancer Drugs; Sep. 2005; Frontiers in Bioscience 10, pp. 3058-3067; Frontier in Bioscience, U.S.A.

Ng, C.C.; Cheng, Y-L.; Saville, B.A.; Thermoresponsive Polymer Membrane for the Local Delivery of Drugs; Summer 2001; Journal of Sexual and Reproductive Medicine, vol. 1 #1, pp. 21-27; Pulses Group Inc., Canada.

Luppi, B.; Cerchiara, T.; Bigucci, F.; Orienti, I.; and Zecchi, V.; pH-Sensitive Polymeric Physical-Mixture for Possible Site-Specific Delivery of Ibuprofen; Mar. 2003; European Journal of Pharmaceutics and Biopharmaceutics, 55, #2, pp. 199-202; Elsevier, Netherlands.

Bulmus, V.; Woodward, M.; Lin, L.; Murthy, N.; Stayton, P.; and Hoffman, A.; A New pH Responsive and Glutathione-Reactive, Endosomal Membrane Disruptive Polymeric Carrier for Intracellular Delivery of Biomolecular Drugs; Dec. 2003; Journal of Controlled Release, vol. 93, #2, pp. 105-120; Elsevier, Netherlands.

K.M. Scholsky and R.M. Fitch; Controlled Release of Pendant Bioactive Materials from Acrylic Polymer Colloids; 1986; Journal of Controlled Release, vol. 3, #1-4, pp. 87-102; Elsevier, Netherlands.

LaVan, D.A.; McGuire, T.; and Langer, R.; Small Scale Systems for In Vivo Drug Delivery; Oct. 2003; Nature Biotechnology, vol. 21, #10, pp. 1184-1191; Nature Publishing Group., U.K.

Schmidt, E.E.; Mohr, J.; and Stewart, R.F.; Side Chain Crystallizable Polymer Based Drug Delivery Phenomenon; 1991; in Proceedings of the 18th International Symposium on Controlled Release of Bioactive Materials, p. 134-135; Controlled Release Society, U.S.A.

Torchilin, V., "Structure and Design of Polymeric Surfactant-Based Drug Delivery Systems",Journal of Controlled Release, vol. 73, #2-3, pp. 137-172; Jun. 2001.

Boudreaux, C.J., et al., "Controlled Activity Polymers. XI Hydrolytic Release Studies of Hydrophilic Copolymers With Labile Esters of Model Allelopathic Phenols", Journal of Controlled Release, vol. 44, #2-3, pp. 185-194, Feb. 1997.

Loth, H., et al. "Methoxy-Polyethoxy Side-Chain Silastomers as Materials Controlling Drug Delivery By Diffusion Flux", Journal of Controlled Release, vol. 54, #3, pp. 273-282 Aug. 1998.

Yadav, S.K., et al., "Release Rates From Semi-Crystalline Polymer Microcapsules Formed By Interfacial Polycondensation", Journal of Membrane Science, vol. 125, #2, pp. 213-218; Mar. 1997.

Greene, L., "Side-Chain Crystallizable Polymers for Temperature-Activated Controlled Release", Polymeric Delivery Systems: Properties and Applications (ACS Symposium Series, No. 520), pp. 244-256, 1993.

Yu, L., et al., "A Subtle End-Group Effect on Macroscopic Physical Gelation of Triblock Copolymer Aqueous Solutions", Angew. Chem. Int. Ed. 2006, 45, 2232-2235.

Abayashinghe, N., et al., "Oligoethylene-End-Capped-Polylactides", Journal of Polymer Science: Part A: Polymer Chemistry, vol. 43, 5257-5266 (2005).

Mehvar, R., "Modulation of the Pharmacokinetics and Pharmacodynamics of Proteins by Polyethylene Glycol Conjugation", J. Pharm. Pharmaceut. Sci. 3(1):125-136, 2000.

Jiang, X., et al., ""Clickable" Polyglycolides: Tunable Synthons for Thermoresponsive, Degradable Polymers", Department of Chemistry, Michigan State University, East Lansing, MI, p. 1-34.

Baker, G., et al., "New Polylactides from Hydroxyacids Derived from Renewable Sources". Polymer Preprints 2007, 48(2), 826.

Maruyama, S., et al., "A Synthetic Polymer, Poly(2-methacryloyloxyethyl phosphorylcholine-*co-n*-stearyl methacrylate), Stimulates Insulin Release form RINm5F Insulinoma Cells", Biosci. Biotechnol. Biochem., 68 (10), 2197-2200, 2004.

Pollino, J., et al., "Non-Covalent Side-Chain Polymers: Design Principles, Functionalization Strategies and Perspectives", Chem. Soc. Rev., 2005, 34, 193-207.

Roberts, M., et al., "Molecule Engineering Including Advanced PEGylation: Understanding the Full Potential", The Drug Delivery Companies Report Spring/Summer 2003, PharmaVentures, Ltd, 2003.

Ivan, B., et al., "New Nanophase Separated Intelligent Amphiphilic Conetworks and Gels", Macromolecular Symposia, Jul. 2005 vol. 227 (1), pp. 265-274, Wiley-VCH GmbH & Co. KgaA, Weinheim.

Shang, S., et al., "Comb-Like Ionomeric Copolymer: Itaconic Anhydride-co-Stearyl Methacrylate", ACS Polymer Preprints, 2007, vol. 48(2), pp. 871-872.

Davaran, S., et al., "Release of 5-Aminosalicylic Acid from Acrylic Type Polymeric Prodrugs Designed for Colon Drug Delivery", 1999; Journal of Controlled Release, 58, #3, pp. 279-287.

Bendix, Dieter, "Chemical Synthesis of Polyactide and its Copolymers for Medical Applications" 1998, Polymer Degradation and Stability, vol. 59, pp. 129-135; Elsevier Science Limited.

Mehta, Nozer M., "Oral Delivery and Recombinant Production of Peptide Hormones. Part I: Making Oral Delivery Possible" Jun. 2004 Biopharm International pp. 1-6.

Mehta, Nozer M., "Oral Delivery and Recombinant Production of Peptide Hormones. Part II: Recombinant Production of Therapeutic Peptides" Jul. 2004 Biopharm International pp. 7-9.

Morgan, V., "Nobex: No Barriers" Overview. No date. File created Jun. 14, 2006; Nobex Corporation, Research Triangle Park, NC; 2 pp.

Quintana, A., et al., "Design and Function of a Dendrimer-Based Therapeutic Nanodevice Targeted to Tumor Cells Through the Folate Receptor" Pharmaceutical Research, vol. 19, #9, pp. 1310-1316; Sep. 2002.

Henry, C., "Cooking Cancer—Carbon Nanotubes and Near-Infrared Radiation Kill Cancer Cells By Heating" Chemical & Engineering News, vol. 83, #32, p. 16; 2005.

Yan, X., et al., "Cisplatin Delivery from Poly(acrylic acid-co-methyl methacrylate) Microparticles", Journal of Controlled Release, vol. 106, #1-2, pp. 198-208; Aug. 2005.

Nishino, S., et al. "Preparation and Interfacial Properties of a Novel Biodegradable Polymer Surfactant: Poly(ethylene oxide monooleate-*block*-DL-lactide)", Macromolecular Bioscience; vol. 5, pp. 1066-1073; 2005.

Anon. "Biodegradable Polymers: A Review" Environment and Plastics Industry Council (EPIC) Technical Report pp.1-11; Nov. 24, 2000.

Anon. "What Are the Latest Drug Delivery Systems Made Of?" Online Publication Science Scotland; The Royal Society of Edinburgh; Issue 2, pp. 9-10; Spring 2004.

Hadlington, S. "Special Delivery", "Chemistry World" (online edition, previously "Chemistry in Britain"), Royal Society of Chemistry, UK; No. 5, pp. 1-3; May 2003.

Chiu "Synthesis and Characterization of Amphiphilic Polyethylene Glycol Graft Copolymers and That Potential Application As Drug Carriers", Polymer, vol. 39, No. 8-9, pp. 1609-1616, Apr. 1998.

Extended European search report on European Application 12156847.1, dated Aug. 21, 2012.

* cited by examiner

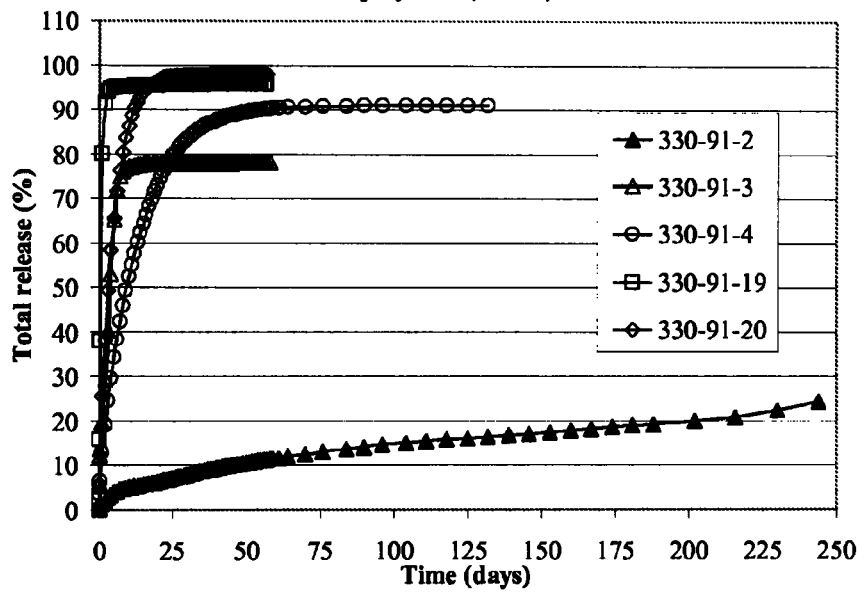
Figure 1 Cumulative release of diclofenac sodium from CYSC polymers (1st set) at 37°C
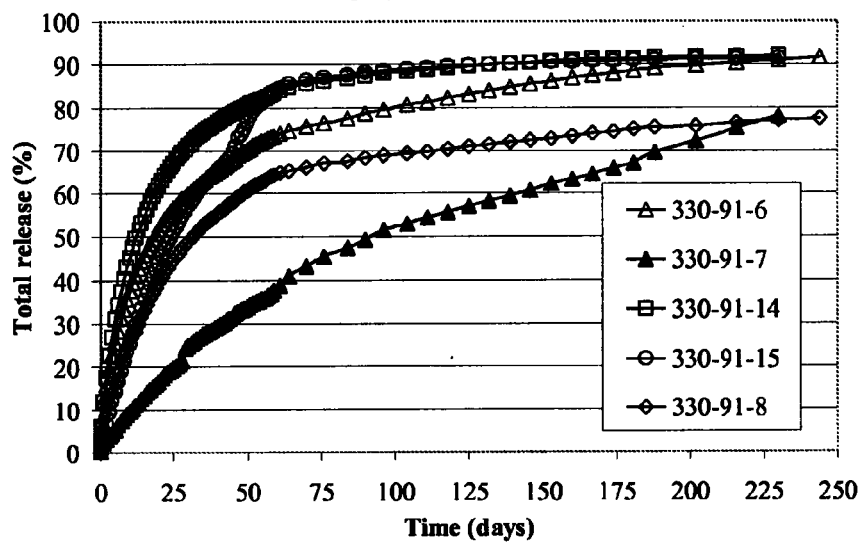
Figure 2 Cumulative release of diclofenac sodium from CYSC polymers (2nd set) at 37°C

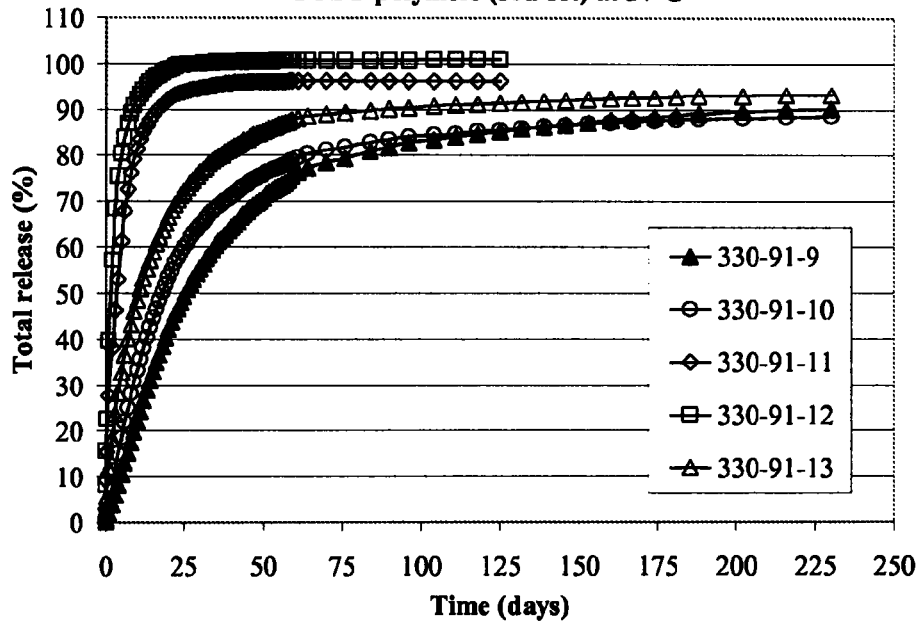
Figure 3  Cumulative release of diclofenac sodium from CYSC polymers (3rd set) at 37°C
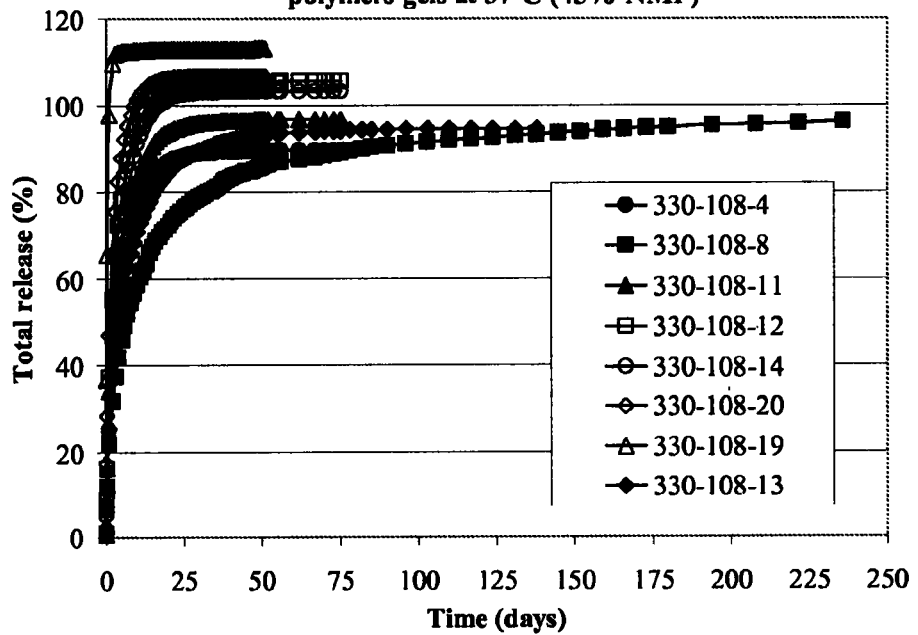
Figure 4  Cumulative release of diclofenac sodium from CYSC polymers gels at 37°C (45% NMP)

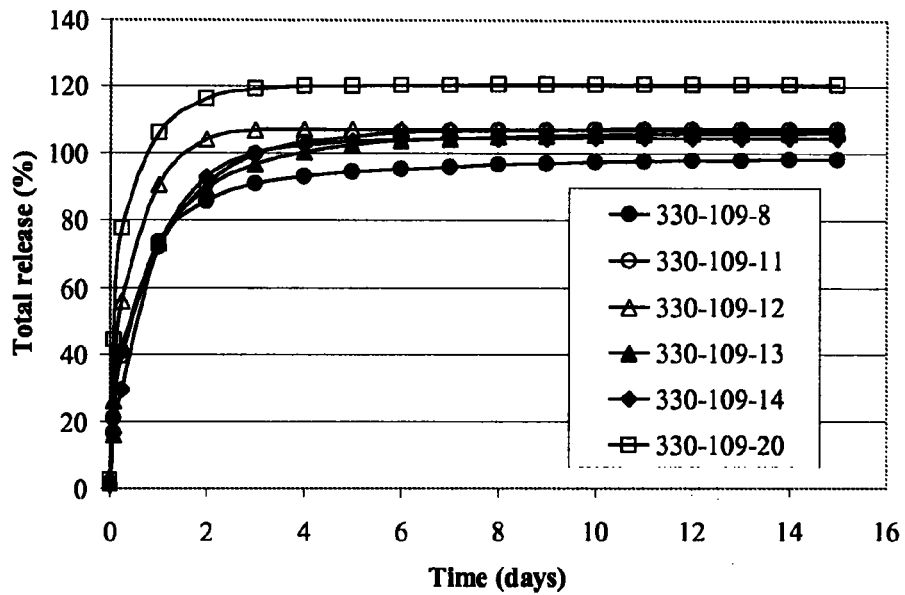
Figure 5  Cumulative release of diclofenac sodium from CYSC polymers gels at 37°C (82% NMP)
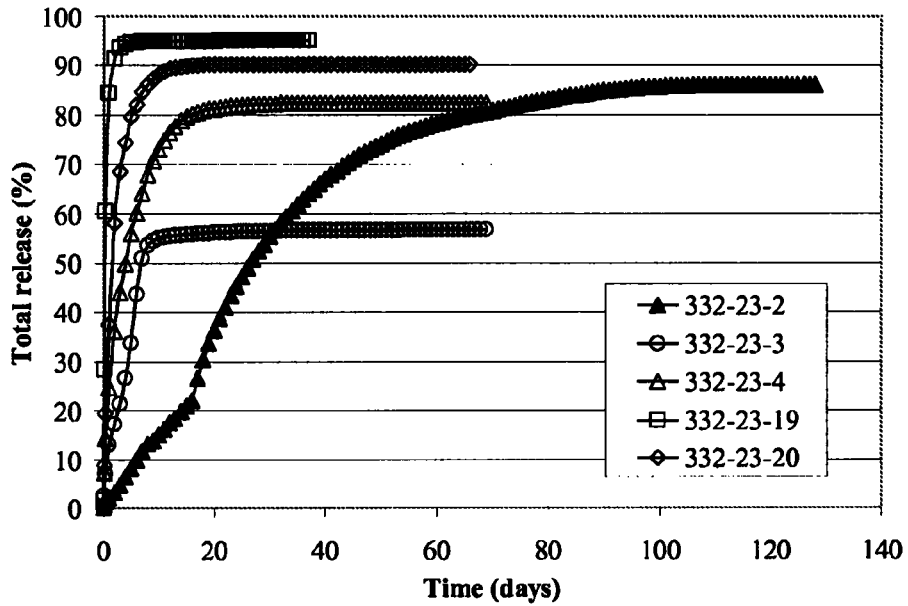
Figure 6  Cumulative release of diclofenac sodium from CYSC polymers at 37°C (16.7% loading, 1st set)

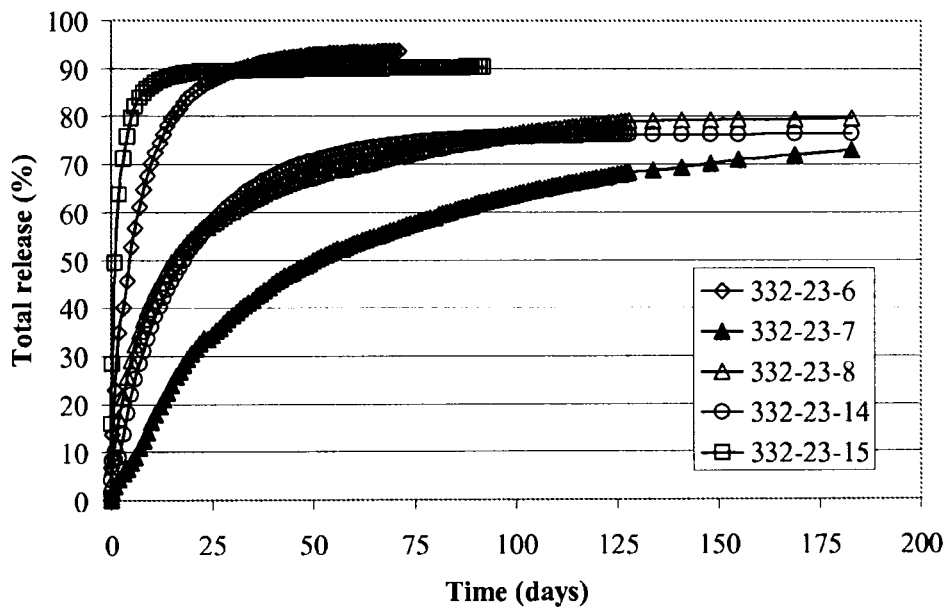
Figure 7  Cumulative release of diclofenac sodium from CYSC polymers at 37°C (16.7% loading, 2nd set)
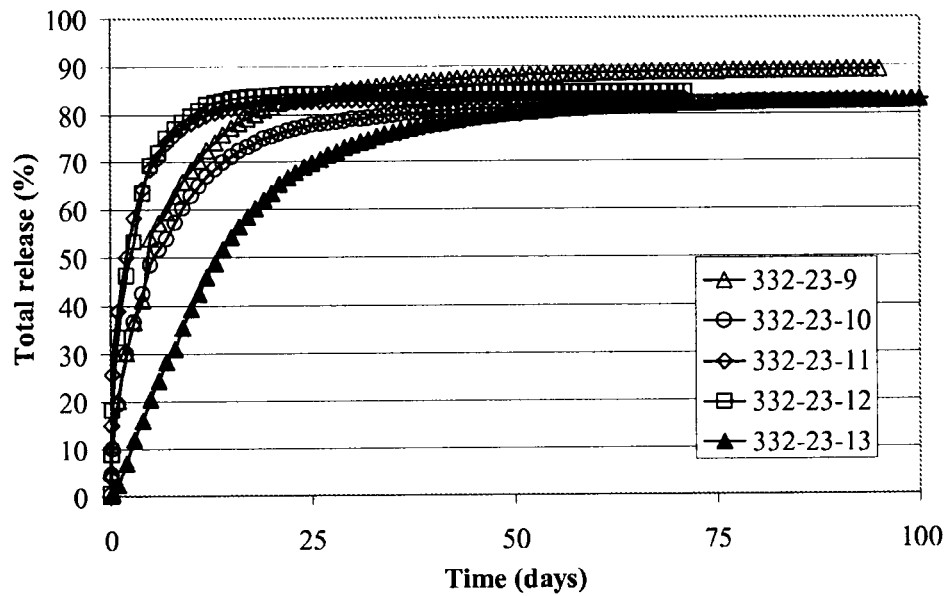
Figure 8  Cumulative release of diclofenac sodium from CYSC polymers at 37°C (16.7% loading, 3rd set)

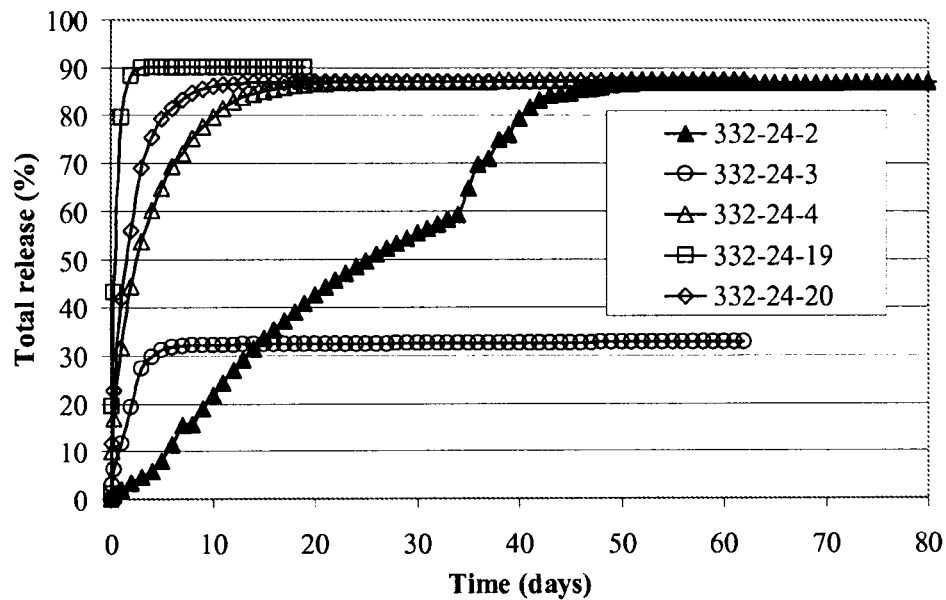
Figure 9  Cumulative release of diclofenac sodium from CYSC polymers at 37°C (23.1% loading, 1st set)
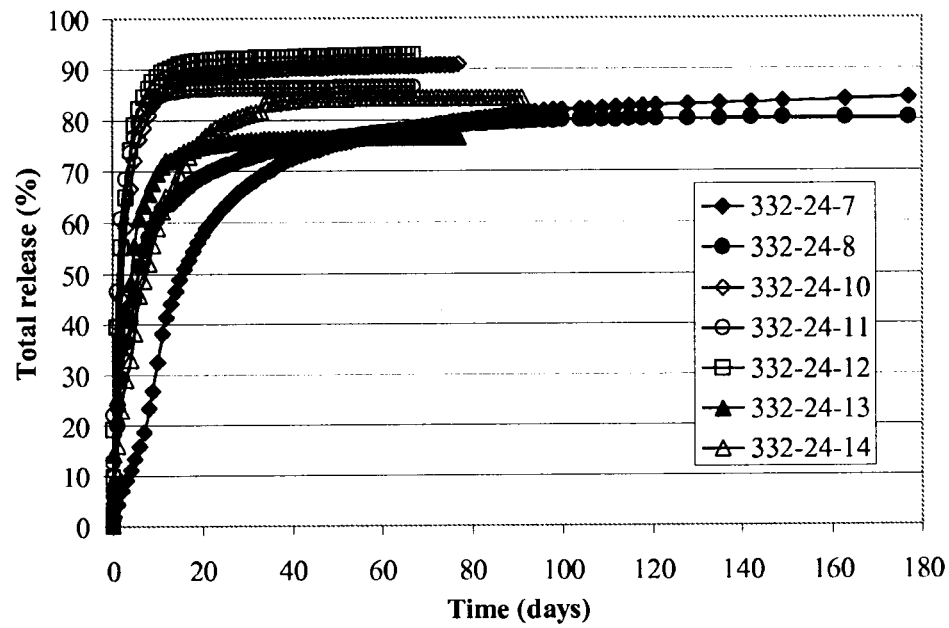
Figure 10  Cumulative release of diclofenac sodium from CYSC polymers at 37°C (23.1% loading, 2nd set)

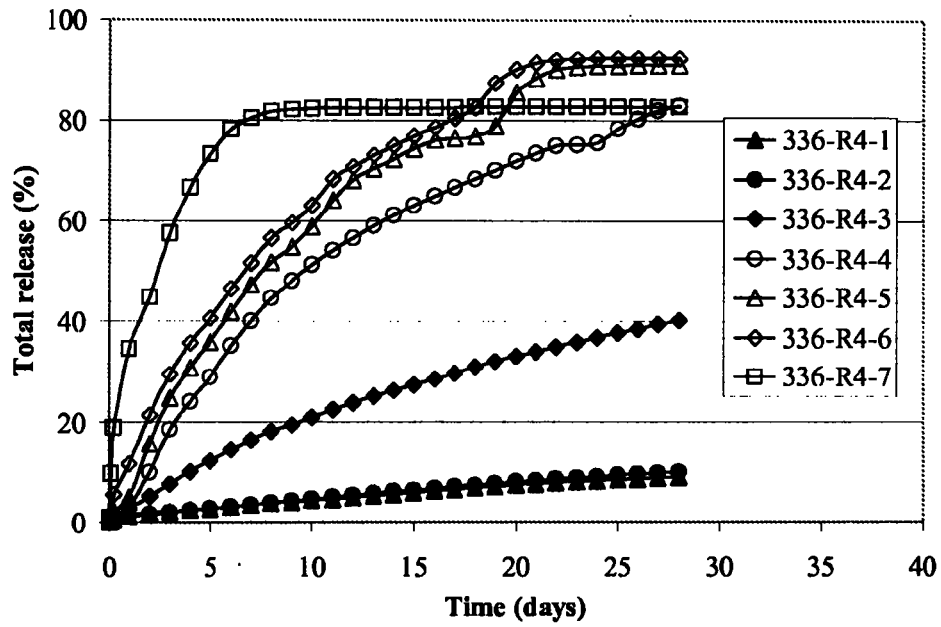
Figure 11  Cumulative release of diclofenac sodium from CYSC polymer 2A at 37°C (4.8-37.5% loading)
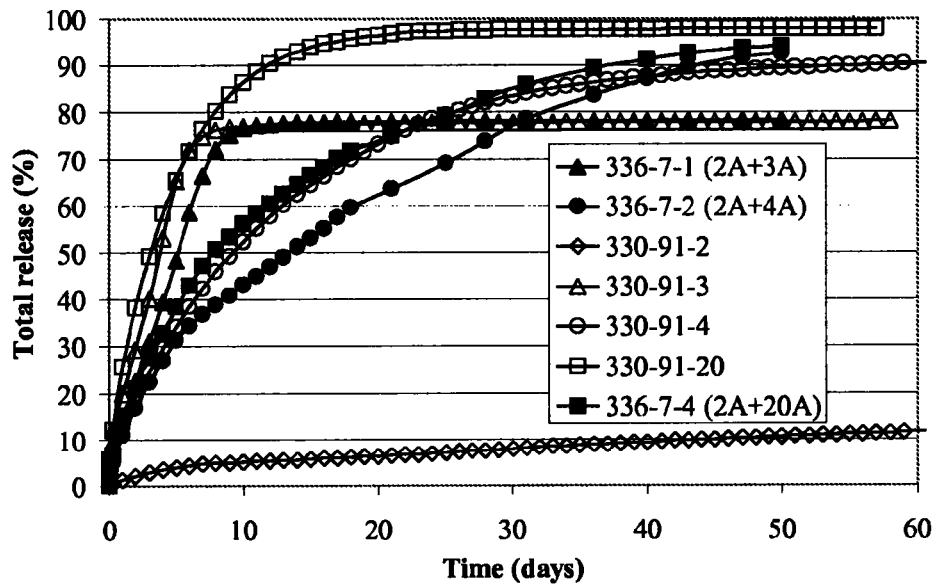
Figure 12  Cumulative release of diclofenac sodium from CYSC polymer mixtures at 37°C Figure 13  Cumulative release of diclofenac sodium from CYSC polymers with higher Tm at 37°C
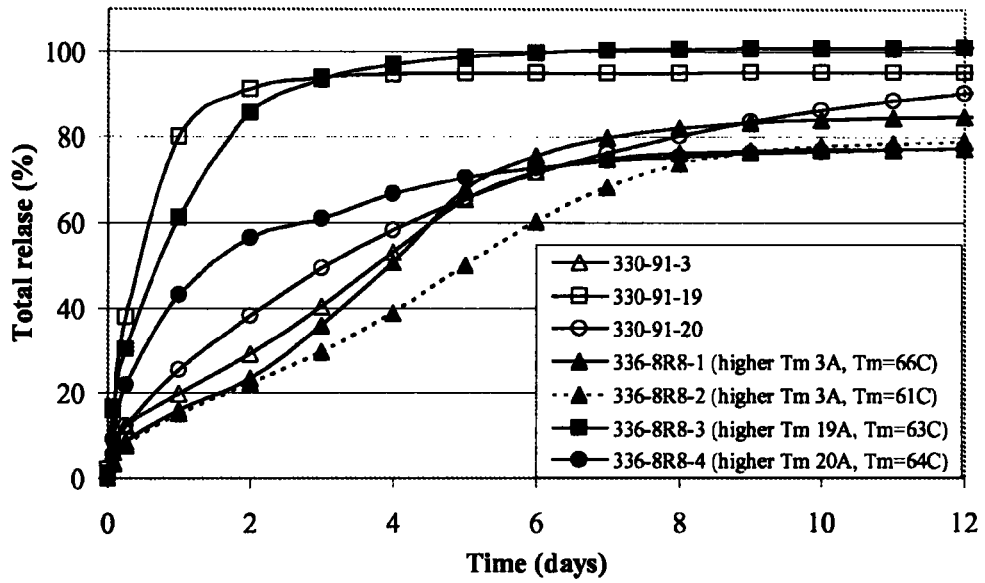
Figure 14  Cumulative release of diclofenac sodium from uniform 2 phase mixtures of CYSC polymers at 37°C
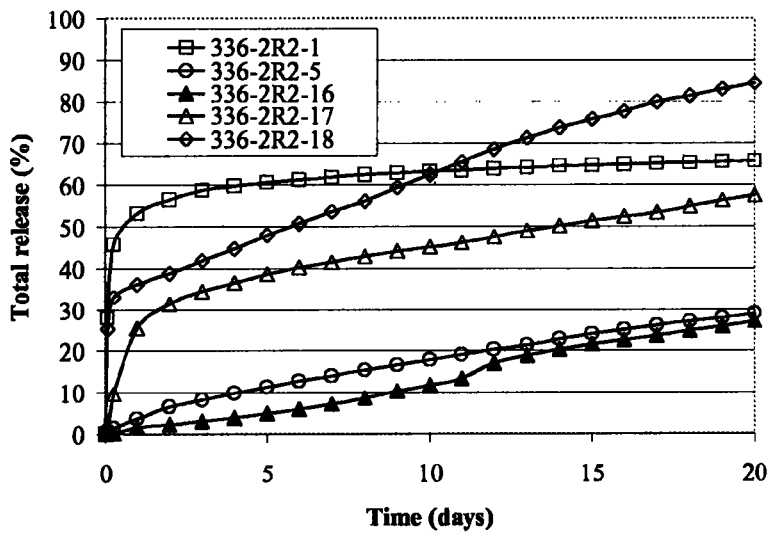

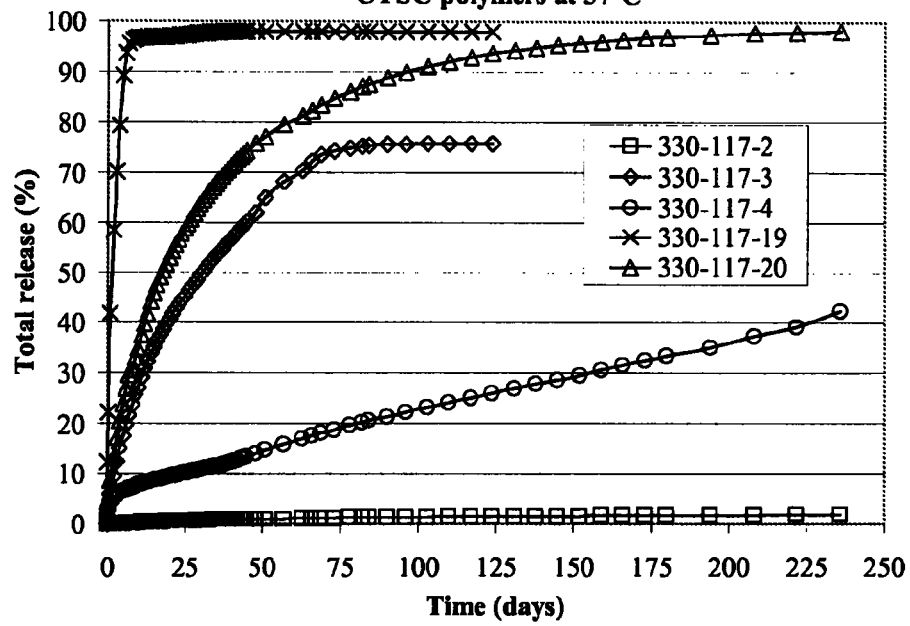
Figure 15  Cumulative release of risperidone from CYSC polymers at 37°C
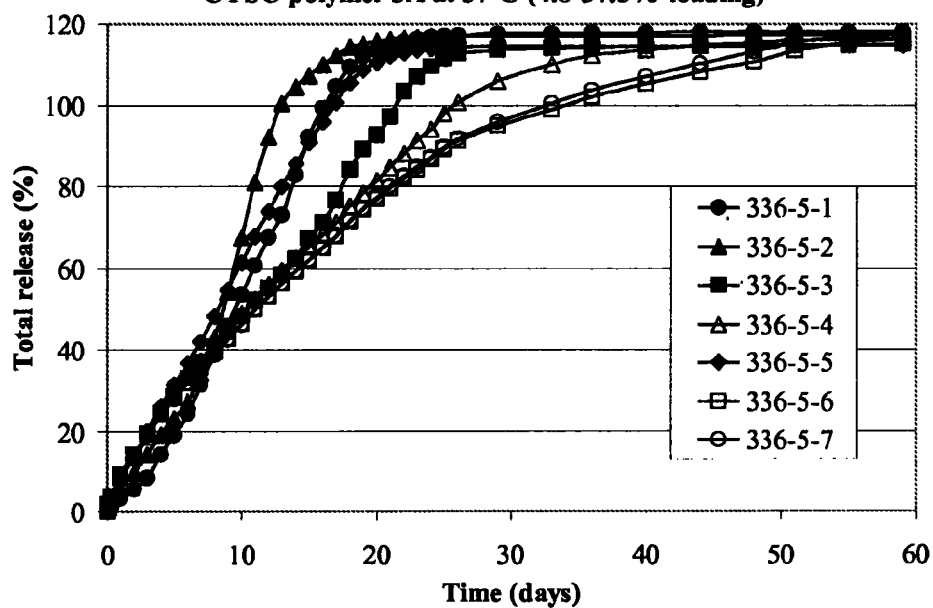
Figure 16  Cumulative release of risperidone from CYSC polymer 3A at 37°C (4.8-37.5% loading)

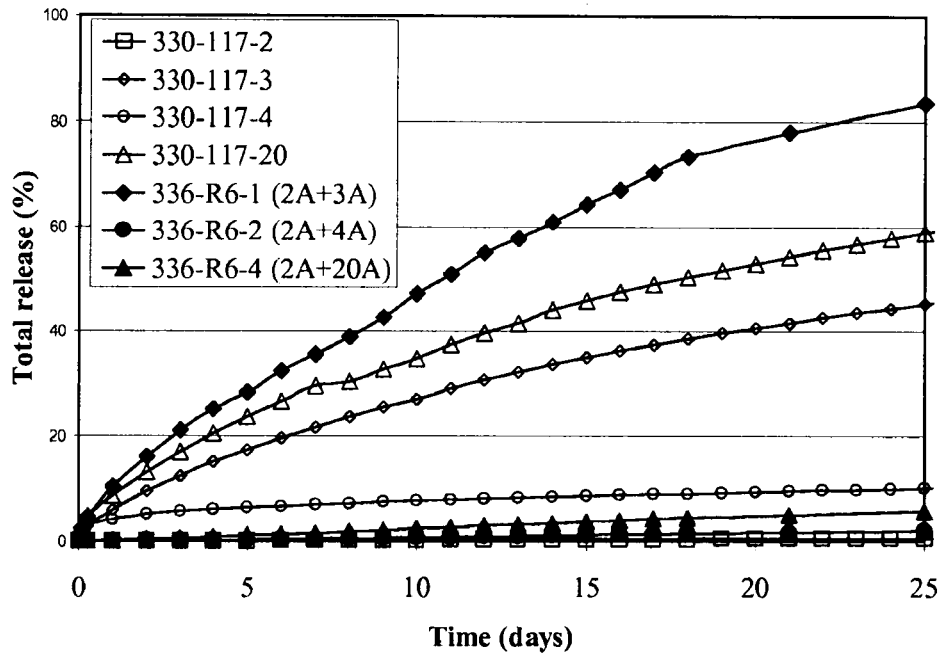
Figure 17 Cumulative release of risperidone from CYSC polymer mixtures at 37°C
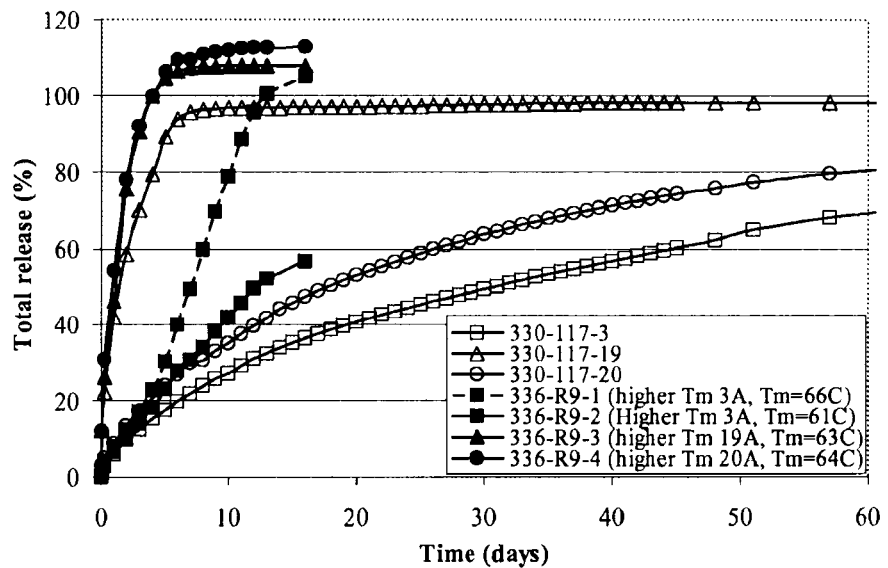
Figure 18 Cumulative release of risperidone from CYSC polymers with higher Tm at 37°C

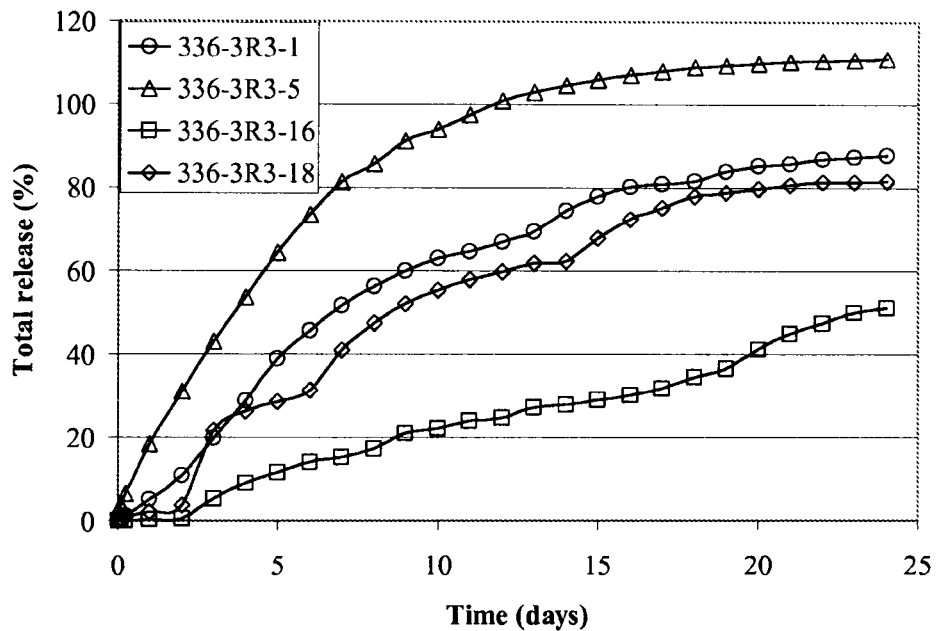
Figure 19  Cumulative release of risperidone from uniform 2 phase mixtures of CYSC polymers at 37°C
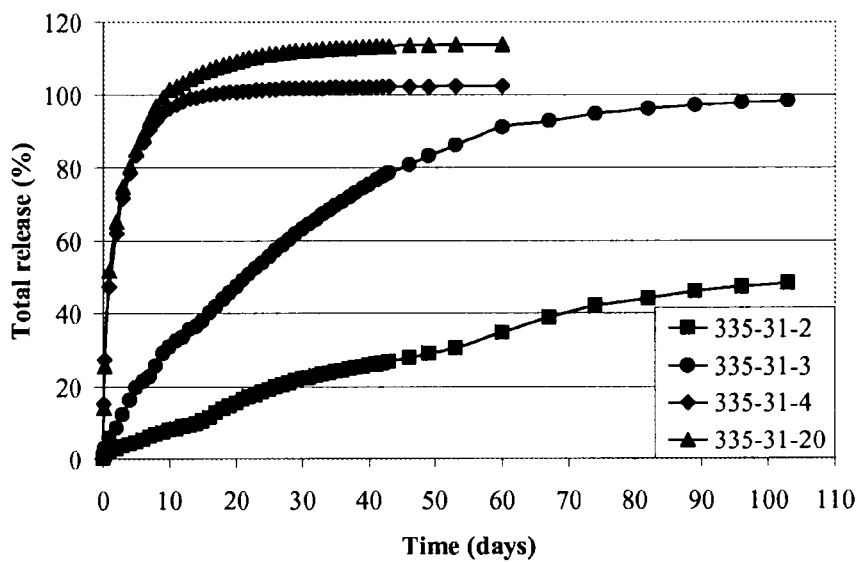
Figure 20  Cumulative release of risperidone from CYSC polymers in powder form at 37°C

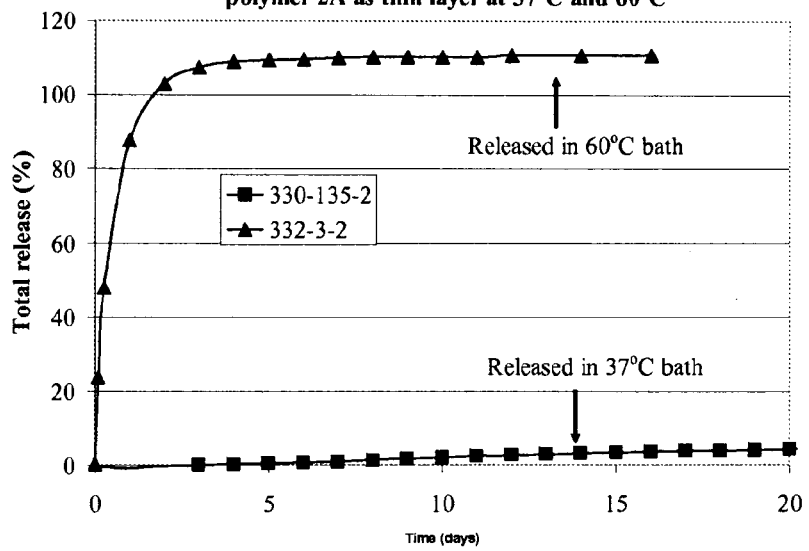
Figure 21  Cumulative release of risperidone from CYSC polymer 2A as thin layer at 37°C and 60°C
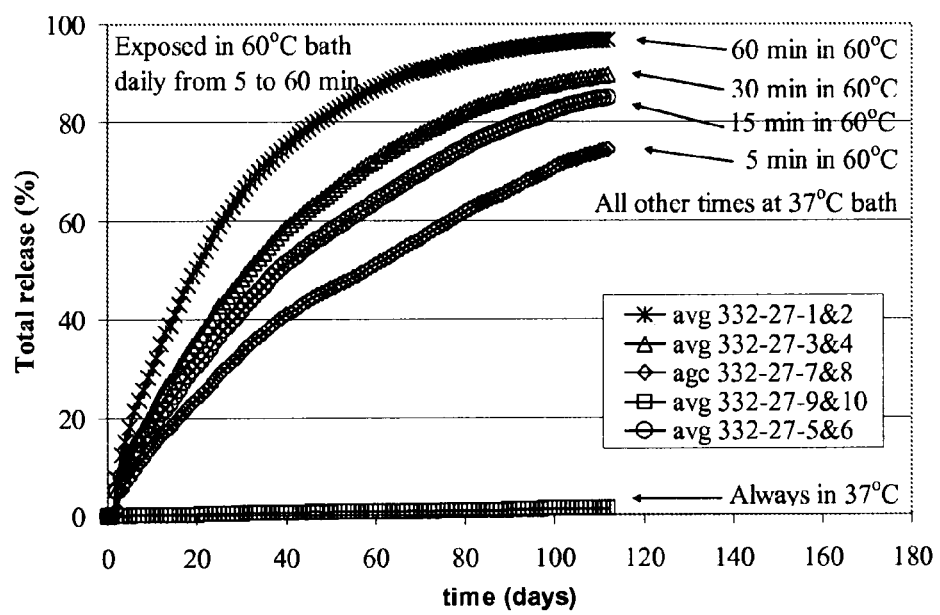
Figure 22  Dynamic temperature triggered release of risperidone from CYSC polymer 2A at 37°C and 60°C

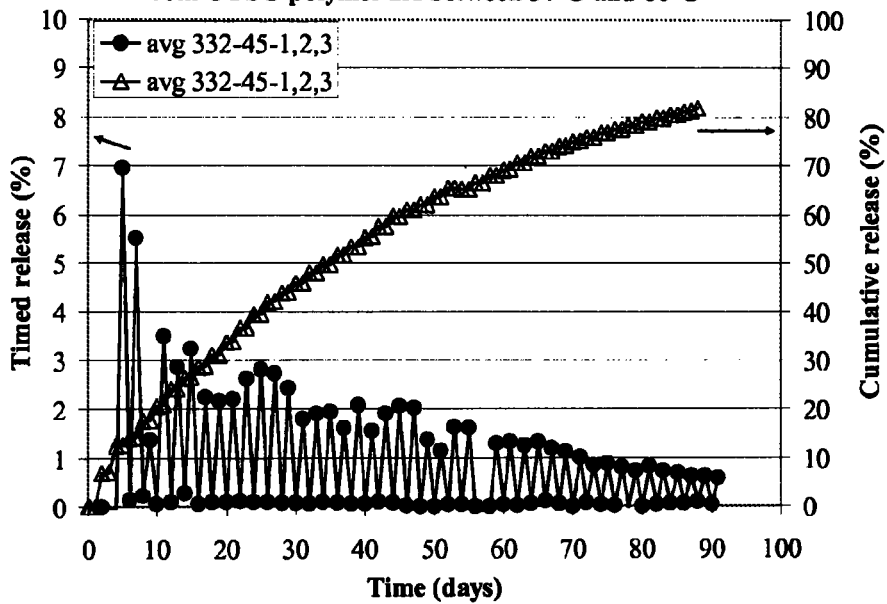
Figure 23  Dynamic temperature triggered release of risperidone from CYSC polymer 2A between 37°C and 60°C
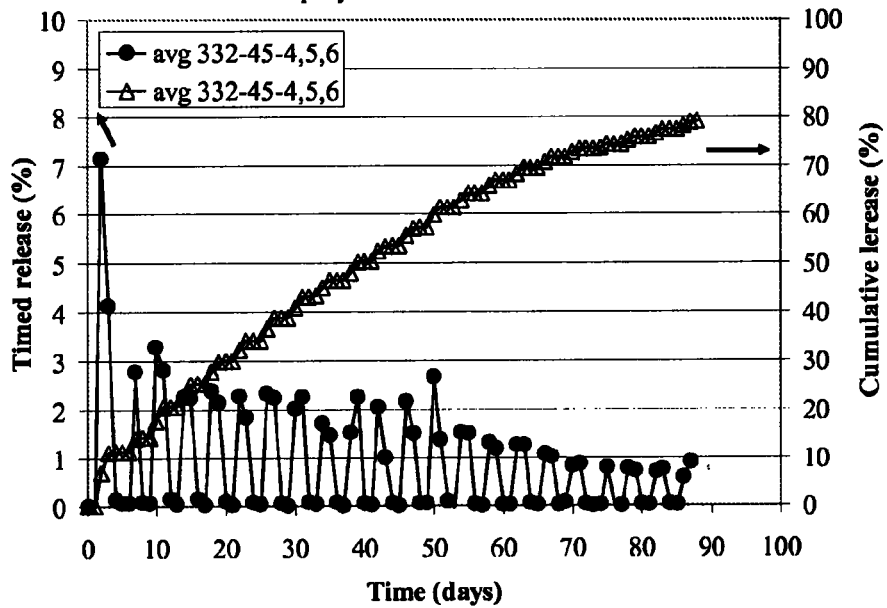
Figure 24  Dynamic temperature triggered release of risperidone from CYSC polymer 2A between 37°C and 60°C

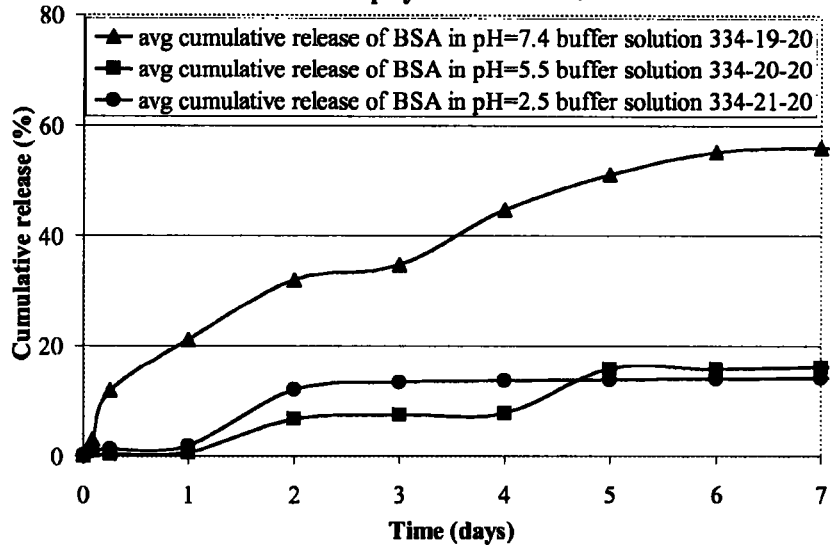
Figure 25  Static pH triggered release of risperidone from CYSC polymer 20A at 37°C
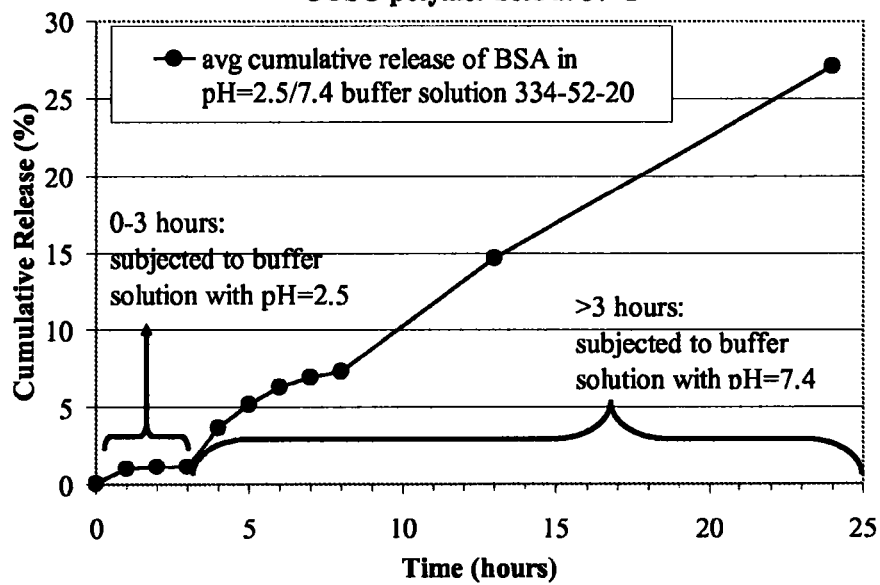
Figure 26  Dynamic pH triggered release of risperidone from CYSC polymer 20A at 37°C

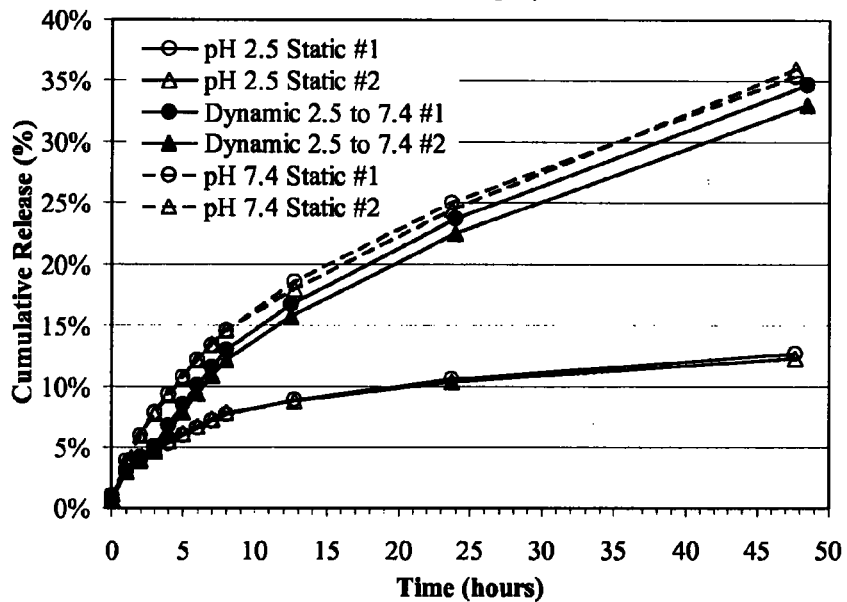
Figure 27. Static and dynamic pH triggered release of Leuprorelin from CYSC polymer #20 at 37°C
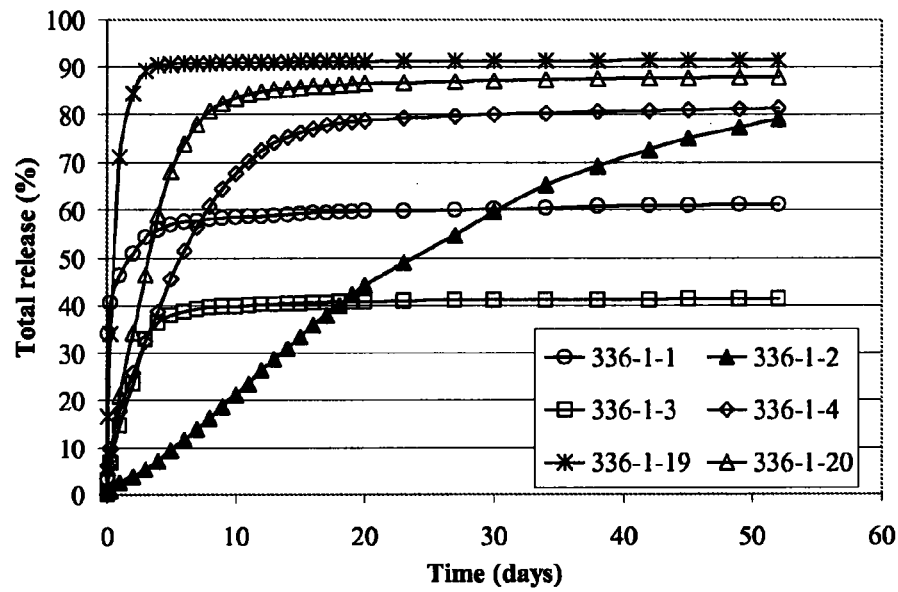
Figure 28. Cumulative release of pravastatin sodium from CYSC polymers at 37°C

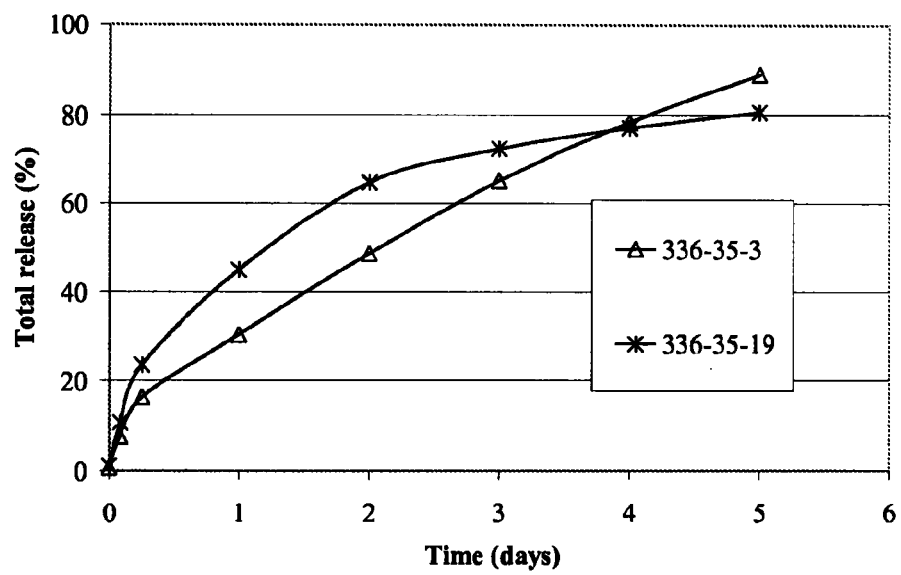
Figure 29  Cumulative release of dexamethasone sodium from CYSC polymers at 37°C
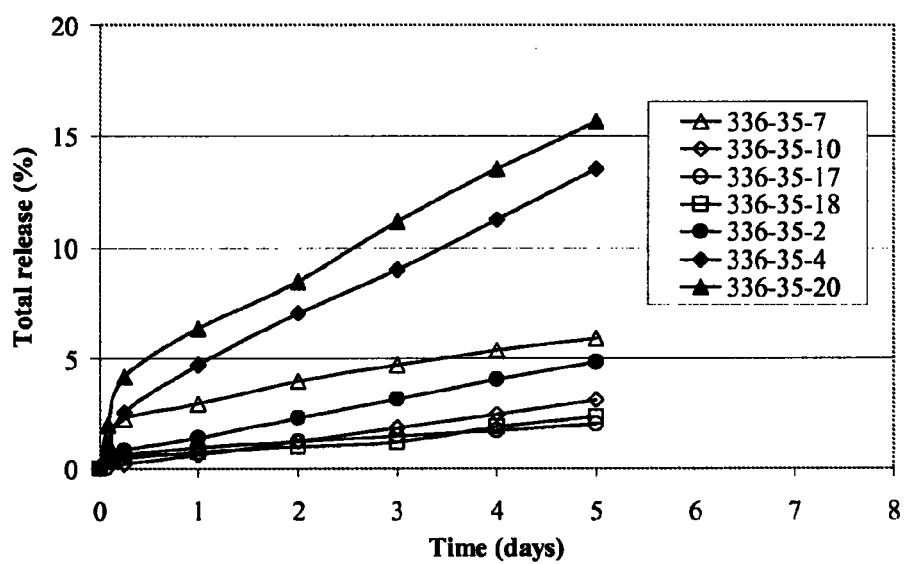
Figure 30  Cumulative release of dexamethasone sodium from CYSC polymers at 37°C

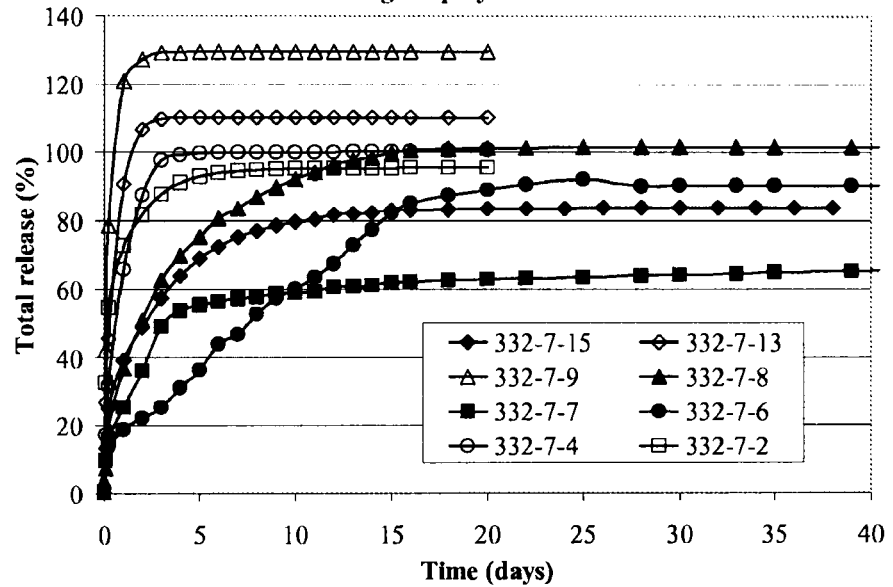
Figure 31 Cumulative release of diclofenac sodium from C12A analogs of polymers 1A-20A at 37°C
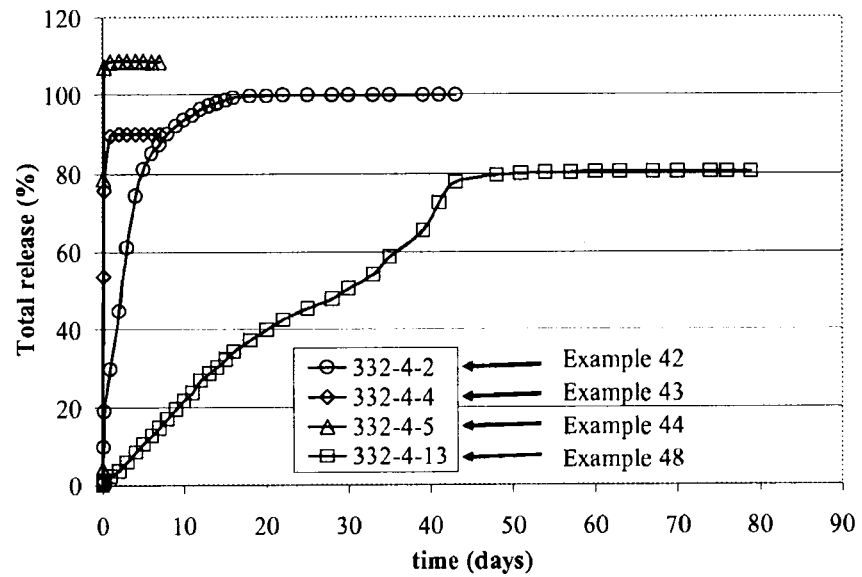
Figure 32 Cumulative release of diclofenac sodium from commercial polymers (examples 41-51) at 37°C

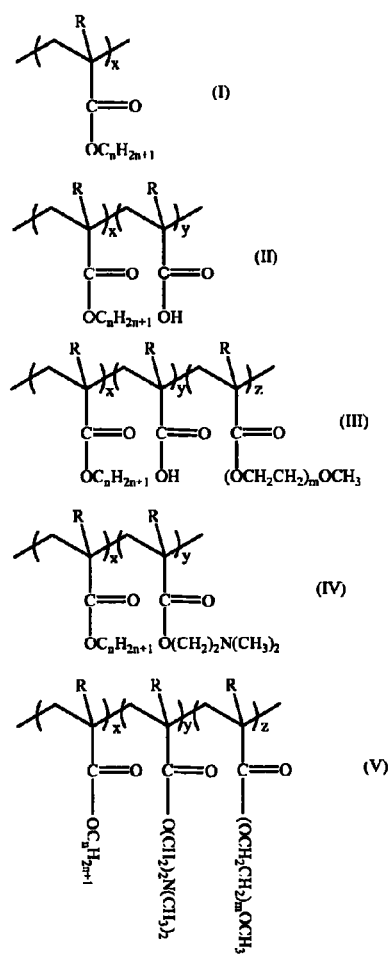
Figure 41  General chemical structure of CYSC polymers (R=H or CH$_3$, n ≥ 12, m ≥ 2)

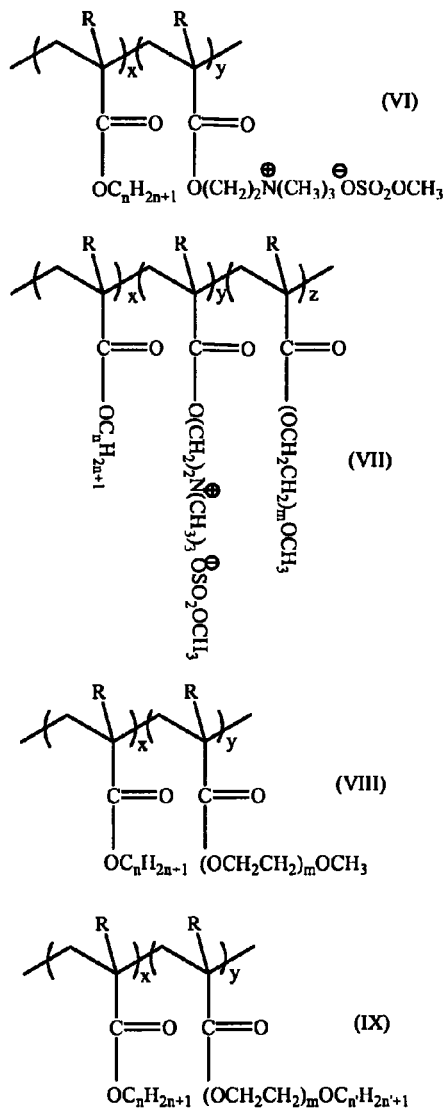
Figure 42  General chemical structure of CYSC polymers (R=H or CH$_3$, n, n' ≥ 12, m ≥ 2)

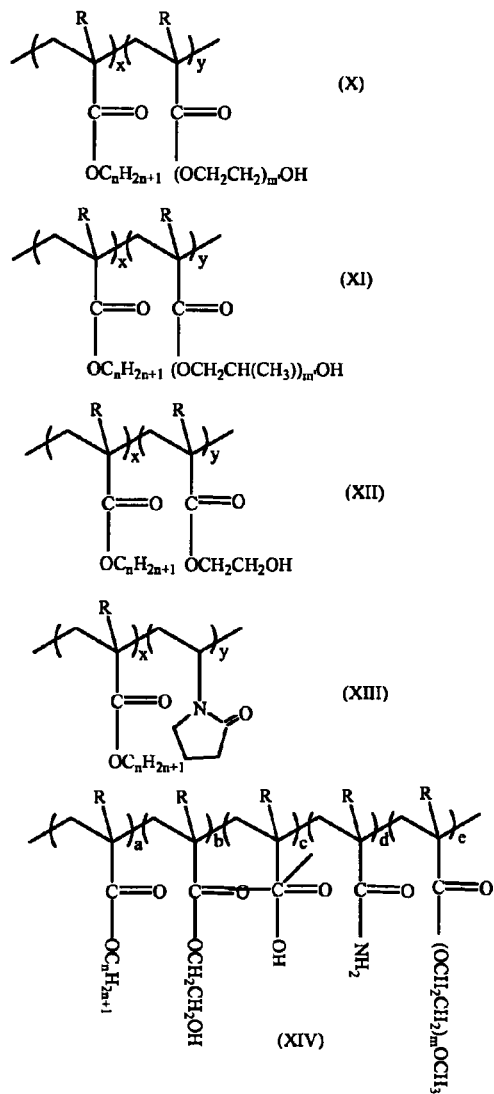
Figure 43 General chemical structure of CYSC polymers (R=H or CH$_3$, n ≥ 12, m ≥ 2)

Figure 44    Group #1: Risperidone IV Control
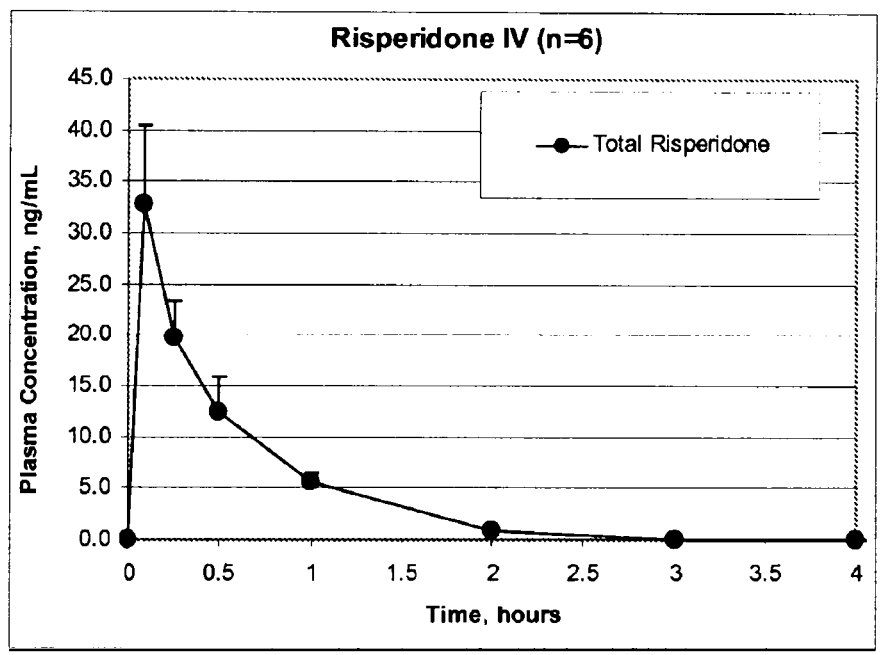

Figure 45    Group#2: Polymer # 336-19-2
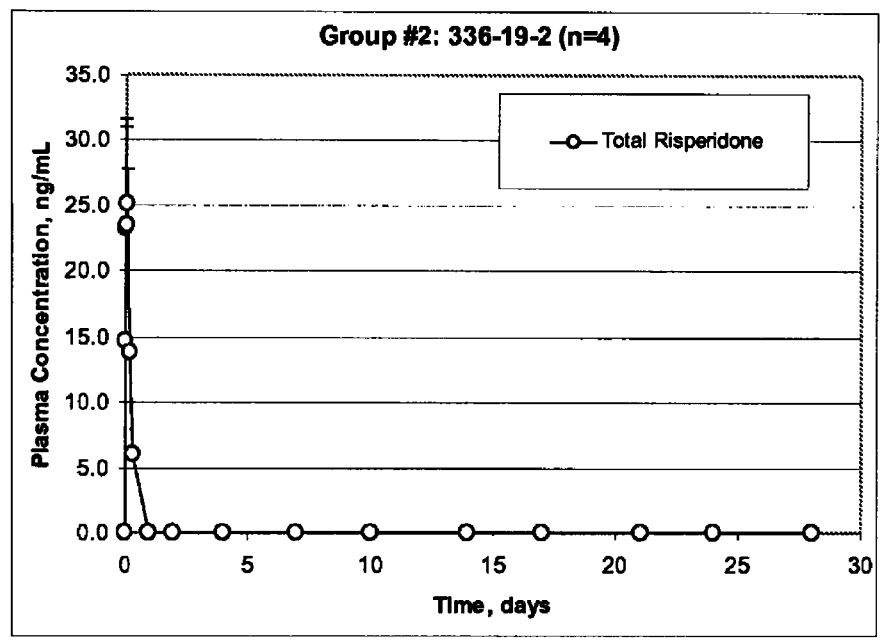

Figure 46  Group #3: 336-19-4
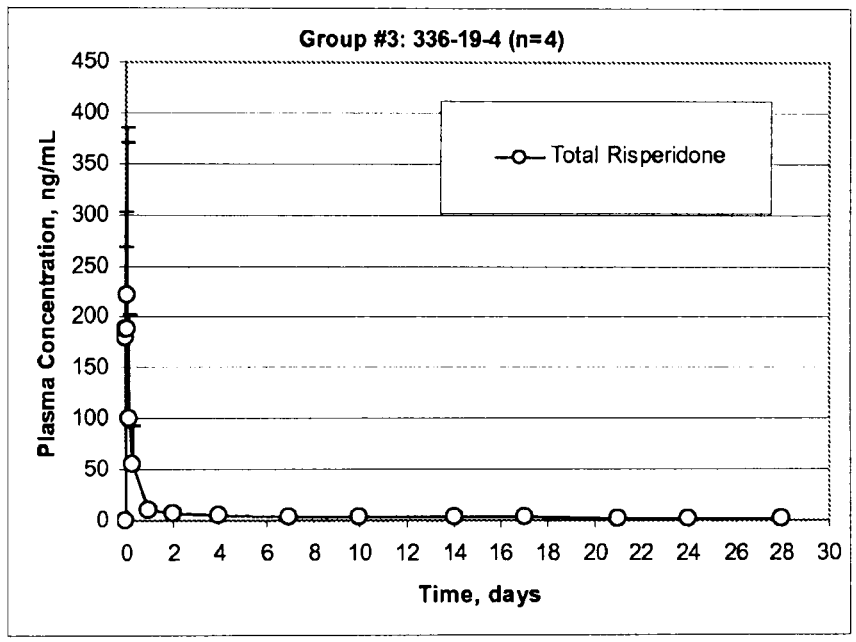
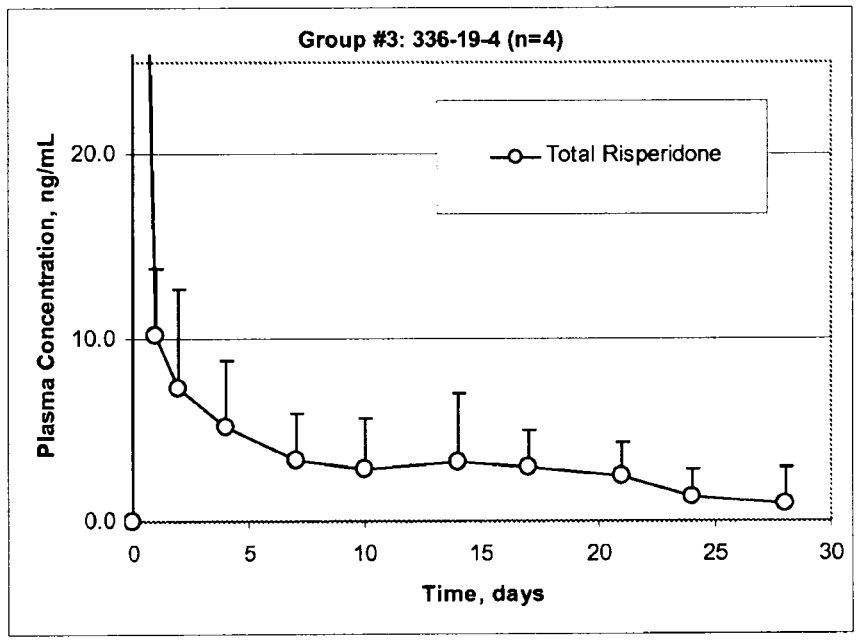

Figure 47  Group #4: 336-19-3
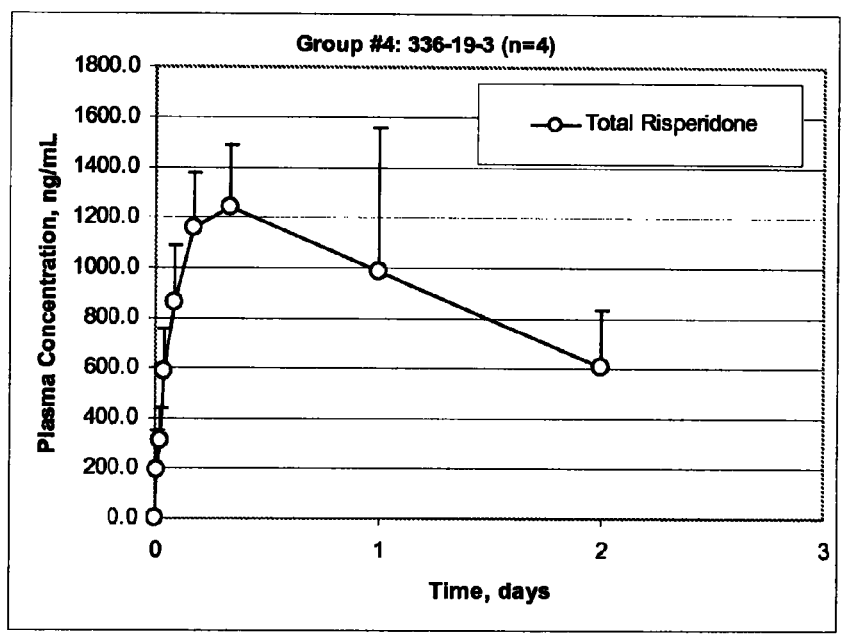

Figure 48    Group #5: 336-19-20
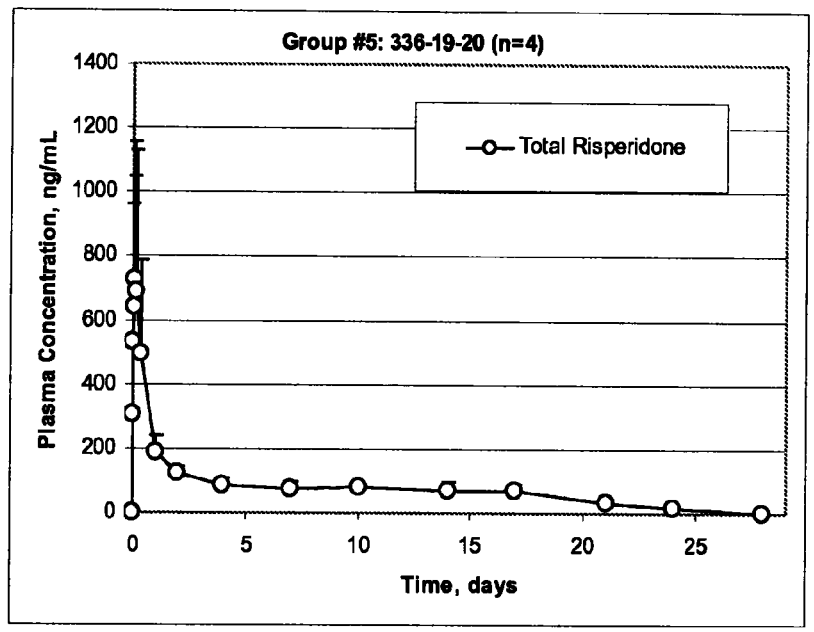
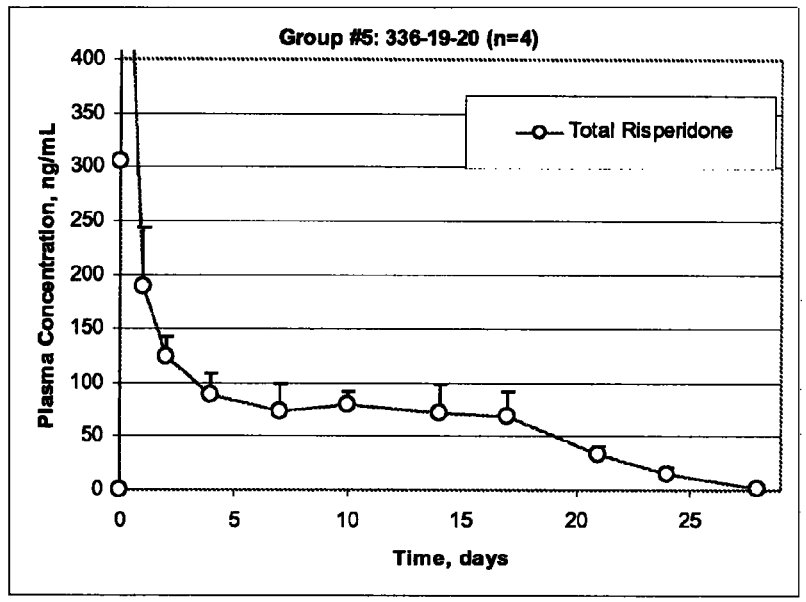

Figure 49   Group #6: Control Implant 336-20-2
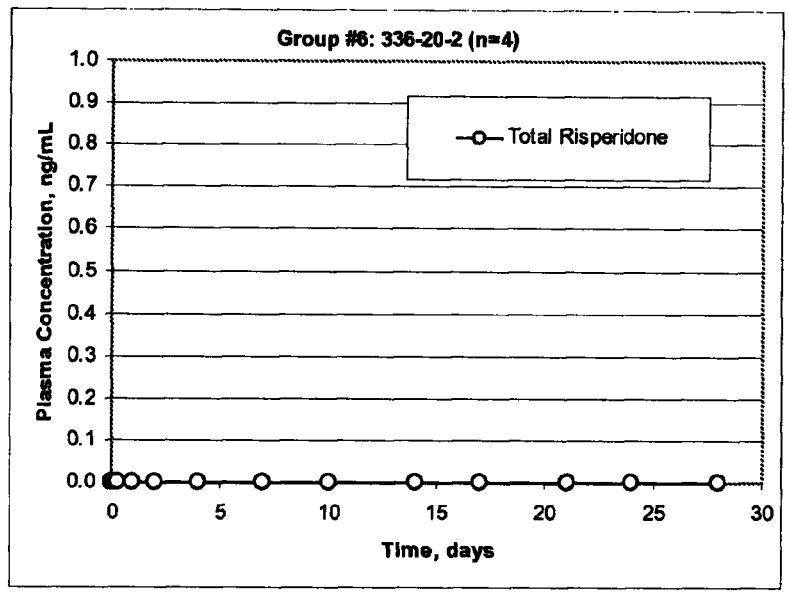
1. Group #6: Control Implant 336-20-20
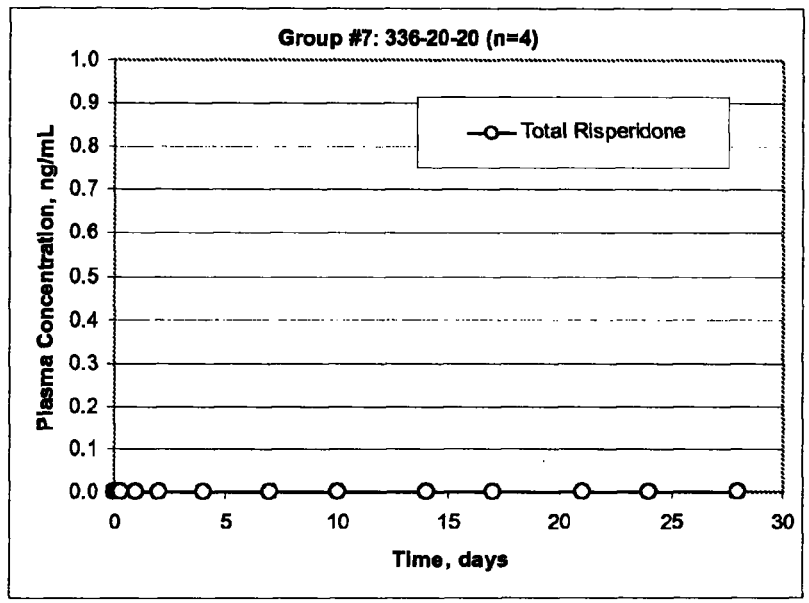

DELIVERY OF DRUGS

CROSS-REFERENCE TO RELATED APPLICATION

This application claims priority to and the benefit of U.S. provisional Application No. 60/873,234, filed Dec. 5, 2006, the entire disclosure of which is hereby incorporated by reference for all purposes.

FIELD OF THE INVENTION

This invention relates to polymeric systems for the delivery of drugs.

BACKGROUND

There are many known polymeric systems for the delivery of drugs. A continuing problem is obtaining a desired rate of delivery at a desired location and at a desired time. The desired rate may be, for example, a steady rate over a relatively long period of time, and/or a relatively rapid rate over a relatively short period of time ("bolus" delivery).

SUMMARY OF THE INVENTION

We have discovered, in accordance with the present invention, that useful delivery of drugs can be obtained through the association of drugs with certain polymers which are referred to herein as CYSC polymers (an abbreviation for crystallizable side chain polymers).

Documents describing drug delivery include for example U.S. Pat. No. 5,919,484, U.S. Pat. No. 6,423,345, US 2005/0249799, WO 2006/039152, U.S. Pat. No. 6,951,642, U.S. Pat. No. 6,656,385, US 2004/0236013, U.S. Pat. No. 6,699,952, U.S. Pat. No. 6,730,322, U.S. Pat. No. 6,964,778, U.S. Pat. No. 6,200,598, U.S. Pat. No. 6,524,274, US 2004/0052746, US 2004/0208844, WO 0187276, WO 2004/052339, U.S. Pat. No. 6,469,133, US. 2007/0142461, US 20010044514, U.S. Pat. No. 4,830,855, U.S. Pat. No. 4,558,690, U.S. Pat. No. 6,887,960, WO 99/36058, U.S. Pat. No. 6,951,642, U.S. Pat. No. 6,576,254, US 2006/0167116, J W Lee et al., Journal of Polymer Science, Part B Vol 38 #6, 823-830, J S Wei et al., Frontiers in Bioscience 10, supplement, 2005, Sep. 1, 2005, 3058-3067, C C Ng et al., J Sex Reprod Med Vol 1, #1 Summer 2001, pp 21-27, S Davaran et al., Journal of Controlled Release, 58, #3, pages 279-287 (1999), G Erdodi et al., Macromol. Sympos., Vol 227, 2005/July 2005, pp 265-273, Cheng et al., Biomacromolecules, 2006 May; 7(5):1509-20, C J Boudreaux et al., Journal of Controlled Release 44, #2-3, 1997 pp 185-194, V P Torchilin et al., Journal of Controlled Release Vol 73, #2, pages 137-172 (2001), V Bulmus et al., J Control Release 93, #2, 2003 Dec. 5, pp 105-120, K M Scholsky et al., J Controlled Release, 3, 87-108 (1986); Luppi et al, Eur-J-Pharm-Biopharm. 2003 March; 55(2): 199-202. The entire disclosure of each of those publications, patents and patent publications is incorporated herein by reference for all purposes.

The term "CYSC polymer" (an abbreviation for crystalline side chain polymer) is defined herein as a polymer which
(1) comprises at least one moiety which
  (i) has the formula --b-Cy--

(ii) forms part of a repeating unit which
    (a) provides at least part of the polymeric backbone of the polymer
    and
    (b) has formula (1) below,
    and/or
  (iii) forms at least part of a terminal unit of the polymer backbone which has formula (2) below

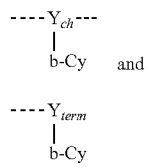

where
  $Y_{ch}$ is a trivalent moiety forming part of the backbone of the CYSC polymer,
  $Y_{term}$ is a divalent moiety at the end of the backbone of the CYSC polymer,
  b is a bond or a divalent moiety linking the Cy moiety to the polymer backbone, and
  Cy is a monovalent moiety which is capable of associating with other moieties (which may also be Cy moieties) to provide the CYSC polymer with crystallinity;
and
(B) has a crystalline melting temperature, Tp, of at least 0° C. and a heat of fusion of at least 5 J/g which results from the association of the Cy moiety (Tp and heat of fusion being measured on a DSC as hereinafter described).

The moiety -b--Cy is also referred to in this specification as an --Rc moiety, i.e. Rc is synonymous with -b--Cy. The CYSC polymers which contain a moiety of formula (2) above are sometimes referred to in this specification as end capped (ECC) polymers.

The moieties $Y_{ch}$, $Y_{term}$, b and Cy can be of any kind, and in CYSC polymers containing more than one moiety of formula (1) and/or more than one moiety of formula (2), $Y_{ch}$, $Y_{term}$, b and Cy can be the same or different. A wide variety of such moieties are described below. The CYSC polymer can optionally contain, in addition to the moieties of formula (1) and (2), repeating units and/or terminal units having a different formula. Purely by way of example, $Y_{ch}$ can be a

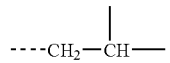

moiety, $Y_{term}$ can be a —$CH_2$—$CH_2$— moiety, b can be a —$CO_2$— moiety and Cy can be an n-alkyl moiety containing 18 carbon atoms.

Where reference is made in this specification to a moiety of formula —Y— or —Y(bCy)- or —Y(Rc)--, —Y— can be $Y_{ch}$ or $Y_{term}$.

A drug associated with a CYSC polymer can for example be delivered at a controlled rate and/or at a desired location, the rate and/or the location being influenced for example by a chemical and/or physical condition which modifies the association of the drug and the CYSC polymer. The condition can for example be an environment which causes the CYSC polymer to undergo a chemical change (for example the weakening or creation of any kind of chemical association, e.g. oxidation, reduction or hydration) and/or a change in physical state (for example the weakening or creation of any kind of physical association, e.g. a change in viscosity resulting from melting or crystallization, for example caused by internal or external heating) including an environment having a particular pH range, the presence of an enzyme. The term "controlled rate" includes, but is not limited to, a continuous, sustained rate, an increasing or decreasing rate, continuous or discontinuous release, or maintenance of a substantially constant rate. The drug may be released, for example, with zero-, first- or second-order release kinetics.

VARIOUS ASPECTS OF THE INVENTION (1) A novel composition comprising a CYSC polymer and a drug associated therewith. In some embodiments, the composition is a pharmaceutical formulation (alternatively referred to herein as a "formulation" or "drug formulation" or "dosage form") comprising a CYSC polymer and a drug, wherein the formulation is suitable for administration to a human being or other mammal or a composition which can be converted into such a formulation. The CYSC polymer and the formulation may be, for example, sterile or sterilizable, and/or biocompatible.

(2) Novel methods of controlling the release of a drug from a composition as defined above. The method may comprise subjecting the composition to conditions which affect the (i.e. decrease, increase or maintain substantially constant) the strength of the association between the drug and the CYSC polymer in at least part of the composition, for example at an exposed surface of the composition.

(3) Novel methods which make use of a CYSC polymer and a drug associated therewith, for example to improve or preserve the health of a mammal or cell, or to assist in the diagnosis of a mammal or cell.

(4) Novel methods of treating a mammal or cell which comprise administering a CYSC polymer and a drug to the mammal or cell, the polymer and drug being associated with each other before administration or becoming associated with each other during or after administration.

(5) Novel methods of making a composition as defined in (1). The composition is often made before the composition is administered, but the invention includes embodiments in which the composition is made or modified during administration and/or in situ in the mammal or cell as a result of simultaneous or sequential administration of the CYSC polymer and the drug. In various embodiments, the methods of making the composition involve mixing a drug and a CYSC polymer, in some embodiments specifically without the presence of a liquid (or solvent). In some embodiments, the CYSC polymer is at a temperature above its melting temperature but, below a temperature which would harm the drug (by denaturing it or affecting it in some way which would substantially reduce its activity or produce degradation products that would reduce its short-term or long-term stability. In other embodiments, the mixing is carried out in the presence of a liquid (which liquid may be a solvent for one or other or both or neither of the drug and the polymer). The liquid can be for example, water, an aqueous solvent, a non-aqueous solvent (e.g. an aliphatic, aromatic or mixed aliphatic/aromatic organic solvent), a polar solvent, or a non-polar solvent. The CYSC polymers can often be designed to melt over a relatively narrow temperature range and at a desired temperature between 10 and 120° C. (as measured on a differential scanning calorimeter (DSC) as described below). Furthermore, it is possible to obtain similar melting characteristics over a relatively wide range of molecular weight. The melting point can for example be about 30° C., about 35° C., about 37° C., about 40° C., about 45° C., about 50° C., about 55° C., about 60° C., about 65° C., about 70° C., about 75° C., or about 80° C. The melting point of a composition comprising a CYSC polymer and a drug will often be different from, generally lower than, the melting point of the CYSC polymer. When the drug is a drug to be administered to a mammal, it is often desirable for the composition to have a melting temperature above the body temperature of the mammal (e.g. above 37° C.). However, in some embodiments, the composition preferably has a melting temperature below 37° C., so that the composition, once implanted, maintains a non-solid consistency.

The relatively low melting point and narrow melting range of many CYSC polymers is particularly useful for making compositions containing a drug which is adversely affected by exposure to elevated temperatures and/or to solvents. For example, it is a well known problem that the preparation of many polymer-drug compositions requires either or both of elevated temperature or the presence of solvents, because many polymers, on their own, are sufficiently fluid only at elevated temperatures. Elevated temperatures can be harmful to the activity and/or the stability (short or long term) of many drugs and other drugs (for example but not limited to, proteins), and many solvents are known to have deleterious effects on drugs or on mammal or cells to which the compositions are administered, e.g. toxicity to mammals. In addition, exposure of drugs to such solvents may induce some chemical or physical degradation that may result in reduction of their potency or purity, either immediately upon exposure or during long-term shelf storage. In some embodiments, the present invention allows low temperature mixing of a drug and polymer, often without using a solvent.

(6) Novel uses of compositions comprising a CYSC polymer and a drug associated therewith.

(7) Novel devices for administering a CYSC polymer and a drug, the CYSC polymer and the drug being in the form of a composition as defined in (1) or being separately administered. Such devices can for example comprise a substrate coated with such a composition or with ingredients for forming such a composition, or a reservoir which acts as a depot which consists essentially of, or which contains, such a composition; or which comprises components which form such a composition before or after administration.

(8) The use of a composition or device as defined above, for example, the use of such a composition or device to deliver a therapeutically effective amount of a drug to a subject in a sustained manner over a protracted period of time, such as, for example, over at least 12 hours, over at least 24 hours or over at least 42 hours.

(9) Novel methods of making devices as defined above, the method comprising associating the drug with a CYSC polymer while the CYSC polymer is supported by a substrate, e.g. a polymeric or metal substrate.

(10) Novel methods of making devices as defined above, the method comprising contacting a substrate with a composition as defined in (1) or with components which form such a composition in situ (either after or during administration).

(11) Use of a composition comprising a CYSC polymer and a drug associated therewith in the manufacture of a medicament for the treatment of a condition in an mammal or cell.

(12) Compositions as defined in (1) which are formed in an mammal or cell after separate delivery to the mammal or cell of (i) a composition comprising the drug and (ii) a composition comprising the CYSC polymer.

(13) Methods which comprise administering to an mammal or cell, simultaneously or sequentially, (i) a composition comprising a drug and (ii) a composition comprising a CYSC polymer.

(14) Novel CYSC polymers for use in paragraphs (1)-(13) above and for other purposes.

(15) Methods of treating a composition as defined in (1) which reduce the rate at which drug is delivered from the composition when it is first exposed, for example by washing the surface of a solid shaped composition with a suitable organic or inorganic solvents, for example water.

Various embodiments of the invention include the following:

1. A pharmaceutical formulation comprising a drug and a CYSC polymer as hereinbefore defined. The CYSC polymer can for example comprise a plurality of Y(Rc) moieties and have a heat of fusion of at least 10 J/g. The CYSC polymer can have for example one or more Rc moieties, the moiety or each of the moieties if there is more than one, comprising a polymethylene moiety containing 11 to 49 methylene moieties. The CYSC polymer can for example be selected from the group consisting of: a poly-acrylate, a poly-methacrylate, a poly-alkyl-methacrylate, an poly-N alkyl methacrylamide, a poly-alkyl-acrylate, a poly-fluoroacrylate, a poly-N-alkyl acrylamide, a poly-alkyl oxazoline, a poly-alkyl vinyl ether, a poly-alkyl 1,2-epoxide, a poly-alkyl glycidyl ether, a polyvinyl ester, a poly-acrylamide, a poly-methacrylamide, a poly-maleimide, a poly-α-olefin, a poly-p-alkyl styrene, a poly-alkylvinyl ethers, a polyether, a polyester, a polyurethane, a polysilane, a polysiloxane, and a poly-alkyl phosphazene. These CYSC polymer can for example comprise a Rc moiety which comprises an n-alkyl moiety containing 14, 16, 18, 20, 22, 30, 40 or 50 carbon atoms. The CYSC polymer can for example comprise units derived from one or more monomers selected from the group consisting of: dimethylaminoethyl methacrylate, diethylaminoethyl methacrylate, t-butyl acrylamide, dimethylaminopropyl methacrylamide, N-isopropyl acrylamide, acrylonitrile, methacrylonitrile, N,N-dialkyl amino (in particular, dimethylamino) (meth)acrylates; ammonium salt-containing (meth)acrylates, for example 2-trimethylammonium methylmethacrylate chloride, methacrylamidopropyl trimethylammonium chloride, N,N-(diethyl or dimethyl)aminoethyl(meth)acrylate methosulfate; N-vinylpyrrolidinone; imides like the ring-closed reaction products of maleic or itaconic anhydride with primary amines; 2-methacryloxy-N-ethylmorpholine; n or t-butylacrylamide; (meth)acrylamide; dimethylaminopropyl methacrylamide; 2-t-butylaminoethyl methacrylate; (meth)acrylonitrile; t-butylaminoethyl (meth)acrylate; acryloylmorpholine; N-(2-hydroxyethyl)acetamide, 1-piperidinoethyl (meth)acrylate, acrylic acid, methacrylic acid; itaconic anhydride; itaconic acid; maleic anhydride; maleic acid; fumaric acid; monoesters and monoamides of fumaric acid, maleic acid, crotonic acid, and 2-acrylamido-2-methylpropane sulfonic acid ("AMPs"); vinyl sulfonic acid, vinyl acetate, hydroxyalkyl (meth)acrylates; tetrahydrofurfuryl (meth)acrylate; glycidyl methacrylate; alkoxyalkyl (meth) acrylate, e.g. methoxyethyl (meth)acrylate; 1-acryloxy-2-hydroxy-3-phenoxypropane; methylol methacrylate; ethoxyethyl (meth)acrylate; 2-(2-ethoxyethoxy)ethylacrylate; acetoacetoxyethyl (meth)acrylate; phenoxyethyl (meth)acrylate; (meth)acrolein; alkoxy or hydroxyl(polyoxyalkylene) alkyl (meth)acrylates, e.g. methoxy- or hydroxypolyoxyethylene (meth)acrylates, alkoxy- or hydroxypolyoxypropylene-polyoxyethylene alkyl (meth) acrylates, trifluoroethyl (meth)acrylate, heptadecafluorodecyl (meth)acrylate, octafluoropentyl (meth)acrylate, eicosafluoroundecyl (meth)acrylate, hexadecafluorononyl (meth)acrylate, tetrahydroperfluorodecyl (meth)acrylate; trimethylsiloxy ethyl(meth)acrylate, 3-acryloxypropyl trimethoxysilane, and 3-acryloxypropyl tris(trimethylsiloxy)silane, monomethacryloxymonotrimethylsiloxyterminated polyethylene oxide, and monomethacryloxypropyl alkyl polydimethylsiloxane where the alkyl group contains 1-8 carbon atoms. The CYSC polymer can for example contain repeating units of formula Z(Rz) as hereinafter defined, and optionally such repeating units include functionalized moieties. The CYSC polymer can for example have a $Tp-To<Tp^{0.7}$. The CYSC polymer can for example have a Mn molecular weight of between 1,000 Daltons and 100,000 Daltons. The CYSC polymer can for example have a Tp of between 38° C. and 60° C. The CYSC polymer can for example comprise hydrolytically labile bonds. The CYSC polymer can for example be free of mainchain crystallinity. The CYSC polymer can for example be a polymer other than a block copolymer or graft copolymer, e.g. a random copolymer. The CYSC polymer may or may not be a hydrogel The drug can for example be associated with the polymer by one or more associations selected from electrostatic bonds, hydrogen bonds, Van der Waals forces, covalent bonds, and entropic forces. The CYSC polymer can for example (i) contain one or more Rc moieties, the moiety or each of the moieties if there is more than one, comprising a polymethylene moiety containing 11 to 49 methylene moieties and (ii) have a melting temperature of not greater than 60° C.

The formulation can for example contain at least 5% by weight of the drug. The formulation can for example include a drug selected from the group consisting of anti-pain medications, anti-psychotics, anti-inflammatories, hormones, cholesterol lowering drugs, anti-osteoporosis drugs, anti-angeogenics and contraceptives. The formulation can for example include Risperidone or a pharmacologically active derivative, congener or metabolite thereof. The formulation can for example include a ligand that binds specifically to a target. The formulation can for example be one which, in vivo, when implanted within a subject, continuously releases a therapeutically effective dose of drug to the subject over a period of at least 30 days. The formulation can for example be one which, when tested in vitro (elution into 1 L PBS, pH 7.2 at 37° C., stirred at 100 rpm), releases the drug at an the average rate of release no greater than 50 milligrams per day averaged over any 24 hour period during the first 168 hours of elution. The formulation can for example be one which, when tested in vitro (elution into 1 L PBS, pH 7.2 at 37° C., stirred at 100 rpm), releases the drug at an average rate no greater than 25 milligrams per day averaged over any 24 hour period during a period from 12 hours to 168 hours following inception of elution. The formulation can for example be one which, when tested in vitro (elution into 1 L PBS, pH 7.2 at 37° C., stirred at 100 rpm), continuously releases between 1 milligram and 60 milligram of the drug per day over a period of at least 30 days. The formulation can for example be one which, when tested in vitro (elution into 1 L PBS, pH 7.2 at 37° C., stirred at 100 rpm), continuously releases between 1 milligram and 60 milligrams of the drug per day averaged over any 24 hour period during a period from 12 hours to 168 hours following inception of elution. The formulation can for example be one which, when tested in vitro (elution into 1 L PBS, pH 7.2 at 37° C., stirred at 100 rpm), releases no more than 10% by weight of the drug present in the formulation over a period of 24 hours. The formulation can for example be one which, when tested in vitro (elution into 1 L PBS, pH 7.2 at 37° C., stirred at 100 rpm), continuously releases a therapeutic dose of drug over a period of at least 30 days wherein the average 24 hour drug release rate is within one standard deviation of the 30 day mean. The formulation can for example be one which, in vivo, when implanted within a subject, continuously releases a therapeutic dose of drug over a period of at least 30 days.

2. A method for administering a drug to a subject, the method comprising
(1) administering to the subject a formulation as defined in (1), and (2) continuously releasing a therapeutically effective dose of the drug to the subject over a period of at least 30 days. Optionally the formulation is pretreated by contacting it with a liquid, e.g. a liquid buffer, before it is administered. The treatment can for example before a period of at least 30 minutes. The method can for example comprise implants in the formulation within the subject, for example subcutaneously. In some methods, the drug is Risperidone, and the therapeutically effective dose is between 1 mg and 60 mg per day. In some methods, the drug is Diclofenac sodium, and the therapeutically effective dose is between 50 mg and 300 mg per day. The method can for example comprise releasing the drug from the formulation at a predetermined time wherein the drug is released from the formulation by one or more of the following changes in condition
   (i) heating the formulation,
   (ii) hydration of the formulation,
   (iii) exposing of the formulation to an enzyme,
   (iv) changing the pH of the environment surrounding the formulation.

In certain embodiments the formulation may release a therapeutic dose of a drug only at or above a certain pH. For example, a formulation may release little or no drug in an aqueous environment at an acid pH (such as the stomach), but release a therapeutic dose or drug at a less acid pH such as at pH6, or at an alkali pH, such as pH7, pH8, pH9, or pH10 or above. This application is particularly useful for the oral delivery of acid albile drugs such as proteins or peptides that would be damaged by the acid environment of the stomach.

The CYSC polymer and the drug/CYSC polymer compositions used in the present invention can optionally have one or, where possible, more than one, of the following characteristics.

(1) The polymer does not contain 15-20 mole % methacrylic acid units.
(2) the polymer does not contain 20-40 mole % methacrylic acid units.
(3) The polymer does not contain 15-20 mole % acrylic acid or alkyl acrylic acid units
(4) the polymer does not contain 20-40 mole % acrylic acid or alkyl acrylic acid units
(5) the polymer does not contain side chains containing 18 carbon atoms
(6) the polymer does not contain side chains containing 12-18 carbons
(7) the polymer does not contain a carbon atom which is linked to the Cy moiety and also to a moiety containing a carboxyl or carboxyl salt moiety
(8) the polymer has a molecular weight less than 80,000, preferably less than 60,000.
(9) The polymer not in the form of a film.
(10) The polymer not a random copolymer.
(11) The polymer is not a thermoplastic elastomer
(12) the polymer is not an elastomer
(13) the polymer does not contain a Cy moiety which is attached to the polymer backbone through an anhydride linkage.
(14) the polymer does not contain a Cy moiety which contains anhydride linkages.
(15) the polymer does not contain units derived from a vinyl amide
(16) the polymer contains more than 40% of units containing Cy moieties
(17) the polymer does not hydrolyze when exposed to water.
(18) the polymer has a pKa greater than 4
(19) the polymer is not used as a gating membrane which is placed between an interior enclosure comprising the drug and an exterior volume into which the drive is to be dispensed.
(20) the polymer is not cross-linked or otherwise rendered nonflowable, e.g. by making it part of a block copolymer containing a high melting block, or immobilizing it within a microporous membrane, hollow fiber or fabric mesh.
(21) the polymer is not prepared by emulsion polymerization.
(22) Drug is a compound which would not be suitable for use in a composition applied to the skin.
(23) the drug is not 4-acetamido phenol.
(24) the drug is not nicotine.
(25) the drug is not pilocarpine
(26) the composition is not produced by dipping a film of the polymer into an aqueous solution of the drug.
(27) the composition is produced by dispersing the drug in the molten polymer.
(28) the composition is not produced by grinding the drug with the polymer while it is solid.
(29) the composition contains less than 45% of drug.
(30) the composition does not contain water.
(31) the composition does not contain an oil
(32) the composition is not a water-in-oil emulsion
(33) the composition is not an aqueous emulsion
(34) the rate at which the drug is dispensed from the composition is not controlled by controlled variation of the temperature of the CYSC polymer
(35) the drug is released from the CYSC polymer at a temperature below the melting point of the polymer
(36) composition is not used to block a channel in a mammal

BRIEF DESCRIPTION OF THE DRAWINGS

The invention is illustrated in the accompanying drawings in which many of the Figures summarize results obtained in the Examples, as identified in the Figures and as further as in the described below.

FIG. 1 (which is referred to in the published Application 20080269105 as FIG. C1) is a graph showing release of diclofenac sodium ($1^{st}$ set).

FIG. 2 (which is referred to in the published Application 20080269105 as FIG. C2) is a graph showing release of diclofenac sodium ($2^{nd}$ set).

FIG. 3 (which is referred to in the published Application 20080269105 as FIG. C3) is a graph showing release of diclofenac sodium ($3^{rd}$ set).

FIG. 4 (which is referred to in the published Application 20080269105 and in Examples 68-75 below as FIG. D1) is a graph showing release of diclofenac sodium from CYSC gel (45% NMP).

FIG. 5 (which is referred to in the published Application 20080269105 and in Examples 76-81 below as FIG. E1) is a graph showing release of diclofenac sodium from CYSC gel (82% NMP).

FIG. 6 (which is referred to in the published Application 20080269105 and in Examples 82-115 below as FIG. F1) is a graph showing release of diclofenac sodium from CYSC ($1^{st}$ set).

FIG. 7 (which is referred to in the published Application 20080269105 and in Examples 82-115 below as FIG. F2) is a graph showing release of diclofenac sodium from CYSC (16.7%, $2^{nd}$ set).

FIG. 8 (which is referred to in the published Application 20080269105 and in Examples 82-115 below as FIG. F3) is a graph showing release of diclofenac sodium from CYSC (16.7%, $3^{rd}$ set).

FIG. 9 (which is referred to in the published Application 20080269105 and in Examples 82-115 below as FIG. F4) is a graph showing release of diclofenac sodium from CYSC (23.1%, 1st set).

FIG. 10 (which is referred to in the published Application 20080269105 and in Examples 82-115 below as FIG. F5) is a graph showing release of diclofenac sodium from CYSC (23.1%, 2nd set).

FIG. 11 (which is referred to in the published Application 20080269105 and in Examples 82-115 below as FIG. F6) is a graph showing release of diclofenac sodium from CYSC 2A (4.8-37.5%).

FIG. 12 (which is referred to in the published Application 20080269105 and in Examples 116-118 below as FIG. G1) is a graph showing release of diclofenac from CYSC polymers.

FIG. 13 (which is referred to in the published Application 20080269105 and in Examples H1-H4 below as FIG. H1) is a graph showing release of diclofenac from CYSC polymers with higher Tms.

FIG. 14 (which is referred to in the published Application 20080269105 and in Examples 123-127 below as FIG. I1) is a graph showing release of diclofenac from CYSC 2 phase mixtures.

FIG. 15 (which is referred to in the published Application 20080269105 and in Examples 128-132 below as FIG. J1) is a graph showing release of risperidone from CYSC polymers.

FIG. 16 (which is referred to in the published Application 20080269105 and in Examples 133-139 below as FIG. K1) is a graph showing release of risperidone from CYSC polymer 3A.

FIG. 17 (which is referred to in the published Application 20080269105 and in Examples 140 142 below as FIG. L1) is a graph showing release of risperidone from CYSC polymer mixtures.

FIG. 18 (which is referred to in the published Application 20080269105 and in Examples 143-146 below as FIG. M1) is a graph showing release of risperidone from CYSC polymers.

FIG. 19 (which is referred to in the published Application 20080269105 and in Examples 147-150 below as FIG. N1) is a graph showing release of risperidone from CYSC 2 phase mixtures.

FIG. 20 (which is referred to in the published Application 20080269105 and in Examples 151-154 below as FIG. O1) is a graph showing release of risperidone from CYSC polymer powders.

FIG. 21 (which is referred to in the published Application 20080269105 and in Examples 155-156 below as FIG. P1) is a graph showing release of risperidone from CYSC A2 thin layers.

FIG. 22 (which is referred to in the published Application 20080269105 and in Examples 157-163 below as FIG. P2) is a graph showing temperature triggered release of risperidone from CYSC.

FIG. 23 (which is referred to in the published Application 20080269105 and in Examples 157-163 below as FIG. P3) is a graph showing temperature release of risperidone from CYSC 2A.

FIG. 24 (which is referred to in the published Application 20080269105 and in Examples 157-163 below as FIG. P4) is a graph showing temperature release of risperidone from CYSC 2A.

FIG. 25 (which is referred to in the published Application 20080269105 and in Examples 164-166 below as FIG. Q1) is a graph showing pH triggered release of risperidone from CYSC 2A.

FIG. 26 (which is referred to in the published Application 20080269105 and in Example 167 below as FIG. Q2) is a graph showing pH triggered release of risperidone from CYSC 20A.

FIG. 27 (which is referred to in the published Application 20080269105 and in Examples 168-173 below as FIG. R1) is a graph showing pH triggered release of Leuprorelin from CYSC #20.

FIG. 28 (which is referred to in the published Application 20080269105 and in Examples 174-179 below as FIG. S1) is a graph showing release of paravastatin from CYSC polymers.

FIG. 29 (which is referred to in the published Application 20080269105 and in Examples 180-181 below as FIG. T1) is a graph showing release of dexamethasone from CYSC polymers.

FIG. 30 (which is referred to in the published Application 20080269105 and in Examples 182-188 below as FIG. T2) is a graph showing release of dexamethasone from CYSC polymers.

FIG. 31 (which is referred to in the published Application 20080269105 and in Examples 189-196 below as FIG. Ex21A-40A) shows release of diclofenac from C12A polymers 1A-20A.

FIG. 32 (which is referred to in the published Application 20080269105 and in Examples 197-207 below as FIG. Ex 41A-51A) shows release of diclofenac from commercial polymers.

FIG. 41 which is referred to in the published Application 20080269105 as FIG. AP1 shows the chemical structure of CYSC polymers (R=H or $CH_3$, n≥12, m≥2).

FIG. 42 (which is referred to in the published Application 20080269105 as FIG. AP2) shows the structure of CYSC polymers (R=H or $CH_3$, n, n'≥12, m≥2).

FIG. 43 which is referred to in the published Application 20080269105 as FIG. AP3) shows the structure of CYSC polymers (R=H or CH$_3$, n≥12, m≥2).

FIG. 44 (which is referred to in the published Application 20080269105 as FIG. 213 A) shows group #1: Risperidone IV Control plasma concentration vs time.

FIG. 45 (which is referred to in the published Application 20080269105 as FIG. 213 B) shows group #2: Polymer #336-19-2 plasma concentration vs time.

FIG. 46 (which is referred to in the published Application 20080269105 as FIG. 213 C) shows group #3:336-19-4 plasma concentration vs time (two graphs showing different scales for clarity)

FIG. 47 (which is referred to in the published Application 20080269105 as FIG. 213 D) shows group #4: 336-19-3 plasma concentration vs time.

FIG. 48 (which is referred to in the published Application 20080269105 as FIG. 213E) shows group #5: 336-19-20 plasma concentration vs time (two graphs showing different scales for clarity).

FIG. 49 (which is referred to in the published Application 20080269105 as FIG. 213F) Group #6: Control Implant 336-20-2 and 336-20-20.

Figure 33:
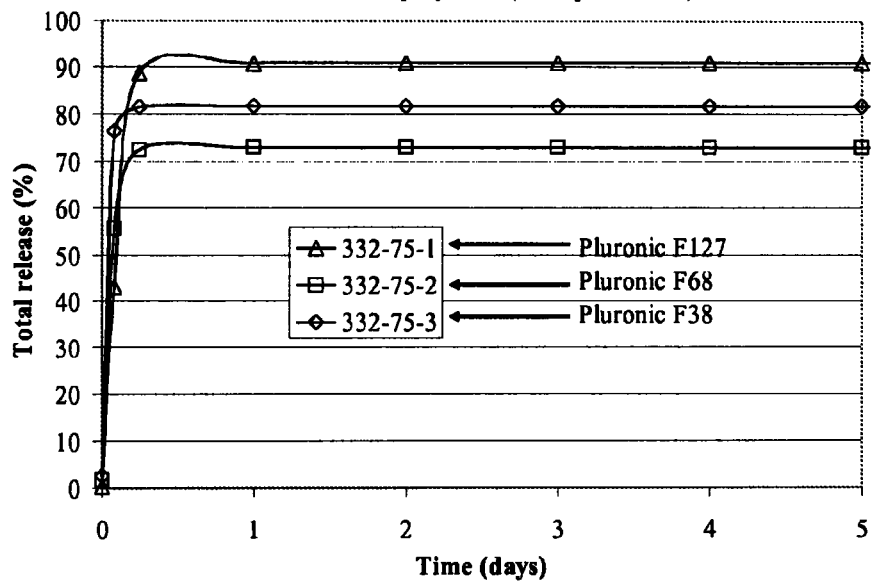
FIG. 33 (which is referred to in the published Application 20080269105 and in Examples 197-207 below as FIG. Ex 41 A-51b) shows release of risperidone from commercial polymers.
Figure 34:
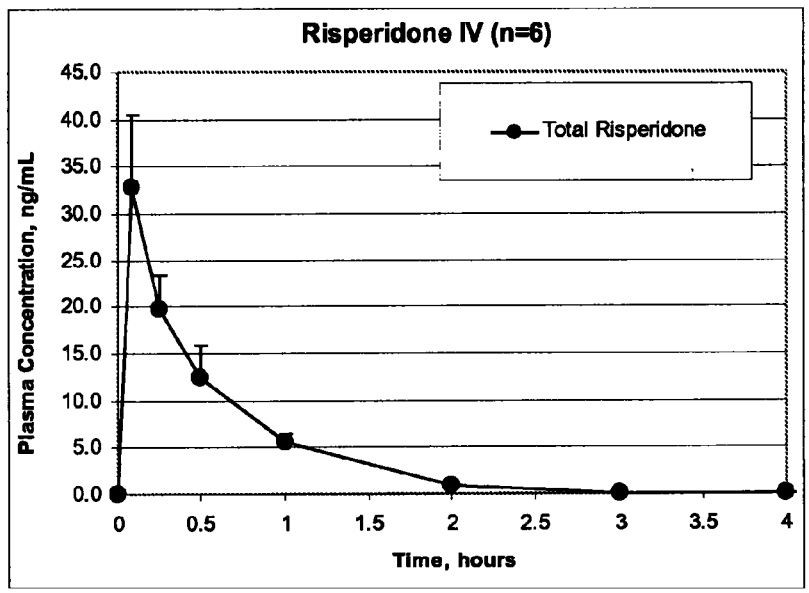
FIG. 34 (which is referred to in the published Application 20080269105 and in Examples 208-212 below as FIG. Y1) shows plasma concentration of Risperidone (control) vs time FIG. 35 (which is referred to in the published Application 20080269105 and in Examples 208-212 below as FIG. Y2) shows plasma concentration of risperidone vs time for Group #2: 336-19-2.
Figure 35:
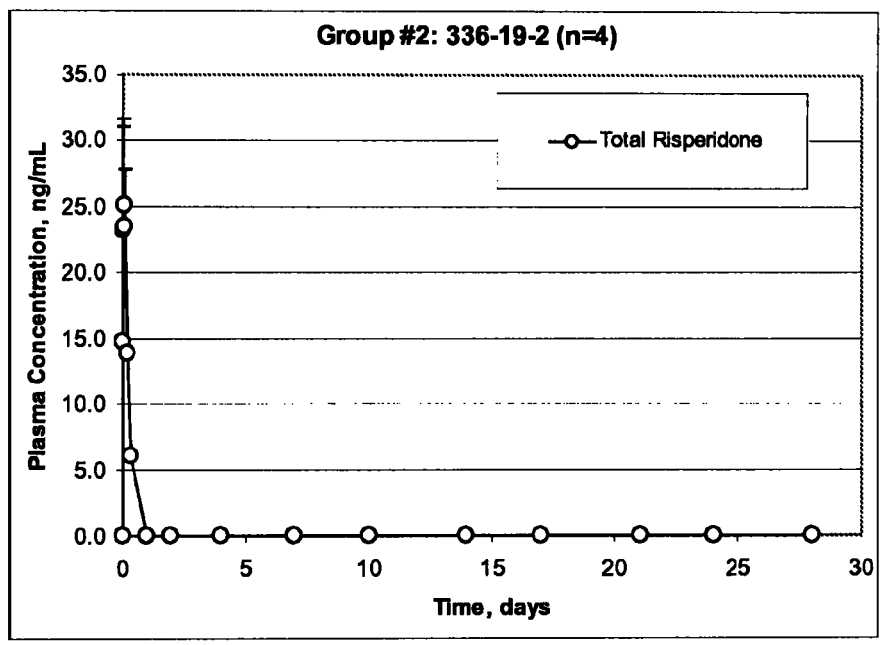
Figure 36:
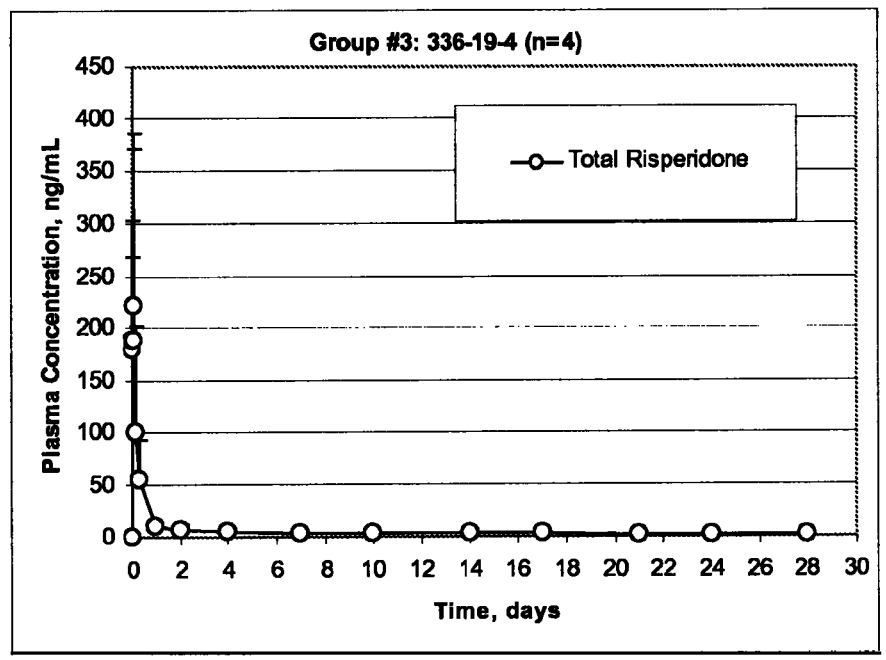
FIG. 36 (which is referred to in the published Application 20080269105 and in Examples 208-212 below as FIG. Y3a) shows plasma concentration of risperidone vs time for Group #3: 336-19-4.
Figure 37:
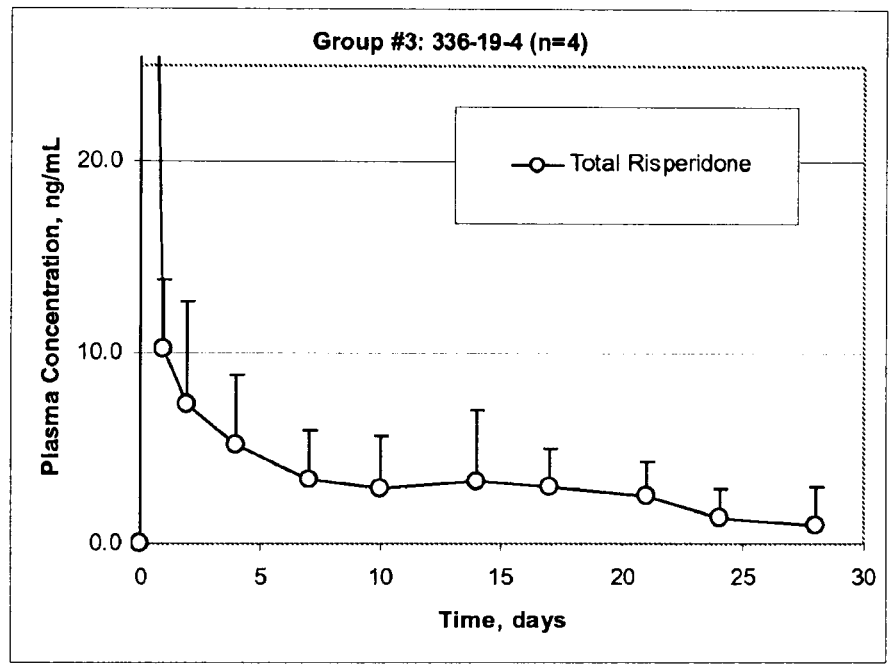
FIG. 37 (which is referred to in the published Application 20080269105 and in Examples 208-212 below as FIG. Y3b) shows plasma concentration of risperidone vs time for Group #3: 336-19-4 (different scale from FIG. Y3a).
Figure 38:
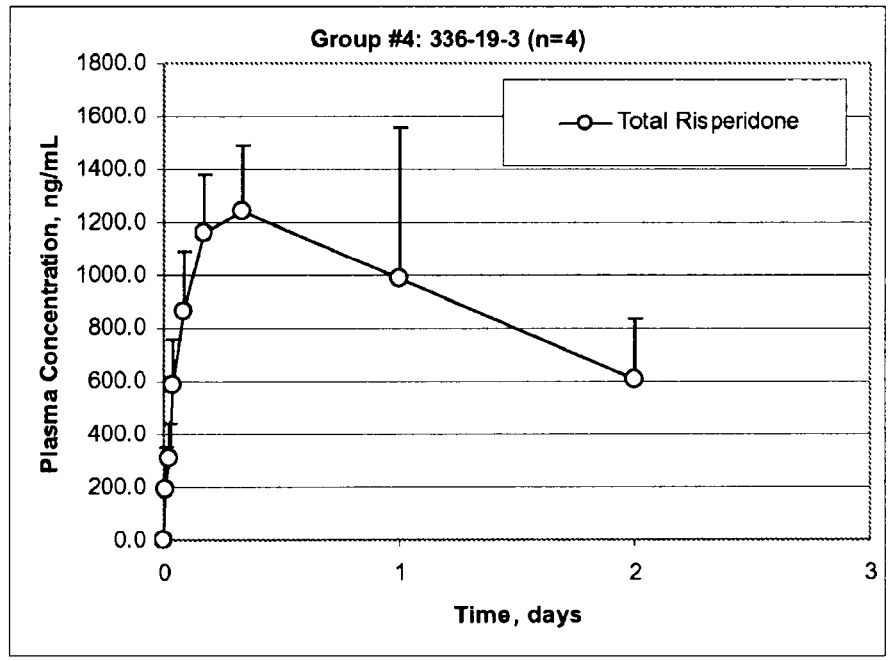
FIG. 38 (which is referred to in the published Application 20080269105 and in Examples 208-212 below as FIG. Y4) shows plasma concentration of risperidone vs time for Group #4: 336-19-4.
Figure 39:
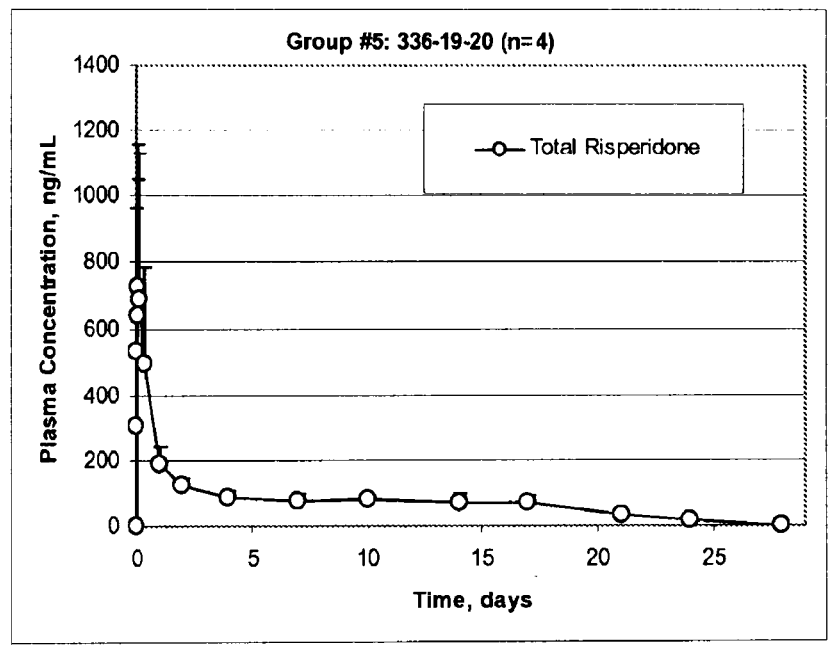
FIG. 39 (which is referred to in the published Application 20080269105 and in Examples 208-212 below as FIG. Y5a) shows plasma concentration of risperidone vs time for Group #5: 336-20-4.
Figure 40:
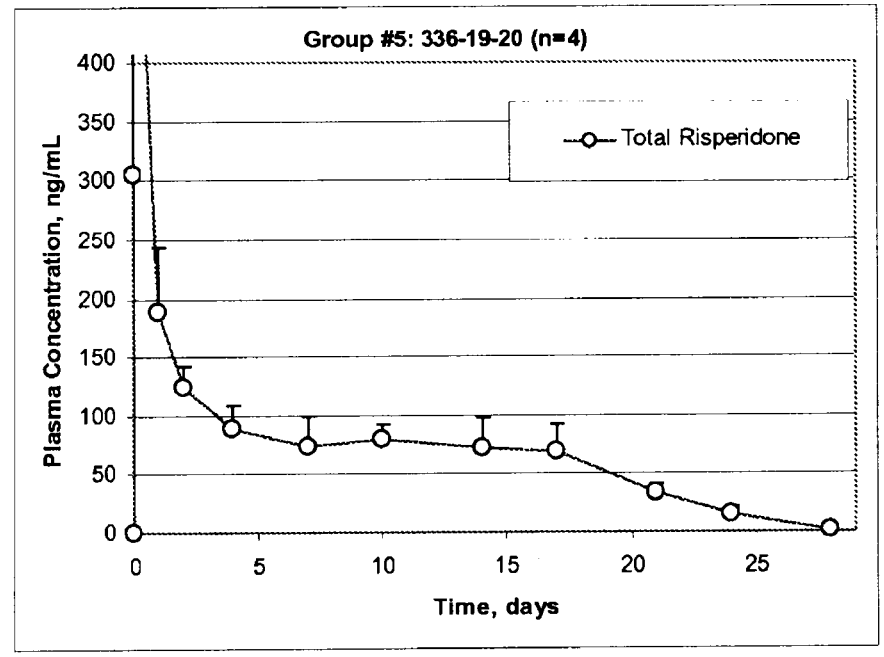
FIG. 40 (which is referred to in the published Application 20080269105 as FIG. Y5b) shows plasma concentration of risperidone vs time for Group #5: 336-19-20.

The table below shows the correlation between the Example numbers in Tables 1A, 1B and 1C and the Sample numbers referred to elsewhere in the specification.

| | Example No. | | | | | | |
|---|---|---|---|---|---|---|---|
| | 1A | 2A | 3A | 4A | 5A | 6A | 7A |
| Sample No. | 328-133-1 | 326-1-1 | 326-2-1 | 326-3-1 | 326-5-1 | 327-1-1A | 327-39-1 |
| | Example No. | | | | | | |
| | 8A | 9A | 10A | 11A | 12A | 13A | 14A |
| Sample No. | 327-40-1 | 326-8-1A | 326-8-3 | 327-3-1 B | 327-3-3 B | 327-137-1 | 327-137-3 |
| | Example No. | | | | | | |
| | 15A | 16A | 17A | 18A | 19A | 20A | |
| Sample No. | 326-6-1 | 326-6-3 | 326-9-1 | 326-11-3 | 327-42-2 | 327-42-11 | |

DETAILED DESCRIPTION OF THE INVENTION

Definitions

In this disclosure the following definitions are employed.

The terms "pharmaceutical formulation," "pharmaceutical composition," and "drug formulation" mean any composition which (i) is suitable for administration to a human being or other mammal or which can be treated, e.g. sterilized, to make it suitable for such administration, and (ii) comprises at least one drug and at least one CYSC polymer. In addition, a formulation may comprise additional, non-active components, such as pharmaceutical excipients, fillers, carrier materials etc that may be used to modify or improve the drug release, improve its physical and/or chemical stability, dosage form performance, processing, manufacturing, etc.

The terms "drug", "therapeutic", "therapeutic agent" or "drug" mean any drug which is biologically, physiologically, or pharmacologically active, in a human being or other mammal, locally and/or systemically, and includes diagnostic agents. Examples of drugs are described in well known literature references such as the Merck Index and the Physicians Desk Reference and they include, without limitation, medicaments; vitamins; mineral supplements; substances used for the treatment, prevention, diagnosis, cure or mitigation of a disease or illness; substances which affect the structure or the function of the body; pro-drugs, which become biologically active or more active after they have been placed in a physiological environment, biologically active metabolites of drugs which become biologically active or more active once they have been produced by the metabolism of a precursor chemical; Different types of drugs which may be used with the invention are discussed in more detail later in this application. Multiple drugs may be included in a single formulation. Drugs suitable for use in the present invention are for example disclose in column 11, line 16, to column 12, line 58, of U.S. Pat. No. 6,297,337, and in paragraph 0045 of US 2003/0224974, the entire disclosures of which are incorporated by reference herein for all purposes.

The term "mammal or cell" encompasses, but is not limited to, human beings and other mammals, and living tissue which is not part of a mammal.

The term "therapeutically effective amount" means an amount of a therapeutic agent, or a rate of delivery of a therapeutic agent, effective to facilitate a desired therapeutic effect. The precise desired therapeutic effect will vary according to the condition to be treated, the formulation to be administered, and a variety of other factors that are appreciated by those of ordinary skill in the art.

The term "diagnostic agent" means any chemical moiety that may be used for diagnosis or in a diagnostic test. For example, diagnostic agents include imaging agents containing radioisotopes, contrasting agents containing for example iodine, enzymes, fluorescent substances and the like.

The term "treatment" means the application of a process to an individual in order to alter a physiological state, whether or not the process includes a curative element.

As an indicator of the rate at which a drug will be released from a drug formulation in vivo, it is possible to make use of in vitro tests which are designed to mimic the expected physiological conditions in the delivery site or organ of interest (e.g. gastrointestinally for a pill or subcutaneously for an implant). In one example of such an in vitro test, the dosage form is placed in physiological buffered saline at a physiological pH and a physiologically relevant temperature, e.g. about 25° C. or 37° C.; preferably between 32° C. and 37 C. The amount of drug released and the time over which it is released in an in vitro test is no more than an indicator of in vivo results, but is useful for making comparative measurements.

"Controlled" release of a drug means release of the drug in a pre-determined or adjustable way such that the amount or rate or timing of release is pre-set or is altered in a desired way.

"Sustained" release of a drug means release over an extended period of time, for example minutes, hours or days, such that less than all the drug is released initially. A sustained release rate may provide, for example, a release of a certain specified amount of a drug from a dosage form, over a certain time period, under physiological conditions or in an in vitro test.

"Bolus" release means release of a large dose, for example all of a drug at one time or over a short period of time. Bolus release can be preceded or followed by sustained release.

The term "burst effect" as used in the context of drug delivery during administration of a drug means the release of drug from a dosage form as a bolus at higher than desired level or rate, typically, exceeding the therapeutically effective level. For example, a burst effect may be defined as the release of more than 50% of a drug from a dosage form under specific experimental conditions, such as when the dosage form is placed in physiological buffered saline at a set temperature such as at about 25° C. or 37° C. A burst is generally followed by a rapidly decreasing rate of release. A burst effect may be characterized by the release of a certain defined amount of a drug from a dosage form under specific conditions. For example, a burst effect may be defined as the release of a defined threshold amount of the total amount of loaded drug over a defined time under physiological conditions (in normal intended use, e.g. gastrointestinally for a pill or subcutaneously for an implant) or in a suitable in vitro test for example as described above or as described in the Examples below. For example, the threshold amount may be at least 20%, at least 30%, at least 40%, at least 50%, at least 60%, at least 70%, at least 80%, at least 90% or at least 95% of the total amount of drug loaded into the dosage form, and the defined time can be for example, 30 minutes, 1 hour, 2 hours, 3, hours, 6 hours, 8 hours, 10 hours, 12 hours, 16 hours, 20 hours, 24 hours, 36 hours, or 48 hours. A dosage form that does not display a significant burst effect may be a dosage form that, for example, releases less than 10% of the total amount of drug loaded into the dosage form over a 3 hour period following implantation. In certain embodiments of the invention the dosage form is pre-treated prior to implantation so that any burst effect is spent before implantation.

The terms "controlled release device", "controlled release dosage form" and similar terms mean any formulation or device wherein the release rate (e.g., rate of timing of release) of a drug or other desired substance contained therein is controlled by the device or dosage form itself and/or by the environment of use. Controlled drug delivery includes delivery of an amount of drug to a particular target site at a particular time, for example delivery of a bolus of drug to a tumor site.

The term "device" when used in the context of drug delivery, such as "drug delivery device" means any device that can deliver a drug, including pills, capsules, gels, depots, medical implantable devices (e.g., stents, including self-expanding stents, balloon-expandable stents, drug-eluting stents and stent-grafts, grafts (e.g., aortic grafts), artificial heart valves, cerebrospinal fluid shunts, pacemaker electrodes, endocardial leads, bioerodable implants and the like, and externally manipulated devices (e.g. drug devices and catheters, including catheters which can release a drug, e.g. as a result of heating the tip of the catheter).

The term "dosage form" means a composition which comprises a drug compounded or processed or presented in such a way that it is suitable for administration to a subject. A dosage form comprises a CYSC polymer and, a drug, and may also include one or more other additives, for example pharmaceutically acceptable excipients, carriers, penetration enhancers, stabilizers, buffers or other materials physically associated with the drug and/or the CYSC polymer to enhance the deliverability of the dosage form and/or the effectiveness of the drug. A dosage form may be administered, for example, as a liquid, a suspension, a solid such as a tablet, pill, capsule (including a microcapsule), emulsion, micelle, ointment, gel, emulsion, depot (including a subcutaneously implanted depot), or coating on an implanted device, e.g. a stent or the like. The dosage form can for example be applied externally, e.g. as a patch, or a device applied partly externally and partly implanted, or completely implanted or injected subcutaneously.

The terms "association", "associated" and the like mean any type of interaction, including chemical bonds (including, for example, covalent, ionic and hydrogen bonds) and/or Van der Waals forces, and/or polar and non-polar interaction through other physical constraints provided by molecular structure, and interactions through physical mixing.

"Patterned" or "temporal" as used in the context of drug delivery means delivery of drug in a pattern, generally a substantially regular pattern, over a pre-selected period of time (e.g., other than a period associated with, for example a bolus injection). "Patterned" or "temporal" drug delivery includes delivery of drug at an increasing, decreasing, substantially constant, or pulsatile, rate or range of rates (e.g., amount of drug per unit time, or volume of drug formulation for a unit time), and further includes delivery that is continuous or substantially continuous, or chronic.

The term "functionalized", as applied to a chemical compound, including a polymer, means that the compound has been treated so that it contains a functional moiety (i.e. a moiety which will undergo a further desired chemical reaction) which was not present on the compound before the treatment, or so that the polarity of the compound is changed, as evidenced, for example, by a change in the solubility parameter.

The term "alkyl" is used in this specification to include alkyl moieties which are straight chain alkyl moieties, branched chain alkyl moieties, cycloalkyl moieties, and moieties which consist essentially of two or more of straight chain alkyl, branched chain alkyl and cycloalkyl moieties.

In this specification, parts, ratios and percentages are by weight, except where otherwise noted. Temperatures are in degrees Centigrade (° C.). Molecular weights of polymers are in Daltons, are number average molecular weights (Mn) unless stated to be weight average molecular weights (Mw), and are measured by gel permeation chromatography (GPC) with a light scattering detection method, using a DAWN DSP laser photometer from Wyatt Technology. In defining the polymers, this specification uses the terms "melting point" (often abbreviated to Tp or Tm), "onset of melting temperature" (often abbreviated to To) and "heat of fusion" (which is a measure of crystallinity of the polymer, is expressed in J/g and is often abbreviated to ΔH). Tp, To and ΔH determined using a differential scanning calorimeter (hereinafter DSC), e.g. a Q 100 DSC from TA Instruments at a rate of temperature change of 110° C./min, e.g. from −10 to 150° C. Tp is the peak melting temperature, and To is the temperature at the intersection of the baseline of the DSC peak and the onset line, the onset line being defined as the tangent to the steepest part of the DSC curve below Tp. Unless otherwise stated, the values of Tp, To and ΔH are measured on the second heat cycle.

Bulk viscosities given herein are in centipoise and are measured using a Brookfield LVT viscometer with an electronically thermostat controlled thermal heater, controlled for example to 95° C., and small sample adapter using spindles 4 and 7.

Solubility parameters given herein were calculated using methods described in D. W. Van Krevelen "Properties of Polymer", Elsevier, 1997, 200-214, especially 214, and are expressed in units of $J^{1/2}/cm^{3/2}$.

This table below sets out other terms and abbreviations used in this specification, and the meanings to be attributed to them.

| Abbreviation | Meaning |
| --- | --- |
| C$x$ | a linear moiety containing x carbon atoms, optionally directly linked to each other. |
| C$x$A | an n-alkyl acrylate in which the n-alkyl group contains x carbon atoms, e.g. C16A is hexadecyl acrylate. |
| C$x$MA | an n-alkyl methacrylate in which the n-alkyl group contains x carbon atoms, e.g. C16MA is hexadecyl methacrylate. |
| (meth)acrylate | an acrylate or methacrylate |
| (meth)acrylic acid | acrylic acid or methacrylic acid |
| AA | Acrylic acid |
| MA | Methacrylic acid |
| MiBK | Methyl isobutyl ketone |
| AIBN | Azobisisobutyronitrile |
| DMAEA | dimethylaminoethyl acrylate |
| DMAEMA | dimethylaminoethyl methacrylate |
| PEG6A | $CH_2=CH-CO-O-(CH_2CH_2O)_6H$ |
| PEG6MA | $CH_2=C(CH_3)-CO-O-(CH_2CH_2O)_5CH_2CH_2OH$ |
| PEG6-OCH3MA | $CH_2=C(CH_3)-CO-O-(CH_2CH_2O)_5CH_2CH_2OCH_3$ |
| PEG9-OCH3MA | $CH_2=C(CH_3)-CO-O-(CH_2CH_2O)_8CH_2CH_2OCH_3$ |
| PEG12-OCH3MA | $CH_2=C(CH_3)-CO-O-(CH_2CH_2O)_{11}CH_2CH_2OCH_3$ |
| PEG23-OCH3MA | $CH_2=C(CH_3)-CO-O-(CH_2CH_2O)_{22}CH_2CH_2OCH_3$ |
| PEG25-OCH3MA | $CH_2=C(CH_3)-CO-O-(CH_2CH_2O)_{24}CH_2CH_2OCH_3$ |
| PEG46-OCH3MA | $CH_2=C(CH_3)-CO-O-(CH_2CH_2O)_{45}CH_2CH_2OCH_3$ |
| PPG6-OHMA | $CH_2=C(CH_3)-C)-O-(CH_2CH(CH_3)O)_6H$ |
| PEG25 C22MA | $CH_2=C(CH_3)-C)-O-(CH_2CH(CH_3)O)_6C_{22}H_{45}$ |
| IPA | isopropyl alcohol |
| EtAc | ethyl acetate |
| NMP | N-methyl pyrrolidone |
| BMP | butyl-3-mercapto propionate |
| Miglyol | Miglyol 812, a triglyceride with a mixture of C8 and C10 |
| Triganox | Triganox 428 -- t-butyl peroxy-3,5,5-trimethyl hexanoate |
| Dexa | Dexamethasone, which has a solubility parameter of 20.85 (9-fluoro-11β,17,21-trihydroxy-16a-methylpregna-1,4-diene-3,20-dione) |
| Prav | Pravachol, which has a solubility parameter of 21.07, (3,5-dihydroxy-7-[6-hydroxy-2-methyl-8-(2-methylbutanoyloxy)-1,2,6,7,8,8a-hexahydronaphthalen-1-yl]-heptanoic acid) |
| Risp | Risperidone, which has a solubility parameter of 17.48, (4-[2-[4-(6-fluorobenzo[d]isoxazol-3-yl)-1-piperidyl]ethyl]-3-methyl-2,6-diazabicyclo[4.4.0]deca-1,3-dien-5-one) |
| Dcl | Diclofenac sodium, which has a solubility parameter of 23.4, (2-[2-(2,6-dichlorophenyl)aminophenyl]ethanoic acid) |
| Tacro | Tacrolimus, which has a solubility parameter of 19.32, (3S-[3R*[E(1S*,3S*,4S*)],4S*,5R*,8S*,9E,12R*,14R*,15S*,16R*,18S*,19S*,26aR*]]-5,6,8,11,12,13,14,15,16,17,18,19,24,25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c] [1,4] oxaazacyclotricosine-1,7,20,21(4H,23H)-tetrone, monohydrate) |
| Leu | Leuprolide, which has a solubility parameter of 21.03, (N-[1-[[1-[[1-[[1-[[1-[[1-[[5-(diaminomethylideneamino)-1-[2-(ethylcarbamoyl)pyrrolidin-1-yl]-1-oxo-pentan-2-yl]carbamoyl]-3-methyl-butyl]carbamoyl]-3-methyl-butyl]carbamoyl]-2-(4-hydroxyphenyl)ethyl]carbamoyl]-2-hydroxy-ethyl]carbamoyl]-2-(1H-indol-3-yl)ethyl]carbamoyl]-2-(3H-imidazol-4-yl)ethyl]-5-oxo-pyrrolidine-2-carboxamide) |

General Representations Concerning the Disclosure

In this specification, reference is made to particular features of the invention (including for example components, ingredients, elements, devices, apparatus, systems, groups, ranges, method steps, test results, etc). It is to be understood that the disclosure of the invention in this specification includes all appropriate combinations of such particular features. For example, where a particular feature is disclosed in the context of a particular embodiment or a particular claim, that feature can also be used, to the extent appropriate, in the context of other particular embodiments and claims, and in the invention generally.

The embodiments disclosed in this specification are exemplary and do not limit the invention. Other embodiments can be utilized and changes can be made.

As used in this specification, the singular forms "a", "an", and "the" include plural reference unless the context clearly dictates otherwise. Thus, for example, a reference to "a part" includes a plurality of such parts, and so forth.

The term "comprises" and grammatical equivalents thereof are used in this specification to mean that, in addition to the features specifically identified, other features are optionally present. For example, a composition "comprising" (or "which comprises") ingredients A, B and C can contain only ingredients A, B and C, or can contain not only ingredients A, B and C but also one or more other ingredients. The term "consisting essentially of" and grammatical equivalents thereof is used herein to mean that, in addition to the features specifically identified, other features may be present which do not materially alter the claimed invention. The term "at least" followed by a number is used herein to denote the start of a range beginning with that number (which may be a range having an upper limit or no upper limit, depending on the variable being defined). For example "at least 1" means 1 or more than 1, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)", this means a range whose lower limit is the first number and whose upper limit is the second number. For example, "from 8 to 20 carbon atoms" or "8-20 carbon atoms" means a range whose lower limit is 8 carbon atoms, and whose upper limit is 20 carbon atoms. The terms "plural", "multiple", "plurality" and "multiplicity" are used herein to denote two or more than two features.

Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). Where reference is made herein to "first" and "second" features, this is generally done for identification purposes; unless the context requires otherwise, the first and second features can be the same or different, and reference to a first feature does not mean that a second feature is necessarily present (though it may be present). Where reference is made herein to "a" or "an" feature, this includes the possibility that there are two or more such features (except where the context excludes that possibility). For example, a composition which comprises a CYSC polymer and a drug, the composition can comprise two or more CYSC polymers and/or two or more drugs. Where reference is made herein to two or more features, this includes the possibility that the two or more features are replaced by a lesser number or greater number of features providing the same function (except where the context excludes that possibility). The numbers given herein should be construed with the latitude appropriate to their context and expression; for example, each number is subject to variation which depends on the accuracy with which it can be measured by methods conventionally used by those skilled in the art.

This specification incorporates by reference all documents referred to herein and all documents filed concurrently with this specification or filed previously in connection with this application, including but not limited to such documents which are open to public inspection with this specification.

CYSC Polymers b Moieties b is a bond or a divalent moiety linking the Cy moiety to an intermediate point on the polymer backbone all to a terminal moiety. Thus, b may for example be a covalent bond, or a divalent organic moiety (e.g. an aliphatic, aromatic or mixed aliphatic/aromatic moiety) or inorganic moiety. Examples of b moieties include ester, carbonyl, amide, amine oxide, hydrocarbon (for example phenylene), amino, ether, polyoxyalkylene, or an ionic salt linkage (for example a carboxyalkyl ammonium, sulfonium or phosphonium ion pair).

Cy Moieties

The Cy moieties (which provide side chains pendant from an intermediate location and/or from a terminal location of the polymer backbone) in a particular CYSC polymer may be the same or different. The Cy moieties must be such that they are capable of interacting with other Cy moieties, for example other Cy moieties elsewhere on the same polymer and/or on a different polymer (which may or may not be a CYSC polymer) and/or on a non-polymeric molecule, to provide crystallinity. The interaction between the Cy moieties is generally by way of hydrogen bonds or Van der Waals forces, and not via covalent or ionic bonding.

The Cy moieties can be of any kind, for example aliphatic, e.g. alkyl, or mixed aliphatic aromatic. The CYSC polymers contain moieties such that the polymer, when examined on a DSC in the manner defined below, has a heat of fusion of at least 5 J/g of a and an associated distinct melting temperature resulting from crystallization of the Cy moieties. Such polymers are known and have been referred to as side chain crystalline polymers (sometimes abbreviated to SCC polymers or SCCPs). Some SCC-polymers contain Cy moieties whose nature, amount and distribution are such that the polymer has a heat of fusion of at least 10, at least 20, at least 25, at least 30, at least 35, at least 40, or at least 45, for example 5-50 or 10-50, or 10-40 or 15-35 or 20-30, J/g.

Patents and other publications relating to SCC polymers include J. Poly. Sci. 60, 19 (1962); J. Poly. Sci, (Polymer Chemistry) 7, 3053 (1969), 9, 1835, 3349, 3351, 3367, 10, 1657, 3347, 18, 2197, 19, 1871; J. Poly. Sci, Poly-Physics Ed 18 2197 (1980); J. Poly. Sci, Macromol. Rev, 8, 117 (1974); Macromolecules 12, 94 (1979), 13, 12, 15, 18, 2141, 19, 611; JACS 75, 3326 (1953), 76; 6280; Polymer J 17, 991 (1985); and Poly. Sci USSR 21, 241 (1979); U.S. Pat. Nos. 4,830,855, 5,120,349, 5,129,180, 5,156,911, 5,254,354, 5,387,450, 5,412,035, 5,469,867, 5,665,822, 5,752,926, 5,783,302, 6,013,293, 6,060,540, 6,199,318, 6,210,724, 6,224,793, 6,255,367, 6,376,032, 6,492,462, 6,540,984, 6,548,132, 6,831,116, 6,989,417, and 7,101,928; and US Patent Application Publications Nos. 2001/0018484 2002/0090425 and 2002/0127305. The entire disclosure of each of those publications, patents and patent publications is incorporated herein by reference for all purposes.

The Cy moieties often comprise a linear carbon chain of at least 8 or at least 12 carbon atoms directly linked to each other, e.g. 12-50 or 16-30 carbon atoms. The moiety is generally not branched, but can be branched providing that the branching does not prevent the moiety from being capable of crystallization. Similarly, the moiety can be unsubstituted or substituted predominantly only by fluorine atoms, or can be substituted by other moiety which do not prevent the moiety from being capable of crystallization.

Cy can be for example a moiety comprising 6 to 50, e.g. 12 to 50, preferably 12 to 22 or 16 to 22, substantially linear carbon atoms, e.g. a moiety comprising at least 111 methylene moieties, for example 11-49 methylene moieties and a terminal methyl moiety, or a moiety comprising at least 5, e.g. 5 to 49 linear perfluoro or substantially perfluoro methylene moieties and a terminal perfluoromethyl moiety or hydrogen atom. Specific examples of suitable Cy moieties include C14, C16, C18, C20, C22, C30, C40 and C50, in particular n-alkyl moieties containing 14, 16, 18, 20, 22, 30, 40 and 50 carbon atoms, and partially or fully fluorinated n-alkyl groups containing at least 8 carbon atoms, and mixtures of Cy moieties having similar average chain lengths.

All the moieties of the formula —Y(b-Cy)-- in the CYSC polymer can be the same, or there can be a plurality of (i.e. two or more) different types of moiety which differ from each other in one or more of Y, b and Cy. In some CYSC polymers containing a plurality of different types of —Y(b-Cy)-- moiety, the different types are randomly distributed throughout the polymer. In other CYSC polymers, the different types are distributed in a desired non-random fashion in at least part of the polymer, such as in a block copolymer or a graft copolymer. For example, the polymer can comprise at least one polymer block which comprises only one type of repeating unit of the formula —Y($Rc_1$)- and a second polymer block which comprises only repeating units of the formula —Y($Rc_2$)-. Alternatively the polymer may comprise one or more sections which contain a plurality of —Y($Rc_1$)- and —Y($Rc_2$)- units distributed randomly, and at least one polymer block which comprises (i) only another type of repeating unit of the formula —Y(Rc)--, or (ii) a plurality of randomly distributed different repeating units of the formula —Y(Rc)--.

When there are two or more different Cy moieties, they may have, for example, an average length of 6 to 50 linear carbon atoms, the average being calculated by adding all lengths of all the Cy moieties in the polymer (or, in the case of a block, including graft, copolymer, all the Cy moieties in the block) and dividing by the number of Cy moieties. The average length may have, for example, an accuracy of +/−3%, +/−5%, or +/−10% or any amount therebetween.

Cy Moieties Containing Polyoxyalkylene Moieties

Some useful Cy moieties include polyoxyalkylene, e.g. polyoxyethylene, units. Such Cy moiety can for example be derived from alkoxy polyoxyalkylene(meth)acrylates, where the alkyl portion of the alkoxy group is preferably an alkyl, particularly an n-alkyl, group containing 12 to 50, preferably 12 to 22 carbons, and the polyoxyalkylene unit is a homopolymer, random copolymer, or block copolymer containing 2 to 100, e.g. 5 to 100, preferably 5 to 60, oxyalkylene units, preferably 2-20, e.g. 2-4, oxyalkylene units. Specific examples of such monomers include cetyl polyethoxylated methacrylate, stearyl polyethoxylated (meth)acrylate, behenyl polyethoxylated (meth)acrylate, lauryl polyethoxylated (meth)acrylate, cholesterol polyethoxylated (meth)acrylate and the like. The polyoxyalkylene unit can be attached to the alkyl side chain portion, as for example in hydroxypolyalkyleneoxyalkyl (meth)acrylates with similar alkyl and polyalkyleneoxy groups as above, e.g. hydroxypolyethleneoxystearyl acrylate, hydroxypolyethyleneoxycetyl methacrylate and the like.

Other Moieties Optionally Present in the CYSC Polymer

A CYSC polymer can consist essentially of the moieties of the formula —Y(Rc)-- or it can also contain other repeating units of a different type. Such other repeating units can be represented by the formula —Z(Rz)- where Z is a moiety forming part of the polymer backbone and Rz represents a monovalent moiety which is not an Rc moiety. All the repeating units of the formula —Z(Rz)- can be the same, or there can be a plurality of different types of repeating unit which differ from each other in Z, or in Rz, or in both Z and Rz. The moieties of the formula —Z(Rz)- can be randomly distributed throughout the polymer, or they can be distributed in a desired non-random fashion in at least part of the polymer.

The presence of Z(Rz) moieties in a CYSC polymer generally depresses the melting temperature and reduces the crystallinity of the CYSC polymer, to an extent which is dependent on the proportion and distribution of the Z(Rz) moieties and the nature of the Z(Rz) moieties. The Z(Rz) moieties also contribute to the chemical and other characteristics of the CYSC polymer, and their presence can be valuable for this purpose. For example, many useful CYSC polymers have an amphiphilic character, with the Cy moieties providing hydrophobic characteristics and the Rz moieties providing hydrophilic characteristics.

The Z(Rz) moieties in a CYSC polymers can be of any kind, for example aliphatic, e.g. alkyl, or mixed aliphatic aromatic. The Z(Rz) moieties can contain any suitable linking group through which they are linked to each other and to the Y(Rc) moieties. For example the CYSC polymer can comprise sections which comprise the Z(Rz) moieties and which are polyacrylate, polymethacrylate, polyalkyl methacrylate, poly-N-alkyl acrylamide, poly-alkyl oxazoline, poly-alkyl vinyl ether, poly-alkyl 1,2-epoxide, poly-alkyl glycidyl ether, poly-vinyl ester, poly-acrylamide, poly-methacrylamide, poly-maleimide, poly-_-olefin, poly-p-alkyl styrene, poly-alkyl vinyl ether, polyolefin, polyether, polyurethane, polysilane, polysiloxane, or poly(alkyl phosphazene).

All the Z(Rz) moieties can be the same, or there can be two or more different Z(Rz) moieties, randomly distributed and/ or arranged in a desired distribution, as for example in a block copolymer in which one of the blocks comprises essentially only one type of Z(Rz) moiety, and another of the blocks comprises essentially only another type of Z(Rz) moiety. The Z moieties (which, when there are two or more different types of Z moiety, can be the same or different) can for example be derived from the addition and/or condensation polymerization of suitable monomers, e.g. acrylic, methacrylic, olefinic, epoxy or vinyl monomers.

The bond between Z and Rz can may be any bond as described in the section discussing the bonds between Y and Rc. The bond may be hydrolytically stable, unstable, labile to hydrolysis or enzymatic cleavage.

Suitable monomers from which Z(Rz) moieties can be derived can contain the desired Rz moieties, and/or can contain Rz precursor moieties some or all of which are converted into Rz moieties during or after the polymerization. Suitable monomers are for example alkyl (e.g. 2-ethylhexyl, butyl, ethyl, methyl) (meth)acrylates, hydroxyalkyl (meth)acrylates (e.g. hydroxyethyl acrylate, hydroxyethyl methacrylate) alkoxyalkyl (meth)acrylates (e.g. methoxyethyl acrylate, ethoxyethyl methacrylate), and hydroxypolyoxyalkylene (meth)acrylates (e.g. —hydroxypolyoxyethylene methacrylate or acrylate where the ethyleneoxy units are from 4 to 50), other (meth)acrylates (e.g. glycidal methacrylate, (acetoacetoxy)ethyl methacrylate), acrylamides and methacrylamides; styrene; monoacrylic functional polystyrene; alkyl vinyl ethers, and alkyl vinyl esters; and in all of which monomers—the alkyl groups are alkyl groups which are not Rc moieties, for example n-alkyl moieties containing less than 12, e.g. 1, 2, 3, 4, 5, 6, 7, 8, 9, 10, 11, or 12 carbon atoms (e.g. vinyl laurate); and polar monomers, for example acrylic acid, methacrylic acid, itaconic acid, dimethylaminoethyl methacrylate, diethylaminoethyl methacrylate, t-butyl acrylamide, dimethylaminopropyl methacrylamide, N-isopropyl acrylamide, acrylonitrile, methacrylonitrile, maleic anhydride, monobutyl fumarate, vinyl acetate, N-vinyl pyrrolidone, and comonomers containing amine groups.

In certain embodiments Rz may comprise polyoxyalkylene e.g. polyoxyethylene, moieties, for example a polyoxyalkylene moiety which links the Z moiety to an end group which is not an Rc moiety Functional Rz Moieties The Rz moieties can for example include one or more desired functional groups, including, but not limited to, the functional groups forming part of the compounds listed below (the disclosure of those functional groups being independent of the moiety forming the remainder of the listed compound).

Useful Rz moieties include:

(1) Nitrogen-containing side chains, for example the moieties which result from the polymerization of the groups of monomers and specific monomers listed below. It is noted that the identified Rz moieties and/or the functional groups thereon can also be obtained through the use of other monomers: N,N-dialkyl amino (in particular, dimethylamino) (meth) acrylates; ammonium salt-containing (meth)acrylates, for example 2-trimethylammonium methylmethacrylate chloride, methacrylamidopropyl trimethylammonium chloride, N,N-(diethyl or dimethyl)aminoethyl(meth)acrylate methosulfate; N-vinylpyrrolidinone;

imides like the ring-closed reaction products of maleic or itaconic anhydride with primary amines; 2-methacryloxy-N-ethylmorpholine; n- or t-butylacrylamide; (meth)acrylamide; dimethylaminopropyl methacrylamide; 2-t-butylaminoethyl methacrylate; (meth)acrylonitrile; t-butylaminoethyl (meth) acrylate; acryloylmorpholine; N-(2-hydroxyethyl)acetamide; 1-piperidinoethyl (meth)acrylate; and amine oxide containing monomers obtained by reacting alkyl amine containing side chain containing monomers with an oxidizing agent to give an amine oxide of the precursor alkyl amine.

In certain specific embodiments, the formulations of the invention specifically exclude Rz side chains derived from N-vinylpyrrolidinone.

(2) Oxygen-containing side chains, for example the moieties which result from the polymerization of the groups of monomers and specific monomers listed below, including carboxyl- and sulfonic acid-containing monomers and salts thereof. It is noted that the identified Rz moieties and/or the functional groups thereon can also be obtained through the use of other monomers: acrylic acid, methacrylic acid; itaconic anhydride; itaconic acid; maleic anhydride; maleic acid; fumaric acid; monoesters and monoamides of fumaric acid, maleic acid, crotonic acid, and 2-acrylamido-2-methyl-propane sulfonic acid ("AMPs"); vinyl sulfonic acid; hydroxyalkyl (meth)acrylates, in particular, hydroxyethyl, hydroxypropyl, and hydroxybutyl) (meth)acrylates; tetrahydrofurfuryl (meth)acrylate; glycidyl methacrylate; alkoxyalkyl (meth)acrylates, e.g. methoxyethyl (meth)acrylate; hydroxycaprolactone acrylate; 1-acryloxy-2-hydroxy-3-phenoxypropane; methylol methacrylate; ethoxyethyl (meth) acrylate; 2-(2-ethoxyethoxy)ethylacrylate; acetoacetoxyethyl (meth)acrylate; phenoxyethyl (meth)acrylate; (meth) acrolein; alkoxy or hydroxyl(polyoxyalkylene)alkyl (meth) acrylates, e.g. methoxy- or hydroxypolyoxyethylene (meth) acrylates, for example those in which the moles of ethyleneoxy units are from 2 to 80, preferably 6 to 50; alkoxy- or hydroxypolyoxypropylene-polyoxyethylene alkyl (meth) acrylates, for example those in which the blocks of each oxyethylene and oxypropylene unit are present in 1/1 to 1/3 ratios whereby the amount of oxyalkylene units in each block is 5 to 100, preferably, 5 to 60 units.

(3) Fluorine-containing side chains, for example the moieties which result from the polymerization of the groups of monomers and specific monomers listed below. It is noted that the identified Rz moieties and/or the functional groups thereon can also be obtained through the use of other monomers: trifluoroethyl (meth)acrylate; heptadecafluorodecyl (meth) acrylate; octafluoropentyl (meth)acrylate; eicosafluoroundecyl (meth)acrylate; hexadecafluorononyl (meth)acrylate; and tetrahydroperfluorodecyl (meth)acrylate.

(4) Phosphorus-containing side chains, for example the moieties which result from the polymerization of the monomers listed below and similar monomers. It is noted that the identified Rz moieties and/or the functional groups thereon can also be obtained through the use of other monomers: 2-methacryloyloxyethyl phosphoryl choline; 2-acryloyloxypropyl phosphoryl choline; and stearyl fumaroylethyl phosphoryl choline.

(5) Silicon-containing side chains for example the moieties which result from the polymerization of the groups of monomers and specific monomers listed below. It is noted that the identified Rz moieties and/or the functional groups thereon can also be obtained through the use of other monomers: silyl monomers, e.g. trimethylsiloxy ethyl(meth)acrylate, 3-acryloxypropyl trimethoxysilane, and 3-acryloxypropyl tris(trimethylsiloxy)silane, monomethacryloxymonotrimethylsiloxyterminated polyethylene oxide, monomethacryloxypropyl alkyl polydimethylsiloxane where the alkyl group contains 1-8 carbon atoms, preferably 1 or 4 carbon atoms, and similar materials sold by for example Gelest as MCR-M17 and MCR-M11, and the like.

(6) Ligand groups which bind to target receptor sites. e.g., receptor proteins that are differentially over-expressed on target cells, for example cancerous cells. Ligands can be physically mixed as well as being part of the CYSC polymer. Ligands are discussed in detail later.

Hydrophilic Rz Moieties

Some CYSC polymers include Z(Rz) moieties in which at least some of the Rz moieties are hydrophilic, the CYSC polymer then being an amphiphilic copolymer having both hydrophobic and hydrophilic characteristics. Formulations comprising such amphiphilic polymers may form micelles or emulsions or liposomes in water, for example containing a hydrophobic drug within the hydrophobic core. It is often convenient to provide CYSC polymers with hydrophilic character by the inclusion of polyoxyethylene oxide units ("pegylation").

Hydrophobic Rz Moieties

Some CYSC polymers include Z(Rz) moieties in which all the Rz moieties are hydrophobic, in which case the CYSC polymer will be a copolymer having only hydrophobic characteristics.

Proportions of Z(Rz) Moieties

The CYSC polymer generally contains Z(Rz) moieties in amount less than 95%, particularly less than 70%, especially less than 100% or less than 50%, e.g. 5 to 25%, based on the weight of the polymer (e.g., 5, 7, 10, 15, 17, 20, 23 or 25%).

The influence of Z(Rz) moieties on the properties and preparation of formulations is further discussed below.

Proportions of Y(Rc) Moieties

A CYSC polymer can be a homopolymer or copolymer which consists of Y(Rc) moieties. However, many useful CYSC polymers contain less than 75%, or less than 50%, e.g. 1 to 75%, 5 to 50%, 15-50%, 15-30% or 10 to 25%, of Y(Rc) moieties, for example no more than 1%, 3%, 5%, 7%, 10%, 15%, 20%, 25%, 30%, 40% or 50% of Y(Rc) moieties. At the lower end of the Y(Rc) moiety content, in order to enhance crystallinity, the Rc moiety preferably contains at least 18 linear carbon atoms and/or the Y(Rc) moieties are present as grafted chains or blocks which consists essentially of the Y(Rc) moieties.

CYSC Polymer Backbones

The backbone of a CYSC polymer can be of any kind. Thus, the —Y— moieties, and the —Z— moieties if present, which can be the same as, or different from, the —Y— moieties, can for example comprise carbon atoms which are linked to each other directly by covalent bonds or through other elements or combinations of elements, and repeating units can be linked to each other directly by covalent bonds or can contain linking units comprising one or more atoms e.g ester (including orthoester), amide, ether or phosphate linkages. For example, the CYSC polymer can be, or can comprise sections which are, polyacrylate, poly-alkyl acrylates, poly-fluoroacrylate, polymethacrylate, polyalkyl methacrylate, poly-N-alkyl methacrylamide, poly-alkyl oxazoline, poly-alkyl vinyl ether, poly-alkyl 1,2-epoxide, poly-alkyl glycidyl ether, poly-vinyl ester, poly-acrylamide, poly-methacrylamide, poly-maleimide, poly-α-olefin, poly-p-alkyl styrene, poly-alkyl vinyl ether, polyolefin, polyether, polyurethane, polysilane, polysiloxane, or poly(alkyl phosphazene). The CYSC polymer can, for example, be derived from the addition and/or condensation polymerization of suitable monomers, e.g. acrylic, methacrylic, olefinic, epoxy, vinyl or silicon-containing monomers.

Melting Behavior of CYSC Polymers

Generally, the melting temperature (Tp) of a CYSC polymer is primarily dependent on the number of carbon atoms directly linked to each other in a straight chain in the Cy moiety(s). Unlike most other crystalline polymers, whose crystallinity depends upon crystallization of the polymer backbone), CYSC polymers show relatively little change in melting temperature with changing molecular weight. Other things being equal, the greater the linear length of the Cy moiety, the higher the melting temperature. For example, the homopolymers of n-alkyl acrylates in which the n-alkyl group contains 14, 16, 18, 22, 30, 40 and 50 carbon atoms have melting temperatures of about 20, 36, 49, 60, 71, 76, 96 and 102° C. respectively. The homopolymers of the corresponding n-alkyl methacrylates have melting temperatures of about 10, 26, 39, 50, 62, 68, 91 and 95° C. respectively. The CYSC polymers used in this invention often have a melting temperature of 22 to 70° C., or 35 to 50° C., or 38 to 50° C., e.g. 37° C. to 42° C. or 40° C. to 47° C. However, CYSC polymers with melting temperatures below 22° C., for example as low as 2° C., or higher than 70° C. may be useful in certain embodiments.

The melting temperatures of copolymers consisting of two or more Y(Rc) moieties reflects the relative proportions of the different Y(Rc) moieties. The presence of Z(Rz) moieties generally reduces the melting temperature and broadens the melting range.

Random copolymers of the long linear chain n-alkyl acrylates and methacrylates generally have intermediate melting temperatures in the range of 0 to 85° C. dependent on the length of the n-alkyl chain Random copolymers with other monomers, e.g. acrylic acid or butyl acrylate, typically have somewhat lower melting temperatures. Longer chain Z(Rz) comonomers exert greater influence on Tm depression than shorter chain Z(Rz) comonomers since the longer chain monomers have greater potential to disrupt the side chain crystalline domains.

In CYSC polymers containing relatively small amounts of Cy moieties, the extent of crystallinity can be enhanced by incorporating those moieties in blocks or grafts.

The heat of fusion of a polymer reflects the extent of its crystallinity. As a general rule, and other things being equal, the greater the proportion (if any) of Z(Rz) moieties, the lower the heat of fusion of a CYSC polymer. In a CYSC polymer containing particular proportions of particular Y(Rc) and Z(Rz) moieties, the heat of fusion will generally be greater if at least some of the Y(Rc) moieties are adjacent to each other. For example, a random copolymer containing Y(Rc) and Z(Rz) moieties will have less crystallinity (and therefore a lower heat of fusion) than (i) a block copolymer containing first blocks containing substantially all the Y(Rc) Moieties and second blocks containing substantially all the Z(Rz) moieties, or (ii) a graft copolymer in which the grafted chains consist essentially of all the Y(Rc) moieties.

The sharpness of the melting of the CYSC polymers can be quantified by reference to the value of Tp−To. For example, the CYSC polymer can have a Tp−To<$Tp^{0.7}$, e.g. <$Tp^{0.6}$, e.g. less than 15° C. or less than 10° C. or less than 5° C. Thus, for a Tp of 40° C., Tp−To can for example be less than 13.2, e.g. less than 9.1. This narrow melting range can be very valuable particularly in combination with the ability to control molecular weight substantially independently of Tp, and the ability to select a CYSC polymer having a Tp close to in vivo temperatures. For example, it can facilitate mixing of a CYSC polymer with a drug at temperatures which do not degrade the drug.

Compared to polymers whose crystallinity results from crystallization of the main polymer backbone, the Tp of CYSC polymers is relatively little influenced by the molecular weight of the polymer. It is, therefore, possible, by selection of the repeating units of the polymer, to make CYSC polymers which melt at a desired temperature (e.g. from 2 to 105° C.) and over a relatively narrow temperature range, and which have a desired molecular weight. In addition, as further explained below, CYSC polymers can be designed to have desired chemical and physical properties. As a result, CYSC polymers provide important benefits for loading and delivery of drugs and other drugs. These benefits include for example the ability to make formulations at desired temperatures, in particular at temperatures which do not have any substantial adverse effect on the drug, and the ability to provide formulations having desired properties such as viscosity, adhesion, hydrophobicity, hydrophilicity, volume control, and permeability, loading and rate and/or pattern of release.

In many cases, the CYSC polymers used in the invention do not have any crystallinity which results from crystallization of the polymer backbone ("main chain crystallinity"). However, in some embodiments of the invention, the CYSC polymer is a polymer obtained by modifying a main chain crystalline polymer to introduce Rc moieties at intermediate and/or terminal points on the polymer.

Types of CYSC Polymer.

The CYSC polymer can for example be a random copolymer, graft copolymer or block copolymer (including a thermoplastic elastomer), or core-shell polymer. Non-exclusive examples are as follows.

(a) The polymer comprises one or more types of —Y(Rc)- moiety and one or more types of —Z(Rz)- moiety, all the moieties being randomly distributed.

(b) The polymer is a block copolymer comprising (i) polymer blocks consisting essentially of one or more —Z(Rz)- moieties, and (ii) polymer blocks which comprise one or more types of repeating unit of the formula —Y(Rc)-, and optionally one or more types of repeating units of the formula —Z(Rz)-.

(c) The polymer can be a graft polymer, for example (i) a polymer comprising a backbone which comprises, or consists essentially of, one or more —Y(Rc)- moieties, and grafted side chains each of which comprises, or consists essentially of, one or more —Z(Rz)- moieties, or (ii) a polymer comprising a backbone which comprises, or consists essentially of, one or more —Z(Rz)- moieties, and grafted side chains each of which comprises, or consists essentially of, one or more —Y(Rc)- moieties.

CYSC polymers which can be used in this invention include atactic, syndiotactic and isotactic polymers of n-alkyl α-olefins (e.g. the atactic and isotactic polymers of C16 olefin, having Tp's of 30° and 60° C. respectively); polymers of n-alkylglycidyl ethers (e.g. the polymer of C18 alkyl glycidylether); polymers of n-alkyl vinyl ethers (e.g. the polymer of C18 alkylvinylether having a Tp of 55° C.); polymers of n-alkyl-α-epoxides (e.g. the polymer of the C18 alkyl α-epoxide having a Tp of 60° C.); polymers of n-alkyl oxycarbonylamido-ethylmethacrylates (e.g. the polymers of C18 IEMA, C22 IEMA and C30 IEMA, having Tp's of 56° C., 75° C. and 79° C. respectively); polymers of n-fluoro alkyl acrylates (e.g. the polymer of C8 hexadecafluoroalkylacrylate and the polymer of a mixture of C8-12 alkyl fluoroacrylates, having Tp's of 74° C. and 88° C. respectively), polymers of n-alkyloxazolines (e.g. the polymer of C16 alkyl oxazoline having a Tp of 155° C.); polymers obtained by reacting an hydroxyalkyl acrylate or methacrylate with an alkyl isocyanate (e.g. the polymers obtained by reacting hydroxyethyl acrylate with C18 or C22 alkyl isocyanate and having Tp's of 78° and 85° respectively); and polymers obtained by reacting a difunctional isocyanate, a hydroxyalkyl acrylate or methacrylate, and a primary fatty alcohol (e.g. the polymers obtained by reacting hexamethylene diisocyanate, 2-hydroxyethyl acrylate, and C18 or C22 alcohols, and having Tps of 103° and 106° C. respectively), as well as the acrylate or methacrylate polymers formed from copolymers of very long chain mixtures of aliphatic alcohols like the Unilin alcohols sold by Baker Petrolite averaging C30 or C40 or C50 carbon atoms, which can be converted to (meth)acrylate monomers and polymerized to homopolymers melting about 80, 90 or 100° C. respectively.

The Cy moieties in the CYSC polymers form crystalline aggregates by overlap of the Cy moieties with other Cy moieties in the same molecule or in a different molecule which may or may not be part of a CYSC polymer leading to intermolecular aggregates or domains of crystalline regions. The greater the overlap, the stronger the crystalline aggregate.

Molecular Weight of the CYSC Polymer

The molecular weight of the CYSC polymer can influence the incorporation and/or retention and/or delivery of a drug associated with the polymer. The Mn of the CYSC polymer can for example be 500 to 1,000,000, e.g. 1,000 to 50,000, 2000 to 40,000, 2000 to 25,000, 2000 to 30,000, or 3000 to 20,000 daltons. In some cases it is preferred to use a CYSC polymer having an average molecular weight (Mn) of less than 200,000, or less than 100,000, or less than 50,000, or less than 30,000, or less than 25,000, or less than 20,000, or less than 10,000, or less than 5000, or less than 2500, or less than 1000 daltons, e.g. 1,000 to 20,000, all 1,000 to 10,000 or 2,000 to 20,000, or 3,000 to 5,000 daltons. In other cases, it may be appropriate to use CYSC polymers with a molecular weight greater than 1,000,000 daltons. It some cases, e.g., with a hydrogel, an infinite molecular weight is desired. The molecular weight of the CYSC polymer moiety can be adjusted (for example through choice of the reaction conditions and addition of chain transfer agents), for example so as to optimize the reactivity of attached functional moieties without substantial change in Tp. Moreover, the ability to control the molecular weight of these polymers can assist in the mixing and processing of the formulations. In addition, in some cases, crosslinked gel and crosslinked solid CYSC polymers are desired, essentially, having an infinite molecular weight. Sometimes, it may be beneficial to have a gel which in its 100% form is a powder which can be mixed in the appropriate solvent with a drug to give the formulation. In other cases, such as transdermal applications, it may be beneficial to have a low molecular weight.

In some cases it is preferable that the CYSC materials used for the administration of drugs to mammals should be nonabsorbable or essentially nonabsorbable in the patient's body. This is so both for implanted applications and ingested formulations. The polymers as used by the invention are substantially physiologically inactive. For example, polymers which are of high molecular weight, e.g., Mn greater than 10,000 Daltons, charged or crosslinked polymers or polymers which are insoluble under physiological conditions, eliminate or significantly reduce transportation of the polymer across a cell membrane or gut wall. Thus in some embodiments, the CYSC polymers (or their break-down products have a molecular weight of below 20,000, or below 15,000 or more preferably below 10,000 Daltons and are not charged or crosslinked, and are thus voidable from the body.

Solubility Parameters of the CYSC Polymer

The solubility parameters of the polymer or various blocks or grafts within the copolymer can influence the solubility of a particular drug in the polymer, thereby, for example, improving the CYSC polymer's capacity and effectiveness as a drug reservoir. For example, solubility parameter estimations can be found in the book by D. W. Van Krevelan entitled "Properties of Polymers" Elsevier. 2003. As examples, the Log P of the hydrophobic crystalline side chain polymers (wherein Log P=Log of partition coefficient between organic and aqueous phases.) and the pKa (wherein pKa=dissociation constant of the acid or the base) of an amphiphilic crystalline side chain polymers are important in addition to the Tm of the solvated or hydrated CYSC polymers. The partition coefficient, P, and pKa may be used to estimate distribution of drugs, particularly in biological applications. The Log P and pKa assists in addressing CNS (central nervous system) penetration, oral absorption, intestinal absorption, colonic absorption, sub-lingual absorption, and percutaneous absorption, in addition to helping to optimise the physical form and composition of the drug formulation. Understanding the Log P, the pKa, and the Tm properties assists the selection of hydrophobic and hydrophilic groupings for the CYSC polymer to assist mixing with the drug for drug formulations. Also, these properties assist selection of the appropriate solvents if solvents are used in mixing of the CYSC polymer with the drug.

Some embodiments of the invention are summarized by the following statements.

A. A pharmaceutical formulation which comprises a drug and a CYSC homopolymer or copolymer and which has one or more of the following characteristics:—

(a) the formulation contains at least 5% or at least 10%, e.g. 5 to 30%, by weight of the drug;

(b) the drug is associated with the polymer by one or more bonds selected from electrostatic bonds, hydrogen bonds, covalent bonds, or by entropic forces;

B. A method of using a pharmaceutical formulation according to Statement A wherein the drug is released in a controlled manner.

The method of Statement B optionally has one or more of the following characteristics.

(a) the drug is released over an extended period of time; and (b) no more than 80%, preferably no more than 50%, for example no more than 30%, of the total drug loaded into the formulation is released from the formulation over a period of time of 6 hours following administration of the formulation to a subject;

(c) less than 50%, or less than 10%, of the total drug loaded into the formulation is released over a period of time of 1 hour, or over a period of time of two hours, following administration of the formulation to a subject, (d) at least 75% of the total drug loaded into the formulation is released within 30 minutes of activation of the formulation;

(e) the drug is released from the formulation by one or more of the following changes in condition
  (i) heating the formulation,
  (ii) hydration of the formulation,
  (iii) exposing of the formulation to an enzyme,
  (iv) changing the pH of the environment surrounding the formulation.

In certain embodiments, the formulation of the invention specifically excludes certain features, for example, in certain embodiments the polymer does not possess main chain crystallinity, or the polymer is not a block co-polymer and is not a graft co-polymer, or the polymer is not a hydrogel, or the polymer is hydrolytically stable, or the polymer is not an anhydride, or the polymer does not contain the structure Ra—CO—O—CO—Rb where Ra and Rb may be any moiety.

Elimination of Straight-Chain Aliphatic Hydrocarbons from the Body

If ingested into the gut, straight chain (aliphatic) hydrocarbons (such as medicinal grade mineral oil) are eliminated from the body in the feces. If they are absorbed or introduced into the circulatory system, as with petroleum hydrocarbons, the polymeric compounds of the invention are lipophilic. Therefore, they would tend to distribute in fatty tissue (Rozman and Klaassen (1996) *Absorption, distribution, and excretion of toxicants*. In: Klaassen, C. D., ed. Casarett & Doull's Toxicology: The Basic Science of Poisons, Fifth Edition. New York, N.Y.: Macmillan Publishing Company, pp 91-112.) and in lymph nodes (Kleinau S., Dencker, L. and Klareskog, L. (1995) *Oil-induced arthritis in da rats. Tissue distribution of arthritogenic* 14C-*labelled hexadecane* Int. J. Immunopharmacol. 17(5): 393-397), and may finally be excreted according to their lipid solubility in the blood and urine.

Preparation of CYSC Polymers

The CYSC polymers can be prepared in any way, for example using techniques which are well-known to those skilled in the art, e.g. emulsion, solution, bulk and suspension polymerization techniques using conventional catalysts. Conventional additives and catalysts can be employed to achieve desired molecular weights, for example azo and peroxide catalysts, thiol chain transfer agents (e.g. alkyl mercaptans, hydroxyethyl mercaptan, butyl mercaptopropionate and mercapto acetic acid), or allyl chain transfer agents or regulators (e.g. including alpha-methyl styrene). The type of polymerisation can often be selected according to the form of CYSC formulation to be administered. For example, if a micelle or emulsion form is desired, emulsion polymerisation, optionally in the presence of the drug, can be employed; if a hydrogel form is preferred, polymerisation under aqueous or emulsion conditions can be employed; and if a spray-dried form is preferred, polymerisation under solvent conditions can be used.

Methods of preparing graft copolymers s include preparing a preformed polymer comprising Y(Rc) moieties and optionally Z(Rz) moieties, and then grafting suitable monomers (which may contain Rc and/or Rz moieties) at reactive sites at the end or in the middle of the preformed polymer. Methods of preparing block copolymers include preparing two or more preformed polymers, at least one of the preformed polymers comprising Y(Rc) moieties and optionally Z(Rz) moieties, and at least one of the other preformed polymer(s) comprising Z(Rz) moieties, each of the preformed polymers having at least one reactive site at an end of, or between the ends of, the preformed polymer, and then reacting the preformed polymers to form the desired CYSC polymer.

For example, in a CYSC polymer may be prepared by copolymerising a vinyl type macromonomer with other monomers, or by making a CYSC polymer, and then reacting the functionalized polymer with the second block material, for example a urethane block, or an epoxy block, a polyether block, a polyester block, a polyethyleneoxide, polypropyleneoxide or polytetramethyleneoxide block, a polysiloxane block, or a poly(alkyl or alkoxy)silane block.

In certain embodiments, the CYSC polymers used in the formulations of the invention are specifically not cross-linked. In certain embodiments, such as hydrogel formulations, however, they may be cross-linked.

When a cross-linked CYSC polymer is desired, the monomer starting material can include a cross-linking monomer, for example to control crosslink density in a hydrogel. Crosslinking monomers or crosslinking reactants can be added at various times during the process including (a) when preparing the polymer in a desired shape followed later by the addition of therapeutic drug or (b) after separately preparing polymer, combining such polymer with therapeutic drug and then finally adding a crosslinking agent to set into a particular shape.

Mixtures of Polymers

A single CYSC polymer or a mixture of CYSC polymers can be used. The CYSC polymer or polymers can also be mixed with an additional polymer which is not a CYSC polymer. The criteria for the selection of a particular CYSC polymer or mixture of CYSC polymers, and optionally one or more additional polymers, depend upon the drug and its desired loading and/or delivery, as further discussed herein. Some embodiments of the invention make use of a composition containing a mixture of two or more CYSC polymers having substantially different melting temperatures, for example melting temperatures which differ from each other by at least 2° C., or at least 4° C. or at least 6° C. or at least 8° C. or at least 10° C. For example, the composition may contain one or more polymers melting at 37° C. and others melting at 39° C. and still others melting at 41° C. Other embodiments make use of mixtures of polymers having drug bound through a range of ionic strengths as defined by the pKa or pKb of the drug-polymer pair.

Formulations

In some formulations, the amount of the drug is at least 5%, at least 8%, at least 10%, at least 20%, at least 25%, at least 30%, at least 35%, at least 40%, at least 50%, at least 55%, at least 60%, or at least 70% of the total weight of the composition. Some formulations may have between 0.1% and 5%, for example up to 2%, 3% or 4% drug.

One of the many useful characteristics of this invention is the possibility of matching a particular drug with a particular CYSC polymer or mixture of CYSC polymers so as to provide desired loading and release characteristics. For many drugs, it is possible to select a CYSC polymer which contains containing hydrophobic side chains and optionally hydrophilic moieties provided by Rz moieties, and which therefore interacts favorably with the drug. For example, the CYSC polymer can provide sites for association with a drug by van der Waals forces, ionic association, hydrogen bonding, ligand attachment or covalent bonding. Covalent bonds may be formed for example through an amino or carboxyl linkage, or a divalent organic or inorganic moiety, e.g. an ester, carbonyl, amide, hydrocarbon, an amino, or ether link. Ionic bonds may be formed for example through an ionic salt linkage (for example a carboxyalkyl ammonium, sulfonium or phosphonium ion pair).

Since the CYSC polymer may comprise an amphiphilic structure, with both hydrophobic and hydrophilic moieties, entropic considerations will tend to produce a secondary structure wherein the hydrophilic moieties position themselves on the outside of the structure in an aqueous environment and wherein hydrophobic drug molecules are retained within the interior hydrophobic environment. Drugs may be hydrophobic or hydrophilic and may associate with the hydrophobic or hydrophilic moieties of the polymer.

A CYSC polymer comprises hydrophobic side chain moieties, and as a result a hydrophobic drug may associate with the hydrophobic moieties and thus be protected from an aqueous environment surrounding the formulation. Hydrophobic drugs include, for example, statins, such as atorvastatin, symvastin and pravastatin, SSRIs such as sertraline, anti-inflammatory-steroid such as budesonide, risperidone and many other pharmaceutically important molecules.

In some embodiments, the CYSC polymer includes units comprising ionic groups, e.g. units derived from ionic vinyl monomers. The ionic groups can help to stabilize the polymer formulation or help in disassociating the formulation in body fluids. For example, a CYSC polymer containing carboxylate functional groups can reduce or eliminate release of a drug in the acidic environment of the stomach, but can swell in the alkaline environment of the small intestine, thereby releasing the drug in the upper intestine. Other embodiments may employ for example, PEGylated monomers or acidic or other non-ionic or ionic monomers respectively that may be incorporated together as part of the same CYSC polymer or may be present in separate CYSC polymers to be mixed with a drug. The route of drug administration will often be a factor in determining the desirability of the number of ionic or hydrogen bonding groups in the CYSC polymer. For example, a small protein or polypeptide can be mixed with a CYSC polymer to make a stable drug formulation and then administered orally. The protein administered by itself orally might be destroyed when exposed to the high acidic environment of the stomach. When mixed with CYSC polymer, the protein would be protected from degradation. Alternatively an acid-stable component may be added such as transferrin. In certain embodiments, a protein may be complexed with an absorption enhancing component such as an organic acid, for example with deoxycholic acid, hydroxypropyl-g-cyclodextrin, cholic acid.

In some embodiments the Z(Rz)- moieties may also enhance the physical surface properties of the formulation. For example, polyoxyethylene (meth)acrylate units can provide beneficial slip or hydrophilic properties to tubing, catheters, probes and other medical devices. In some embodiments, the Z(Rz) moieties may also help in the sustained release or delivery of the drug.

As an embodiment of this invention, it is often desirable to reduce burst in order to provide a more steady or zero order delivery of drug to an mammal or cell. For example noted in the definition of burst, it is often observed in drug delivery formulations that upon administration there is an initial release of drug from the formulation above the desired therapeutic level, thereby, wasting and often overdosing the drug and in turn reducing the long term theoretical release of drug in the formulation to the mammal or cell.

We have found that many formulations of this invention exhibit a reduced burst effect. Moreover we can reduce even more the "burst" of drug by pre-treatment of the CYSC polymer drug formulation before administration. The CYSC drug formulation is easy to handle, often because of the low molecular weight and easy processing ability of the CYSC polymer because of the selection of the Rz functionality to assist in mixing with the desired drug.

Once the drug has been mixed with the CYSC polymer and isolated as a crystalline or semi-crystalline material, the CYSC polymer and drug formulation can be treated with solvents, buffered solutions or other aqueous or aqueous and organic solvent solutions for periods of time at ambient conditions. After this treatment the resulting CYSC polymer and drug formulation generally will exhibit a much lower and in some cases almost no burst effect. This embodiment is a significant advantage of preferred CYSC polymers of this invention compared to other drug delivery polymers.

In some embodiments, the presence of PEGylated groupings in the CYSC polymer can increase serum half-life levels of the PEGylated drug, and can reduce immunogenicity and immune recognition of the PEGylated drug. Other enhanced properties that may be provided by PEGylation include bioadhesive properties, and antithrombogenic properties.

In some embodiments, the Z(Rz) moiety can assist in making the polymer formulation more bioadhesive. For example, carboxylic acid or hydroxyl moieties can improve bioadhesivity to muco or intestinal surfaces, as can heparin and heparin sulphates. Hydroxyl or alkoxy polyoxyethlene moieties can also assist in bioadhesion and comparability of the drug.

In some embodiments of this invention, the CYSC polymer contains moieties which, either by hydrogen bonding or ionic bonding or covalent bonding, associate with the drug. These moieties may be derived from comonomers which constitute a minor proportion of the monomers from which the CYSC polymer is derived, for example 1% to 50% by weight (e.g., less than 1, 3, 5, 7, 10, 15, 20, 25, 30, 35 or 40% or from 1-5%, from 1-10%, or from 1-20%), or a major proportion, for example 50 to 95% or 75 to 95% by weight, or any weight in between, of the CYSC polymer (e.g., more than 30, 40, 50, 60, 70, 80, 85, 90 or 95% or from 20-40%, from 30-50%, or from 50-80%).

The selection and amount of the comonomers providing hydrogen bonding or ionic bonding is preferably based on:
a) The active or polar groupings in the comonomer or comonomers and the amount of complimentary active or polar groupings in the drug molecule (Hydrophobic/Hydrophilic properties).
b) The hydrophilic or the hydrophobic properties of the drug.
c) The amount of drug to be mixed in the polymer formulation (loading).
d) The control and reduction of the "burst effect" normally observed with a polymer drug reservoir.
e) The desired control of sustained drug delivery which is affected by the interaction of the drug ionically, through hydrogen bonds, ligand attachment or through van der Waals forces with the crystalline side chain polymer (Controlled, Sustained Delivery).
f) The method of administration of dosage forms made from the formulation (Form).
g) Quick release of drug when pH activated.

In some embodiments, the presence of Z(Rz) moieties may result in a significant number of stoichiometric ionic interactions between the CYSC polymer and the drug, thus making it possible to prepare a composition having a high loading of the drug.

In some embodiments, the CYSC polymer includes Z(Rz) moieties that can form a covalent bond with the drug. In such embodiments, the extent of covalent linkage between the CYSC polymer and the drug will be an important factor in determining release characteristics of the formulation.

For example, with some orally administered drugs it is difficult to administer acid sensitive drugs as the drugs are degraded in the stomach. Likewise it is difficult to administer acid sensitive drugs directly to the stomach lining. By using a strongly covalently associated drug-polymer formulation, the drug can survive the high acid environment of the stomach with the protective hydrophobic side chain groups surrounding and shielding the drug which is tightly bound through covalent linkage to the CYSC polymer. Once in the alkaline environment of the intestine, the presence of acid groups in the polymer formulation will cause the polymer formulation to swell and allow esterification or other lysis of the covalent bonds, thereby releasing the drug in the small intestine. In one such embodiment a copolymerizable monomer is used to bind the drug covalently to assist in the eventual release of the drug from the polymer formulation. Various covalent bonds may be used to bind the drug to the polymer; some may acid labile, some base labile, and some sensitive to enzymatic cleavage.

Any method can be used to covalently bind a drug to a CYSC polymer. In one example, the CYSC polymer contains a reactive group which is reacted with the drug. In another example, the drug is modified so that it can be used as a comonomer in the preparation of the CYSC material. For example, the drug can be reacted with a vinyl-containing monomer, e.g. with (A) a vinyl monomer containing an acid group which is reacted with (i) a hydroxyl group in the drug to give an ester, or (ii) with an amine group in the drug to give an amide; or (B) a vinyl monomer containing a glycidyl group which is reacted with an acid-containing drug to give an ester alcohol linkage; or (C) a vinyl monomer containing an anhydride group is reacted with a drug containing an amine or hydroxyl moiety to give an amide-acid or an ester-acid covalent linkage, respectively. The modified drug is copolymerized with one or more other monomers, at least one of which comprises a Cy moiety, or with an oligomer or macromer containing a Cy moiety, to give a CYSC formulation.

In certain embodiments, such as for gastric delivery, the formulation is such that a covalently bound drug is released from the CYSC polymer under conditions of low pH or by gastric enzymes. Exemplary active ingredients are those medicinal agents wherein gastric release is preferred over intestinal release or wherein control of the rate of release of the active agent is desired for systemic action. For example, drugs in which delivery to the stomach is preferred include natural or synthetic prostaglandins and prostaglandin analogues and prostacyclins, (e.g., misoprostol, enisoprost, enprostil, iloprost, and arbaprostil) any drugs for the treatment of peptic ulcers, gastric antisecretory drugs, antimicrobial drugs, prokinetic drugs, cytoprotective drugs and the like. Exemplary antimicrobial drugs include tetracycline, metronidazole and erythromycin which can be used for eradication of gastric microbes such as *Heliobacter pylori*.

In some embodiments of the invention, drugs are bonded to a CYSC polymer for release in an acidic environment depending on the desired physiological action of the drug, systemic side effects associated with each drug, decomposition rate of the drug in a particular environment and other factors well known in the medicinal arts. Such a covalent bond may be pH sensitive and capable of being cleaved at pH values of up to about 7 but stable below that pH.

Covalent bonds which can be cleaved under acidic conditions include bonds of the following types: silyl ethers and esters, acetal, thioacetal, imines, amine, carbonates, and vinyl ethers. Silyl ether covalent bonds are preferred in certain embodiments because such a bond can be formed between a silyl functional group on the polymer (or linker group) and any hydroxyl functional groups on the drug. The drug can be covalently bonded to the polymer backbone or to a pendant functional group on the polymer backbone and can for example be released from the polymer by hydrolytic cleavage of the covalent bond at a pH below about 7. The drug can be incorporated into the polymer by way of a pH-sensitive covalent bond which can for example be cleaved at pH values of less than about 7 but not at higher pH values. Release of the drug at such higher pH values, such as about greater than 7, 8, 9 or 10 or higher, is inhibited.

In some embodiments, the CYSC polymer swells at desired pH values, for example pH values of about 1-7 to enhance release of an effective amount of the drug. The drug can for example be covalently bonded to the polymer as described above through a pH-sensitive linker such that when the polymer swells upon exposure to the acid environment, the release of the drug into the gastric environment is facilitated. In a related embodiment, the formulation releases the drug at pH values up to about 7 and inhibits release of the drug for inhibiting release of the active ingredient at pH values above 7.

Alternatively, in some embodiments, the polymer can be designed such that the drug remains attached to the polymer at low pH and is triggered to release at high pH.

In one example of the preparation of a formulation in which a modified drug is incorporated into the CYSC polymer, ibuprofen (p-i-butylphenyl propionic acid) is modified by reaction with glycidyl methacrylate, and the modified drug is copolymerised with a linear alkyl acrylate (stearyl acrylate) and an additional copolymerizable monomer, acrylic acid, to give an Ibuprofen CYSC acid containing drug formulation. This drug formulation, administered as a crystalline solid, would bypass the stomach and once in the upper intestine would hydrate, swell, and hydrolyze, releasing ibuprofen for colonic delivery of this drug. Or, ibuprofen can be esterified with a preformed crystalline copolymer of stearyl acrylate and hydroxyethyl (meth)acrylate. A similar ibuprofen acid containing CYSC formulation would be available for colonic delivery of ibuprofen.

In another example, acryloyl chloride is reacted with a hydroxyl group or an amine group of a drug to provide a vinyl containing attachment covalently linked to the drug. This drug-vinyl monomer can then be reacted with the side chain crystalline monomer.

In another example, a vinyl anhydride, e.g. methacrylic anhydride, is reacted with a hydroxyl-containing drug to form a covalent ester linkage between the vinyl anhydride and the drug. Once the modified drug is formed, side chain crystalline monomer is introduced into the reaction mixture and a copolymer is formed between the modified drug, the side chain crystalline monomer and the by-product methacrylic acid (formed from the reaction of the hydroxyl containing drug with the vinyl anhydride). The reaction by-product of methacrylic acid in this case is easier to handle than the hydrochloric acid by-product obtained with the reaction of acryoyl chloride in the earlier example. The methacrylic acid by-product becomes a comonomer with the vinyl group containing therapeutic drug molecule. This type of formulation would be useful for an orally administered drug that, if administered alone, would be damaging to the stomach. In this formulation the presence of excess copolymerized methacrylic acid would help hydrate the molecule once the formulation has passed through the stomach to the small intestine for hydrolysis of the covalent bound drug and absorption in the small intestine. For example, a PLGA polymer can be functionalized with a drug like Ibuprofen (p-i-butylphenyl propionic acid) through reaction of the carboxylic acid group of Ibuprofen with the OH terminal group of PLGA. Then, this material can be succinylated with succinic anhydride and the remaining carboxylic acid group can be esterified with a polyol, for example, glycerine, and then end capped with stearic acid or stearoyl chloride to make a bioerodible CYSC polymer covalently bonded to a drug, in this example, Ibuprofen. Or, a PLGA can be esterified at the terminal hydroxyl group to create a PLGA stearate which can be reacted with polyol, for example glycerine and then esterified with Ibuprofen to give another form of a bioerodible CYSC polymer covalently bonded to a drug, in this case again, Ibuprofen. These are examples which indicate how a bioerodible CYSC polymer can be attached covalently to a drug to create a bioerodible CYSC polymer prodrug. Many possibilities exist for making similar CYSC bioerodible polymers covalently bonded to a drug.

In some embodiments, a covalently bound drug is released from the polymer carrier enzymatically, for example through ester hydrolysis by an esterase enzyme that would hydrolyze all the acrylate ester linkages.

In some embodiments, the CYSC polymer comprises functional groups to assist in the transport of the formulation into a biological system e.g., through a membrane or into a cell or through a mucous membrane layer, or to assist in the adherence of the formulation to deliver the drug. For example the formulation can include mucoadhesives sites, dermal adhesives, or large molecules that enhance bioavailability and reduce immunogenicity, for example, polyoxyalkylene vinyl monomers may be linked to PEG or PEGylated groups. These PEGylated groupings in the CYSC polymer will typically be introduced as comonomers, [Z(Rz)].

In some embodiments, the formulation includes a ligand to provide targeted adherence of the formulation to a target receptor on the target tissue. Ligand molecules can be added to the formulation during or after formation of the drug-polymer formulation. For example, a complexing molecule, a ketoester or a diamine containing copolymerizable monomer may be incorporated by polymerisation into the CYSC polymer. This complexing group can interact with a ligand as the formulation is prepared. Thus, drug-polymer formulations can be manufactured and then targeted to the desired target tissue, for example after biopsy and tissue analysis.

In some embodiments for gastric delivery, the CYSC polymer provides a number of interacting ionic and hydrogen bonding groups that assist in sterically protecting the sensitive drug in the harsh acidic environment of the stomach. After mixing and cooling, the crystalline side chains will lock the protein or peptide in the hydrophobic side chains, thereby, providing steric protection to the acid sensitive drug. Once through the stomach, the higher pH upper intestine will hydrate the ionic groups of the CYSC polymer allowing release of the sensitive drug into the intestinal tract. The polymer may release or expose the drug by various means including swelling, hydrolysis and by melting by external thermal induction, or by any combination of these means.

For example, a CYSC polymer derived from a linear alkyl acrylate monomer and an acid-containing monomer can be mixed with an amine containing drug, e.g., Sertraline, and cooled to provide a formulation. Upon cooling, the polymer drug ionic structure crystallizes. Once ingested, the crystalline domains protect the drug from reaction with components of body fluids. In its crystalline form this drug is protected from the acidic stomach environment and would not be available for absorption, whereas in the upper intestine the CYSC polymer would hydrate with the excess of acid groups in the CYSC polymer, thereby, releasing the Sertraline for absorption in the upper intestine.

In some embodiments, the CYSC polymer is in the form of a hydrogel. (In other embodiments, it should be noted, the invention specifically excludes a hydrogel). Hydrogels are preferred in some cases because a solid powdered hydrogel can be easily mixed with a solid powdered drug and then hydrated for application. Hydrogels can be hydrophobic, or amphiphilic (i.e. hydrophobic and hydrophilic), and they can be ionic or non-ionic. For example, a CYSC polymer containing units derived from a N-iso-propyl acrylamide comonomer, either alone or in combination with units derived from acrylic and/, or methacrylic acid can form hydrogels which are both hydrophobic (from the side chain crystalline monomers) and hydrophilic (from the N-iso-propyl acrylamide and acrylic acid monomers) and which can associate with (depending on the percentage of the hydrophobic and hydrophilic portions) either a hydrophobic or a hydrophilic drug.

Non-ionic hydrogels swell when they absorb water. Ionic hydrogels, which can be anionic or cationic, can be caused to swell to varying degrees by a change in pH. An alkaline pH causes swelling of an anionic gel (because an ionic groups are ionized at high pH), whereas a low pH causes swelling of cationic gels.

If the drug is hydrophilic, the drug is absorbed in the hydrophilic portion of the amphiphilic CYSC polymer hydrogel. The hydrogel can be designed to swell at high pH or low pH and/or at a temperature above the melting temperature of the CYSC polymer when mixed with the drug. After cooling, the drug is captured in the CYSC polymer hydrogel. If the formulation is heated after it has been delivered, it releases the drug. The temperature switch of the hydrophobic side chain portion, the hydrophobic property of the side chains and the hydrogel properties are factors which influence the delivery of the drug.

In some embodiments, the CYSC polymer is in the form of a non-ionic hydrogel prepared by polymerizing monomer component comprising an SCC monomer and a neutral hydrophilic comonomer, for example, hydroxyethyl methacrylate, together with a small portion of a crosslinking agent, e.g. ethylene glycol dimethacrylate. In addition, polyoxyethylene glycol methacrylate monomer may also be included, thus adding to the gel structure and providing possible antithrombogenic properties to the formulation. This polymer is also an amphiphilic polymer. As such it can be compatible with either or both hydrophilic or hydrophobic drugs. The amount and type of side chain crystalline monomer and the hydrogel structure can be factors in regulating how the drug in the formulation is released, e.g. how fast, where, and when, particularly if external stimuli to change temperature are provided.

In some embodiments, the formulation comprises a neutral hydrogel prepared by polymerizing an SCC monomer, acrylamide and t-butyl acrylamide, together with a small amount of methylene bis acrylamide. Such a hydrogel can associate with a hydrophilic or hydrophobic drug.

In some embodiments, the formulation comprises a hydrogel prepared by polymerizing an SCC monomer, acrylic acid and a block polyoxypropylene/polyoxyethylene/polyoxypropylene ester of acrylic or methacrylic acid. The resulting amphiphilic CYSC polymer, dependent on the block structure of the oxyalkylene ester, will absorb varying amounts of a hydrophilic or a hydrophobic drug or a little of both drugs. These drugs may be released slowly dependent on the hydrophobe/hydrophile balance of the oxyalkylene ester and the hydrophobe from the SCC monomer.

In the embodiments making use of a hydrogel, the units derived from the SCC monomer provide a powerful tool for regulating the uptake into, and the later delivery of a drug from, a formulation of this invention. In addition, the gel or hydrogel structure can help to regulate the release of drug to the location desired. For example, a pH sensitive hydrogel containing units derived from acrylic acid will facilitate protein loading. Formulations of protein and acid hydrogel protect the protein in the stomach, but swell and release the low pH sensitive protein in the small intestine, where the alkaline environment causes hydration and swelling of the hydrogel by interaction with the units derived from, for example, copolymerised acrylic acid. The swelling of the hydrogel can regulate the release of drug, because the hydrogel acts like a membrane, thereby overcoming the normal "burst effect" and allowing slow but deliberate release of the protein.

In some embodiments, the formulation contains a crosslinked CYSC polymer which, because it at least partially retains its shape even under conditions which would cause melting or swelling of the corresponding non-cross-linked CYSC polymer, e.g. above its Tp, will tend to hold a drug longer than the corresponding non-crosslinked polymer. Other embodiments specifically exclude CYSC polymers which are cross linked or immobilized on a support so that they cannot flow at temperatures above their melting temperature.

When the formulation is administered orally, the molecular weight of the CYSC polymer is preferably high enough to limit or avoid absorption across the intestinal wall. For example, polymers which are of high molecular weight, e.g., 1,000-160,000 Mn, and/or which are charged or crosslinked, and/or which are insoluble under physiological conditions, eliminate or significantly reduce transportation of the polymer across the gut wall. The CYSC polymer carrier, after having released the drug, will be passed through the GI tract and be voided.

It is generally preferable that the CYSC polymer be substantially physiologically inactive.

In some embodiments, the formulation includes or is secured to a bioerodable polymer, e.g. PLA or PLGA. Implanted applications, for example, may employ a mechanically solid implant wherein the CYSC formulation is bound to or contained within the bioerodable polymer.

In some embodiments, the formulation is delivered intravenously. In such embodiments, it may be desirable to mix the CYSC polymer with a bioerodable polymer, e.g. portions of natural molecules. In one such embodiment, polylactic acid and/or polyglycolic acid can be grafted by covalent reaction to the CYSC polymer before it is associated with the drug. In another such embodiment, a highly crystalline bioerodable polymer, e.g. a polycaprolactone polymer, e.g. of a desired molecular weight, which will provide a straight chain crystalline moiety, is physically mixed with, the CYSC polymer before it is associated with the drug.

In some embodiments, the CYSC polymer has a gel structure provided by the inclusion in the monomer mixture of a cross-linking multifunctional monomer. Such monomers are best employed in emulsion polymerizations, since, in other types of polymerization, they result in viscosities which are difficult to handle. Exemplary crosslinking monomers are ethylene glycol dimethacrylate, butylene glycol dimethacrylate, trimethylol propane triacrylate hexane diol diacrylate and the like. These crosslinking monomers are generally employed only in small amounts, e.g. less than 0.5%, or less than 1%, such as 0.1% to 5%, or 0.2 to 2%.

The formulations of the invention can contain, or be coated with, or be coated onto, any other material which does not have a substantial adverse effect on the value of the formulation as a drug delivery vehicle. Many such materials are well-known to those of ordinary skill in the art. In some embodiments, the formulation includes additives commonly used in the pharmaceutical industry, e.g. for the manufacture of tablets, pills or capsules, including excipients such as binding agents (e.g. methyl cellulose); fillers (e.g. corn starch, sucrose); lubricants (e.g. stearic acid, magnesium stearate, colloidal silica); and disintegrators (e.g. sodium starch glycolate, alginic acid). Formulations in the form of particles or tablets can have coatings thereon, e.g. coatings of materials such as hydroxypropyl methyl cellulose and acrylic acid polymers and copolymers. Certain embodiments specifically exclude formulations containing components which are useful as herbicides and insecticides.

In some embodiments of the invention, the CYSC polymer is in the form of an emulsion. The average size of the particles in the emulsion (and preferably the maximum size of substantially all particles) is preferably less than 1200 nm, e.g. less than 800 nm or less than 500 nm, for example less than 200 nm or less than 100 nm (0.1 µm). In many embodiments, the size of emulsion particles is 50-200 nm, or 50-500 nm, or 100-1000 nm. Such emulsions can be prepared using the techniques described in U.S. Pat. Nos. 6,199,318 and 6,540,984, the entire disclosures of which are incorporated herein by reference for all purposes. Emulsions are for example useful for compositions to be injected, generally intravenously, but in some embodiments, intramuscularly or into other tissues. In general, injectable emulsion particles have a diameter of less than 800 nm.

Emulsion polymers may be made prior to mixing with a drug and in other cases in the presence of a drug. In some cases emulsions of particles containing a drug immobilized within a CYSC polymer can be formed by a number of routes including (a) emulsifying a mixture of polymer and drug in water using a variety of surfactants and emulsifiers, (b) emulsifying a polymer-drug conjugate (with polymer-drug conjugate being defined as the drug being chemically bound to the polymer through covalent, ionic or hydrogen bonding) in water using a variety of surfactants and emulsifiers, (c) pre-emulsifying a preformed polymer and then adding a therapeutic drug that has a preferred partition coefficient such that the drug prefers to enter the hydrophobic particle and is either un-bound or linked through a covalent, ionic or hydrogen and, (d) preparing a stable water based polymer by emulsion polymerization and then adding drug as in (c).

In some embodiments the formulation comprises not only a CYSC polymer but also another type of polymer, which may be a main-chain crystalline polymer. For example, the CYSC polymer can be mixed with an amorphous or main-chain crystalline lactide or mixture of glycolide and lactide crystalline main-chain PLGA polymer, or with poly(epsilon-caprolactone (PCL), poly(dioxanone—a polyether-ester), polyhydroxybutyrate (PHB), polyhydroxyvalerate (PHV) and polyhydroxyalkanoates (PHAs), and polyesters from 3-HP—3-hydroxypropionic acid.

Also, as a diluent in the formulation, naturally occurring polymers or their hydrolysis or degraded products such as sugars, hydrolyzed starches, hyaluronan (also called hyaluronic acid or hyaluronate), chitan or chitosan may be used.

Making Drug-Polymer Formulations

In certain embodiments the formulation is prepared by melting the CYSC polymer, mixing the drug with the molten polymer, and cooling the mixture to below its melting point to cause crystallization and solidification of the formulation. In some embodiments a solvent may be used to help the drug and the polymer mix, but in other embodiments no solvent is required due to the low melting point of the CYSC polymers used. Carriers, fillers, excipients, dyes, colorings, flavors, disintegrants, stabilizers and other materials may be added to the mixture before it solidifies. The formulation can be processed, either while the polymer is still molten or object has solidified for example into rods, ovals, other forms, and tablets etc using known procedures. The CYSC polymer can be selected to have a Tp and a melting range such that there is little or no danger that the drug will be exposed to a temperature or pH which will damage it.

Some CYSC polymers have well defined, low melting temperatures such that it is unnecessary to use solvent to achieve the viscosity needed to allow easy mixing. Thus the invention is particularly useful for the formulation of drugs and other drugs which can be damaged, e.g. denatured or partially or completely inactivated, by such exposure, for example drugs which are damaged by exposure to temperatures higher than a temperature which is more than 15° C., or more than 30° C. above the Tp of the CYSC polymer, for example more than 50° C. or more than 65° C. The melting temperature of the polymer (or polymer mixture) used in the formulation may, for example, be about (or alternatively be not more than) 30° C., about 35° C., about 37° C., about 40° C., about 42° C., about 45° C., about 50° C., about 55° C., about 60° C., about 65° C., about 70° C., about 75° C., about 80° C., or other temperature desired. The polymers may, for example, have melting temperature ranges from 35° C. to 65° C., 40° C. to 65° C., 45° C. to 60° C., 40° C. to 60° C., 50° C. to 65° C., or other range between or within any two of the above temperatures. Generally it is desirable that a polymer-drug composition will have a melting temperature above that of body temperature of the subject (e.g., 37° C.). However, in some embodiments, it will be desirable that the polymer-drug composition have a melting temperature above 37° C., so that the dosage form, once implanted maintains a non-solid consistency.

In certain alternative embodiments the mixture of the drug and melted polymer is dispersed rapidly into cold water or spray dried into a chamber, whereby the polymer formulation precipitates or dries, respectively, into an isolatable form. Microspheres and microcapsules may be formed in this way. However, in some preferred embodiments the drug formulations of the invention particularly exclude microspheres and microcapsules.

Many of the polymers which are already known for use in drug delivery require the use of solvents and/or high temperatures to produce a mixture of the polymer and drug. Some other known drug delivery systems employ hydrogel systems which require the use of ionic conditions to produce a mixture of the hydrogel with the drug. Such temperatures and/or the solvent conditions and/or ionic conditions can inactivate or denature totally or partially the drug. In the present invention, by selecting a CYSC polymer having a low melting temperature, the CYSC polymer can, if desired, be mixed readily in "neat" or 100% pure form with the drug, and it is unnecessary to use a solvent or apply excessive heat or unusual ionic groups that might harm or inactivate a sensitive drug.

Drug Loading & Release

In preferred embodiments, this invention provides one or more of high drug loading, low burst effect, and sustained release of a drug from a CYSC polymer formulation tailored to provide the desired characteristics for the particular drug.

Total drug loading is the amount (usually expressed as the percentage by weight) of the drug present in the formulation. The drug may be chemically and/or physically bound to the CYSC polymer, for example physically entrapped in the formulation. Binding of the drug to the polymer may be through covalent and/or ionic and/or hydrogen bonding and/or van der Waal's forces and/or hydrophobic interactions.

Conventional drug formulations generally contain less than 5% by weight of drug. Conventional polymers used for sustained release formulations, such as PLGA (co-polylactic acid-co-polyglycolic acid) and simple acrylic copolymers that are non-crystalline, have relatively low drug loadings of between about 1% and 5%. In contrast, preferred embodiments of the present invention provides formulations with high drug loading. In some embodiments, the formulation of this invention contains at least 1% by weight of the drug. For example, the formulation can contain at least 1%, at least 2%, at least 5%, at least 7%, at least 10%, at least 15%, at least 17%, at least 20%, at least 30%, at least 40%, at least 45% at least 50%, at least 60%, or at least 70%, e.g. 1-20%, 5-30%, 10-30%, 10-50%, 20-30% or 20-50% by weight of the drug. In preferred embodiments the formulation contains at least 10% by weight of drug, and generally between 10% and 30% by weight of drug. In other embodiments, the formulation can contain less than 1% of the drug. High drug loading is particularly useful for sustained release formulations. In some embodiments, the present invention combines high drug loading with reduced burst effect.

Tailoring drug loading and release properties for a particular drug may be achieved for example through selecting polymers with a combination of desired features relating to (a) ionic or covalent attachment of drug molecules to CYSC polymer, and/or (b) capturing the drug molecules in the crystalline hydrophobic domain, and/or (c) presenting a tortuous path around crystalline domains that drug molecules in the hydrophilic domains must navigate to reach the exterior and/or (d) ensuring that the crystalline domains are preferentially on the outside of the formulation. Methods of preferentially locating the crystalline domains on the exterior include, for example, forming particles in air using a spinning disk allowing the hydrophobic side chains to come to the low energy interface or in a hydrophobic medium that would again draw the hydrophobic side chain to the interface, or actually coating preformed particles.

Drug loading and release properties of CYSC polymer formulations can be controlled by altering the solubility of the drug in the polymer and providing association sites for the drug to interact with the CYSC polymer. For example, if the drug is a protein or polypeptide, the ionic groups in the CYSC polymer are preferably selected from those cationic or anionic groups which naturally associate ionically or through hydrogen bonding with the carboxyl or amide groups of the protein or polypeptide side chains. Such ionic groups can be derived from suitable cationic or anionic comonomers forming part of the CYSC polymer or can be subsequently prepared on the preformed polymer by quaternization of, for example, a tertiary amine comonomer copolymerized in the crystalline side chain polymer. Quaternization of a tertiary amine function on the crystalline side chain copolymer can be affected by methyl or some other alkyl chloride or by dimethyl or other dialkyl sulfate treatment of the t-amine to form the quaternary ammonium salt.

A more hydrophobic drug may have a lower concentration of a hydrogen bondable or ionic group containing monomers. Yet, there are many hydrophobic monomers that contain ionic groups or contain hydrogen bonding capability to allow the more hydrophobic drug molecules to form strong ionic or hydrogen bonded associations with a therapeutic molecule.

In the case of sustained release formulations, several days, weeks or even months of therapeutic dosage may be required. A formulation of the invention (such as an implanted drug formulation or device, such as a coated stent or solid implant or polymeric drug depot) may provide at least 5 hours, at least 12 hours, at least 24 hours, at least 36 hours, at least 72 hours or at least 100 hours of therapeutically effective drug delivery. In certain embodiments, a formulation of the invention may provide at least a week or at least two weeks, three weeks or at least a month or three month's worth of therapeutically effective drug delivery to a subject.

In some uses of this invention, interactions between the drug and the CYSC polymer slow the release of the drug from the polymer into the surrounding physiological environment. For example, the interaction of the hydrophobic side chains of the crystalline side chain polymer with a hydrophobic drug will delay dissociation of the CYSC polymer and drug. If the drug is hydrophilic, the drug will tend to associate strongly with the hydrophobic side chains of the CYSC polymer, delaying release into a less hydrophobic (e.g. aqueous) environment. The side chains of the CYSC polymer influence melt temperature and once melted act somewhat like a plasticizer (i.e. an attached plasticizer). The molecular weight of the polymer also influences the release of the drug (for example molecular weight influences in drug diffusion from a crosslinked gel vs. a low molecular weight polymer). These factors are important in controlling the release rate of drug from the polymer drug formulation. If the CYSC polymer associates with the drug by ionic or hydrogen bonding, the drug will be slower to release.

Unexpectedly, it has been discovered that the crystallinity of the CYSC polymer is an important factor in drug loading and release.

The drug formulations of the invention can be specifically designed to provide controlled and/or sustained release. For example, a drug formulation of the invention may be designed so as to release no more than a certain amount of drug over a specific period of time under certain defined circumstances. The rate of loading and release will depend on the specific drug-polymer pair. For instance, a single dose of a drug formulation may release no more than 5% of the total drug loaded into the dosage form, or alternatively no more than 1%, 3%, 10%, 20%, 30%, 40%, 50%, 60% or 70% over a period of 1 hour, or alternatively 3 hours, 6 hours, 12 hours, 18 hours, 24 hours, 36 hours, 48 hours, 72 hours or any combination of the foregoing numbers.

The rate of drug released may be approximately zero order during the main period of therapeutic administration, for example over 99% or 95% or 90% or 80% or 75% of the period of therapeutic administration, or over a period defined by the period of implantation. The maximal variation of drug release rate over the main period of therapeutic administration (for example during the period when therapeutic administration is occurring, at least 12 hours following administration, and before drug release falls below a therapeutically effective level) may not be greater than 50% (or 40% or 30% or 20% or 10%) from the mean rate of release during that period.

The plasma concentration of a drug will be related to the rate of release into the blood balanced against the rate of clearing of the drug from the blood (the drug half-life concentration). The aim of sustained drug delivery is to achieve a therapeutic plasma concentration of the drug over a desirable extended period of time. The desired therapeutic plasma concentration will be a concentration within the therapeutic window below which drug is ineffective, and above which the drug is toxic, or alternatively has no additional beneficial effect.

In a typical embodiment of the invention, a therapeutic dose of the drug as measured by plasma concentration (but alternatively as measured by clinical measurements) will be released over a period of time ranging from at least an hour to at least twelve months. Exemplary drugs suitable for sustained release include, for example, anti-pain medications (e.g. morphine analogues), anti-psychotics (e.g. risperidone), anti-inflammatories (e.g. steroids or NSAIDs), cholesterol lowering drugs (e.g., statins), osteoporosis drugs (biphosphonates), anti-angeogenics (e.g., anti-VEGF) and contraceptives. In the case of certain drugs such as contraceptives and osteoporosis drugs, sustained release may be desirable over a period of more than a year, for example at least 2, 3, 4, or 5 years. Prior formulations (Norplant) have been used to deliver a therapeutic dose of contraceptives over a period of three years. Long term sustained release formulations will generally be formulated for implantation within the body, e.g., subcutaneously.

The amount (weight) of drug released over a period of time will of course be related to therapeutically effective plasma concentration of the drug, the potency of the drug and drug kinetics including the residence time in the various tissues of interest and the rate of clearing. In use, the rate of release of a drug from the pharmaceutical composition of the invention may be no greater than, for example long per hour, or alternatively, 50 ng, 100 ng, 500 ng, 1000 ng, 2500 ng, or 5000 ng or in other embodiments, no more than 10 µg, 50 µg or 100 µg or 500 µg or 1000 µg per hour during the first 6 (or 12 or 24 or 36) hours following implantation. Of course, the desired rate of release of the drug will depend on its potency, its therapeutic window and its half life. For example, Risperidone may be released over a period of time to provide a serum concentration of about 15 ng/ml up to about 100 ng/ml. A release of about 4 mg/day (or in other studies between 1 and 60 mg/day) is found to provide adequate therapeutic serum levels of Risperidone.

In vivo, when the drug is released from the formulation, it is released into the surrounding environment, which may be, for example, the intestinal lumen, gastric fluid, subcutaneous tissue, blood, muscle, the colonic space, a body cavity, or any surrounding tissue and/or into interstitial space. The rate of the release is not always easy to measure in practice, and the invention includes methods of determining the rate of release of a drug from a formulation of the invention in vitro, such as by using standard methods such as those described in the United States Pharmacopoeia. One such method, employs a large volume (usually about a liter) of phosphate buffer, pH 7.2, maintained at 37±0.5° C. and stirred at 100 rpm by using a paddle-type dissolution apparatus (such as may be obtained from Electrolab, Mumbai, India). Drug release studies are generally carried out in triplicate and the mean values are calculated. Many standard methods are well known, and when release rates are described and discussed herein, such release rates may be calculated and compared by these standard methods.

In some embodiments, the formulation is such that less than 20%, or less than 15%, or less than 10% (or in other embodiments, less than 1%, 3%, 5% or 7%) of the total drug loaded into the formulation is released from the formulation prior to activation of the formulation by a specified condition which triggers a substantially greater rate of release. Such release triggers include, for example, a change in pH and/or swelling of the polymer by hydration and/or contact with an enzyme and/or heating of the formulation. Such heating can for example make use of one of the means described above. Immediately following the specified condition, the formulation may release drug quickly as a bolus, or steadily over a period of time. For example it may release at least 50% (or 30%, 60% or 75%) of the total loaded drug over a period of not more than 1, 3, 5, 7, 10, 20, 30, 45, 60, 120 or 360 minutes following activation. In embodiments wherein a bolus release is required, substantially all the drug may be released over a very short period of time, such as not more than 1, 2 or 3 minutes, or in other embodiments where longer release is desired, over a period of not more than 30 minutes.

In some embodiments, the rapid melting characteristic of CYSC polymers is used to provide formulations which can be administered in the body and transported to a targeted disease site with little or no release of the drug during transport, but which can be triggered to release the drug at the site by targeted radiation which melts the CYSC polymer at the site. In this way a large dose of a drug can be delivered specifically at the target site when needed. This is particularly useful when dealing with toxic drugs that are best delivered in a site-specific manner and not systemically. Site-specific delivery also reduces the dose needed. Such drugs include cytotoxic agents such as chemotherapeutics. The external source of radiation may be, for example, a focused beam of radiation, e.g. infra-red (IR) or radiation of a similar wavelength. For example the radiation source may have a wavelength of about 400-1500 nm, e.g. 500-1200 nm or 700-1100 nm. This heat-induced release mechanism may be particularly useful in embodiments wherein the formulation is targeted to a specific site prior to release of the drug. Such embodiments include formulations to target tumour tissue whereby, upon heating, a chemotherapeutic agent is released locally, providing a concentrated bolus of drug at the target site, but minimizing systemic exposure.

For example, a chemotherapeutic agent such as carboplatin may be formulated with a CYSC polymer and a targeting ligand such as an antibody or folate that binds selectively to a cell surface receptor differentially expressed on the surface of a specific type tumour cell, for example a colon cancer cell. The formulation may for example be formulated as an emulsion and delivered orally. The emulsion will pass through the stomach and gut to the colon where it will preferentially adhere to tumour tissue. Excess formulation will be voided. An infra-red (IR) source will be used to target the tumour site, heating the adhered formulation and releasing the Carboplatin at high concentration to the target site. Little or none of the drug will be released from the formulation until the formulation is heated. This method of administration reduces the amount of drug delivered systemically and thereby reduces the damaging effects of toxic drugs on healthy cells. In certain embodiments, a material which can be heated by radiation, e.g. carbon nanotubes, may be mixed into the formulation. A similar embodiment might employ venous delivery of a liquid or emulsion formulation wherein the drug formulation specifically binds to a target at any location reachable by the circulation.

Initial burst release of a drug is often (but not always) undesirable, and the present invention provides a reduced burst effect due to the interactions between the drug and the crystalline side chains of the polymeric carrier material. In certain embodiments the formulation of the invention releases a drug so that the initial release of drug does not exceed the upper threshold of the therapeutic window. In other embodiments it exceeds the upper therapeutic window threshold for no more than 1 hour (or alternately no more than 2, 3, 4, 5, or 6 hours). In certain embodiments the formulation of the invention releases a drug so that the maximum initial release of drug does not exceed by more than 50% the mean rate of release of drug (the mean rate measured over a period from 3-12 hours post administration). Alternatively the maximum initial release of drug does not exceed by more than 20% or 30% or 40% or 70% or 100% the mean rate of release of drug as measured over a period from 6-24 hours or 1-12 hours or 12-48 hours post administration.

Generally a formulation of the invention may be implanted directly into a subject to provide acceptable burst effect and sustained release. But for some formulations, and particularly with some particularly toxic drugs that have a narrow upper limit to their therapeutic window, pre-treatment of the formulation may be done to reduce burst effect in vivo. Pre-treatment may simply involve soaking the formulation in a biocompatible liquid or elution buffer, for example phosphate buffered saline (PBS) or water for a period of time before implantation. In such an embodiment, the solid polymer formulation would be removed from its packaging, and placed in the elution buffer for, for example 30 minutes to an hour. In some embodiments longer soaking times may be desirable, for example overnight. Soaking may continue for any duration, for example for up to (or alternatively not more than) 1, 3, 6, 9, 12, 24 or 46 hours. This period of soaking will allow the formulation to equilibrate with its liquid environment and will provide some degree of hydration (if hydration does occur) such that and drug that has migrated to the surface, or any drug that would provide a burst release when implanted into the subject will now be released during the soaking period. After the soaking period the formulation will be implanted into the subject to provide sustained release of the drug within a therapeutic window.

In one specific embodiment the formulation is provided as part of a kit, wherein the kit comprises a two-chamber blister pack having the formulation in a first chamber and a liquid (an elution buffer, e.g. PBS) in a second chamber, and wherein an operator can break the seal between the first and second chambers allowing the liquid to contact the formulation. The formulation is per-treated in the liquid for a period of time, for example from 30 minutes to 2 hours to allow any burst to dissipate. The formulation is then removed aseptically from the packaging and implanted into the recipient subject, for example implanted subcutaneously by use of a simple trocar.

Drug Release

Temperature or pH changes may be used to induce drug release at a desired time and/or location. In some embodiments, a small increase in the temperature of the formulation, in situ in an mammal or cell, for example from body temperature to a temperature above body temperature, but below a temperature which would damage the mammal or cell around the formulation, causes the CYSC polymer to melt, so that it changes from a crystalline to an amorphous structure. The combination of the loss of crystallinity, and in the case of a hydrogel, loss in volume, are factors which are useful in the delivery of the drug.

Focused infrared radiation, for example, can be applied from outside the body to selectively heat a target within the body. In some embodiments a formulation may be delivered to a particular location within a patient without appreciable release of drug. When and where desired, an IR beam can be used to heat the target, causing a bolus release of drug at the desired location and time. One such embodiment uses a formulation that includes a ligand that binds specifically to a target. Such ligands may be, for example, antibodies, and are discussed further herein. The formulation is delivered to the patient, for example intravenously; the ligand allows the formulation to bind to and accumulate at a target, such as cancer tissue; a focused IR beam is applied to the target tissue, thereby releasing a bolus of drug.

Another method of promoting the release of a drug associated with a CYSC polymer inside a human body or other mammal or cell is to supply heat to the CYSC polymer, for example through one or more of a hot compress, hot water, hot contact wand, hot pad, infrared radiation, and penetrating heat via near infrared radiation; and/or by generating heat within the formulation. For example, the formulation can include a component which will generate heat when exposed to electromagnetic radiation of a particular range of wavelengths. Such components include for example carbon fiber nanotubules or particles which absorb near-IR light in the range of about 700-1100 nm, silver particles or gold particles.

In various other embodiments a transdermal formulation may be applied to the skin and heat may be produced by chemical or electrical means, or even by physical means such as rubbing with the hand to produce friction-induced heat, to provide a bolus release of drug. Such embodiments are further described herein.

The formulations may include a remotely controlled release mechanism to trigger release of the drug, e.g., an electromechanical mechanism that allows an operator to release drug by use of a radio-frequency signal, sent, for example, over a computer network such as the Internet or a hospital intranet. Such a mechanism may employ, for example, solenoids, electromagnetic gates or other microfluidic flow control mechanisms. Such mechanisms are well known in the microfluidic and MEMS industry. A remotely operated heating element may be provided to heat the formulation and thus release a bolus of drug.

In some embodiments a therapeutically effective dose of the drug may be released at a predetermined time wherein the drug is released from the formulation by one or more of the following changes in condition (i) heating the formulation, (ii) hydration of the formulation, (iii) exposing of the formulation to an enzyme, or (iv) changing the pH of the environment surrounding the formulation.

Methods of Administration of the Formulations and Diseases that May be Treated Using the Formulations of the Invention The formulations of the invention may be administered in various ways. Exemplary types of administration include: ingestion, injection, parenteral administration, oral, subdermal, transdermal, transmucosal, intrathecal, intramuscular, inhalation, and application to the skin. Compositions and devices of the invention include lozenges, capsules, tablets, pills, pessaries, lavages, suppositories, inhalable powders, creams, solutions, suspensions, oral suspensions, emulsions, micelle systems, nanoparticles, vesicles, nanocapsules, microcapsules, microparticles, microspheres, microparticles, particles, hydrogels, pills, tablets, including sub-lingual tablets, depots and injectables. Hydrogels are sometimes a preferred form in that they can be mixed as a powder with the drug in a solvent medium to hydrate the hydrogel/drug mixture.

The preferred formulation and route of application will depend upon the drug and the desired application. Sustained release formulations will need to reside in or on the body for the period of desired release, therefore such formulations will be implants, implanted devices and patches, for example transdermal, or transmucosal. Pills, capsules and syrups are typical for oral/gastro-intestinal formulations that are resistant to acid degradation. Because of their susceptibility to acid or severe environments, polypeptides and proteins are often administered by injection as suspensions or solutions. Topical application of other drugs will typically be in suspension or cream form.

Diseases that may be treated by the formulations of this invention include, but are not limited to, cardiac diseases, cardio-vascular diseases, neoplastic diseases, inflammation and all diseases associated with the inflammatory process such as arthritis, auto-immune diseases such as lupus, allergies, infectious diseases (viral, bacterial, fungal, protozoan and prion), endocrine diseases such as diabetes, obesity and all forms of weight-related diseases and disorders whether clinically significant or not, hypertension, psychosis, anxiety, depression or any psychological disease, addiction, erectile dysfunction or any sexual dysfunction, blood-lipid diseases such as high cholesterol, Alzheimer's, alopecia, propecia, mange, incontinence, pain, Meniere's disease, migraine, tinnitus, osteoperosis, fertility problems and any other disease of an mammal or cell for which administration of a drug is warranted.

Mammal or cells that can be treated by the present invention include for example human beings and other mammals, including bovines, primates, equines, ovines, porcines, canines and felines, and also birds, fish, ungulates, bovines, primates, equines, ovines, porcines, canines and feline animals.

Devices Employing the Invention

Various devices may be made using the formulations of the invention including coated devices, prosthetic devices, implanted devices, pills, depots and patches. In some embodiments a formulation of the invention is coated onto an implantable medical device. Such implanted devices include stents, pacemakers, catheters, screws, staples, sutures, prosthetic devices etc. Such devices can be made by applying the formulation to an interior or exterior surface of a device by dipping, painting, spraying, misting, rolling, or other method. In some methods, the formulation is heated to above its melting temperature and applied to the device and then dried to form a solid coating.

In another aspect, the devices are implanted depots such as solid, liquid and gelatinous depots that can be deposited into the tissue of a subject, for example by subcutaneous injection. In some embodiments, the formulation is heated to above its melting temperature and injected (or otherwise flowed) into the desired location, e.g. subcutaneously, where it cools and forms a depot which will then release drug in situ. In some such embodiments, Tp is only just above body temperature, e.g. less than 55° C., preferably less than 48° C., so that the formulation may be implanted with minimal discomfort or tissue damage. Once implanted, the formulation cools and crystallizes. Such an application may be of particular use in providing an implanted device that moulds to fit the internal shape of a cavity such as within an ablated area of an infracted heart, within bone tissue or subdermally.

In some embodiments, e.g. some depot embodiments, the formulation includes a non-polymeric substance, e.g. sucrose acetate isobutyrate (SAIB) and non-water soluble liquid materials having a viscosity of at least 5,000 centipoise at 37° C. that do not crystallize neat under ambient physiological conditions, for example those described in U.S. Pat. No. 6,992,065 (Okumu) which is hereby incorporated by reference in its entirely for all purposes. Such substances, for example SAIB, which are preferably highly hydrophobic, can enhance drug loading and/or modify drug release profiles. In some embodiments the material is physically mixed with the CYSC polymers; in other embodiments it may be used as or incorporated into the CYSC polymer.

In some embodiments, devices include a formulation containing a radio-opaque dye or other marker so that the formulation can be imaged by fluoroscopy or X-ray. Many radio-opaque substances are commonly known and used such as barium, silver and gold.

Drugs and Diagnostic Agents, Carriers and Excipients Used with the Invention

Any desired drug may be incorporated into the CYSC polymer formulation of the invention, depending on the particular application sought. The CYSC polymer may be loaded with one or more hydrophilic or hydrophobic drugs, for example, a small molecule, polypeptide, protein, carbohydrate, polynucleotide, nucleoside, siRNA, immunoglobulin of Fc or Fab fraction thereof, a cyclic compound, alkaloid, beta-lactam, or other antibiotic. The drug may also be an agonist or antagonist of neurotransmitters, an antipsychotic (for example fluphenazine maleate, chlorpromazine, chlorpromazine hibenzoate, sulpiride, carpipramine hydrochloride, carpipramine maleate, clocapramine hydrochloride, mosapramine hydrochloride, Risperidone (or any compound containing functional groups of benzisoxazole and/or piperidine), clozapine, olanzapine and sertindole); or an SSRI; or it may comprise cell signalling molecules such as cytokines such as lymphokines, monokines, chemokines, interleukins, prostoglandins etc a statin, a Cox-2 inhibitor, an SSRI, a calcium channel blocker, psychotropic drug, bisphosphonate, anti-proliferative, mitotic inhibitor, angiogenic factor, antangiogenic factor, small molecule such as rapamycin or derivatives, or almost any other type of drug. Specific drugs and drug classes include ibuprofen, uracils (e.g., 5-fluorouracil), steroids and esters of steroids or other hormones (e.g., estrogen, progesterone, testosterone, androsterone, cholesterol, norethinidrone, digoxigenin, cholic acid, deoxycholic acid, and chenodeoxycholic acid), boron containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, kedarcidin chromophore), heavy metal complexes (e.g., cisplatin, carboplatin), hormone antagonists (e.g., tamoxifen), non-specific (non-antibody) proteins (e.g., sugar oligomers, insulin), polynucleotides and oligonucleotides (e.g., mRNA sequence), radio-nuclides, toxins (e.g., ricin, and transcription based pharmaceuticals. In certain embodiments the drug may be or may contain bacterial toxins such as botulinum toxin (BOTOX).

or X, insulin or calcitonin. The same is true for any heat labile drug, allowing simple mixing while retaining biological activity of the drug.

In some embodiments, other chemotherapeutic agents used to kill neoplastic cells are incorporated into the formulations. Such chemotherapeutic agents include the following: 1) Alkylating agents, which destroy the cancer cell's DNA. E.g., Busulfan, Cyclophoshamide and Melphalan. 2) Nitrosureas, that inhibit a cancer cell's enzymes needed for DNA repair. E.g., Carmustine and Lomustine. 3) Anti-metabolites, that interfere with both a cancer cell's DNA and RNA. E.g., 5-Fluorouracil, Methotrexate and Fludarabine. 4) Anti-tumor antibiotics that interfere with a cancer cell's DNA in addition to changing its cellular membrane. E.g., Bleomycin, Doxorubicin and Idarubicin are examples of Antitumor Antibiotics. 5) Mitotic Inhibitors, that inhibit enzymes needed for protein synthesis in the cancer cell. E.g., Docetaxel, Etoposide and Vinorelbine. 6) Radioactive isotopes, which destroy cancer cells by the production of radioactive emissions. E.g., indium-111 ($^{111}$In), yttrium-90 ($^{90}$Y). These and/or other types chemotherapeutic agent may be incorporated into the formulations of the invention.

Drugs with well-known sustained release applications include, for example, anti-pain medications (e.g. morphine analogues), anti-psychotics (e.g. risperidone), anti-inflammatories (e.g. steroids or NSAIDs such as budesonide), hormones (e.g. testosterone or progesterone) cholesterol lowering drugs (e.g., statins), osteoporosis drugs (biphosphonates), anti-angeogenics (e.g., anti-VEGF) and contraceptives.

Any derivative (defined herein as including, but not limited to any pharmacologically active metabolite, or analogue, agonist, derivative, variant, congener, or isomeric form) of any

TABLE 1

A selection of some important drugs that can be incorporated into and delivered by the formulations of the invention includes the following:

| Name | Trade Name | Drug Class | $M_r$/Da | Hydrophobic |
|---|---|---|---|---|
| Atorvastatin | Lipitor | Statin | 1,209 | YES |
| Symvastin | Zocor | Statin | 418 | YES |
| Celecoxib | Celebrex | Cox-2 inhibitor | 381 | YES |
| Sertradine | Zoloft | SSRI | 343 | YES |
| Omeprazole | Losec/Prilosec | PPI | 345 | YES |
| Esomeprazole | Nexium (isomer of Prilosec) | PPI | 767 | YES |
| Pravastatin | Pravachol | Statin | 447 | NO |
| Azithromycin | Zithromax | Antibiotic | 749 | NO |
| Quetiapine | Seroquel | SSRI | 883 | YES |
| Metoprolol | Seloken/Toprol | β-blocker | 653 | NO |
| Budesonide | Pulmicort/Rhinocort | anti-inflammatory-steroid | 431 | YES |
| Clarithromycin | Biaxin | Antibiotic | 748 | YES |
| Paroxetine | Paxil | SSRI | 375 | NO |
| Oxycodone | Oxycontin | Opioid agonist | 351 | NO |
| Risperidone | Risperdal | Psychotrope | 410 | YES |
| Alendronate | Fosamax | bisphosphonate | 325 | NO |
| Venlafaxine | Effexor | SSRI | 314 | NO |
| Amlodipine | Norvasc | Ca-channel-blocker | 567 | YES |
| Olanzapine | Zyprexa | | 312 | YES |
| Lansoprazole | Prevacid | PPI | 369 | YES |
| Fluoxetine | Prozac | SSRI | 345 | NO |
| Finasteride | Proscar | steroid-antagonist | 372 | YES |
| Sildenafil | Viagra | PDE5-antagonist | 667 | NO |
| Rosuvastatin | Crestor | Statin | 1001 | YES |

Because the CYSC polymers can have a Tp well below the denaturation point of proteins (c. 60° C.), they can be mixed with various protein drugs, e.g., hormones such as growth hormones or sex hormones, secreted proteins, alpha-glucosidase, erythropoietin, antibody drug conjugates, Fc fusion proteins, interferon, anti-CD20 therapeutics, Factor VIII, IX drug described herein can equally be used; and any formulation described is intended to encompass formulations comprising such derivatives.

Ligand-Targeted Polymeric Drug Delivery

In certain embodiments, the crystalline side chain polymer incorporates ligands that bind specifically to target receptor molecules. Target receptor molecules are present on the surface of a specific type of target cell, such as a cancer cell. The ligands may be incorporated into the polymer formulation by copolymerization of a comonomer which carries a receptor covalently attached to the monomer. Alternatively a ligand may be incorporated into the formulations of the invention by any other means not involving covalent bonds such as mixing which allows the ligand to associate with the polymer either as a simple physical mixture, or by ionic bonds, hydrogen bonds, van der Waals forces or hydrophobic/hydrophilic interactions. The ligands bind specifically to molecules expressed on the cell surface of a target e.g., receptor proteins that are differentially over-expressed on target cells, for example cancerous cells.

For example, many types of cells express a large number of folate receptors on their cell surface, more so than for non-cancerous cells. Folic acid or derivatives or portions of folate can be physically mixed during preparation of the formulation, or added to the outside of particles formed after crystallization or precipitation of the formulation. The folate molecules bind specifically with the folate receptors on a target cancer cell. A chemotherapeutic agent, for example carboplatin or cis-platin or taxol, can be mixed with or bound by hydrogen bonding or otherwise to the CYSC polymer, and thereafter delivered to a specific cell target.

This ligand-targeted polymeric drug delivery system can be used to deliver any number of known targeted cancer therapy agents in several different classes. For example, small-molecule drugs can be used to block specific enzymes and growth factor receptors (GFRs) involved in cancer cell growth. These drugs act as signal-transduction inhibitors. One such drug that may be used with the invention is GLEEVEC (STI-571 or imatinib mesylate) to treat gastrointestinal stromal tumours and certain kinds of chronic myeloid leukemia. Another drug that may be used with the invention is IRESSA (ZD1839) that is used to treat advanced non-small cell lung cancer. This drug targets the epidermal growth factor receptor (EGFR), which is overproduced by many types of cancer cells.

Apoptosis-inducing drugs may also be incorporated into the formulation of the invention. One such drug is VELCADE used to treat multiple myeloma. VELCADE blocks proteasomes, which help to regulate cell function and growth. Other apoptosis-inducing drugs include GENASENSE to treat leukemia, non-Hodgkin's lymphoma, and solid tumours. GENASENSE blocks the production of BCL-2, which promotes the survival of tumour cells.

Other possible drugs include monoclonal antibodies that bind to growth factor receptors, such as HERCEPTIN (Trastuzumab).

In some embodiments, the formulation comprises, a slightly basic/neutral CYSC polymer derived from a mixture of an SCC monomer, hydroxyethyl methacrylate and dimethylaminoethyl methacrylate and a drug, for example, an anti-cancer drug, e.g. methotrexate. In one such embodiment, during preparation of the formulation, folic acid is mixed with the CYSC polymer and the drug or added to the formulation after isolation of the formulation, so as to concentrate folic acid at the surface of the drug formulation particles. Cancer cells have more folate receptor sites on their cell membranes, enabling concentration of the formulation at the cancer cell sites after administration of the formulation. Upon exposure to an external heat stimulus, the encapsulated or bound methotrexate is released as the CYSC polymer transitions from a crystalline to an amorphous structure. Alternatively, release of the drug may be stimulated by means other than heat, e.g. by one or more of hydration, swelling, osmotic expulsion and by increasing the permeability of the polymer.

A number of other tumor-specific targets are discussed below. Many of the ligands describe below are either small proteins (about 30-50 amino acid residues) or have a small active site of only a few residues (often 3-7 amino acids) and can be attached to CYSC polymers as used in this invention, for example covalently.

The epidermal growth factor receptor (EGFR) is over-expressed in the majority of colorectal cancers. Also expressed in the gut are gastrointestinal (GI) peptide hormones, such as gastrin, CCK, secretin, glucagon, somatostatin, and their cognate G protein-coupled receptors (GPCRs). EGFR, GI hormones or any related proteins may be used as specific targets by providing a polymer-drug formulation with a ligand, such as a specific antibody, that binds specifically to EGRF or GI hormones or homologous proteins or portions thereof.

A number of leukemias and lymphomas, including cutaneous T-cell lymphoma, chronic lymphocytic leukemia, and B-cell non-Hodgkin's lymphoma, express the interleukin-2 receptor (IL-2R) receptor. Antibodies or other ligands (e.g., DAB389IL-2, ONTAK; Seragen Inc, San Diego, Calif.) targeting the interleukin-2 receptor may be used to target a polymer-drug formulation of the invention.

Monoclonal antibodies directed against CD33, a cell surface antigen highly expressed in acute promyelocytic leukemia (APL) may be used as a targeting ligand with the present invention against APL tumor cells.

Rituximab is an anti-cancer monoclonal antibody that binds to CD20 which is expressed on the surface of malignant B cells. Rituximab may be used as a targeting ligand with the present invention.

Antibodies and other ligands that bind OPG or RANKL, can be used as targeting ligands with the present invention against multiple myeloma tumor cells.

The expression patterns of folate receptor (FR) isoforms, alpha and beta, in normal and malignant male and female reproductive tissues are well studied. Folate, analogues of folate and other ligands that bind to folate receptors can be incorporated into the formulations of the invention to provide specific and/or preferential targeting of various tumor tissues.

Prostate-specific membrane antigen (PSMA) is a metallopeptidase expressed predominantly in prostate cancer (PCa) cells. Ligands that bind to PSMA can be incorporated into the formulations of the invention to provide specific and/or preferential targeting of prostate tumor tissue.

Two protein hormones having activities that are similar to insulin are termed insulin-like growth factor I (IGF-I) and IGF-II. In parallel, there are two receptors, the insulin-like growth factor 1 receptor (IGF1R) and IGF2R that bind with differing affinities to insulin, IGF-I, and IGF-II. IGF2R acts as a cell surface receptor for many proteins relevant to breast cancer biology, including IGF-II. IGF2R could be targeted using sugar moieties and/or polysaccharides attached to the polymers as used by the invention.

Ovarian cancer G protein coupled receptor 1 (OGR1) and GPR4, two structurally related receptors are high affinity molecular targets for SPC. Such receptors for phospholipids on tumors would be ideal targets for polymers as used by the invention coupled to lysophosphatidic acid (LPA), sphingosylphosphorylcholine (SPC), and/or phosphatidic acid (PA). Ligands such as phospholipids that bind to these targets may be incorporated into the formulations of the invention to provide specific and/or preferential targeting of ovarian and other tumor tissue.

Another specific target molecule is fibroblast growth factor (FGF). Activated FGF initiates a kinase cascade resulting in phosphorylation of docking protein fibroblast growth factor receptor substrate 2 (FRS2α). Anti-FGF antibodies of portions of FRS2 domains may serve as ligands for targeting tumors.

Programmed death receptor ligand 1 (PD-L1) is abundant on many cancers. Ligands that bind to PD-L1, such as antibodies or IFN-gamma or related molecules could provide specific and/or preferential targeting of cancer cells and tissues.

The glycolipid-anchored receptor for urokinase-type plasminogen activator (uPA) is overexpressed at the invasive tumor-stromal microenvironment in many human cancers. Ligands that bind to uPA, such as antibodies could be incorporated into the formulations of the invention to provide specific and/or preferential targeting of cancer cells.

CXCR4 is a seven-span transmembrane protein that is a native receptor for the alpha-chemokine stromal-derived factor-1 (SDF-1) that is expressed on the surface of cancer stem cells. The SDF-1-CXCR4 axis is also involved in directing their trafficking/metastasis to organs that highly express SDF-1 (e.g., lymph nodes, lungs, liver, and bones). A region of SDF-1 homologous to the receptor-interacting region could be incorporated into the formulations of the invention to provide specific targeting to cancer cells, particularly to treat or prevent metastasis of tumor cells.

Notch signalling contributes to pre-malignant metaplastic changes that precede pancreatic carcinoma, and it is also likely to be involved in other forms of metaplasia. The Notch receptor ligand can be incorporated into the formulations of the invention to provide specific targeting to pancreatic carcinoma and other cancer cells.

Additionally, other types of ligands may be incorporated into the formulation of the invention including ligands that recognize Receptor Protein Kinases, G-Protein Coupled Receptors, Nuclear Receptors, Ligand-Gated Receptor Ion Channels, Macrophage Scavenger Receptors, T-Cell Receptors, Netrin Receptors, VPS10 Domain Containing Receptors, Tetraspan Family Proteins, Ion Channels, ABC Transporters, Semaphorins and Neuropilins, Membrane Proteins Associated with Intercellular Communication and Peripheral and Anchored Membrane Proteins.

In many of the above cases, the ligand may be an antibody or portion of an antibody (such as the Fab portion or fragment thereof) that binds specifically to the cancer-associated target molecule. Antibodies may be polyclonal or monoclonal and often may be humanized. Such antibodies can be produced by standard well-known methods. Monoclonal antibodies (MAb's) that bind specifically to tumor-associated antigens have been employed in an attempt to target toxin, radionucleotide, and chemotherapeutic conjugates to tumors. To date, a variety of monoclonal antibodies have been developed that induce cytolytic activity against tumor cells. For example, a humanized version of the monoclonal antibody MuMAb4D5, directed to the extracellular domain of P185, growth factor receptor (HER2), is used to treat human breast cancer. Also, a chimeric antibody against CD20, which causes rapid depletion of peripheral B cells, including those associated with lymphoma, is used to treat low-grade B-cell non-Hodgkin's lymphoma. Other humanized and chimeric antibodies under development or in clinical trials include an anti-CD33 antibody that binds to CD-33, which is expressed on most types of myeloid leukemic cells. Another is a chimeric antibody against the leukocyte antigen CD-45 (cHuLym3). The present formulations of the invention may incorporate any target-specific ligands of any kind, including the antibodies and ligands mentioned herein, and any derivatives and homologues thereof.

Some Advantages of Invention

Embodiments of the invention have advantages that result inter alia from the fact that preferred CYSC polymers can comprise a desired balance of hydrophobic and/or hydrophilic moieties which can be selected to associate with a wide range of drugs through chemical and/or physical bonds, thus providing formulations which can be delivered to mammal or cells in a wide variety of ways. The CYSC can have sharp and relatively low melting points; can have a desired molecular weight; do not have any adverse effect on mammal or cells; and can be eliminated from mammal or cells after the drug mixed with the CYSC polymer has been delivered to the mammal or cell. Advantages include 1) The ability of preferred CYSC polymers to be easily mixed and processed with drugs. 2) The ability of preferred CYSC polymers to provide formulations meeting desired mixing, loading and delivery requirements, for example maximized loadings of drugs, minimized burst effect, sustained delivery of therapeutically effective levels of drug, delivery of a drug to selected parts of an mammal or cell, optionally after a selected time after ingestion or application.

One specific example of a formulation containing the psychoactive (antipsychotic) agent Risperidone, (4-[2-[4-(6-fluorobenzo[d]isoxazol-3-yl)-1-piperidyl]ethyl]-3-methyl-2,6-diazabicyclo[4.4.0]deca-1,3-dien-5-one) is the following. Risperidone may be physically mixed with a CYSC polymer, or may be pre-associated, for example with a surfactant, PEG, human (or bovine etc) serum albumin, or with proteins etc to provide immunological shielding, increased half-life, and improved bioavailability. The formulation may be formed into a shaped solid implant suitable for introduction, e.g. by trocar, under the skin or intramuscularly or by injection above the formulation's melting temperature. It is believed that a dose of Risperidone of about 4 mg/day is sufficient to prevent psychotic episodes in many patients. Individual variations in tolerance and effectiveness, however, can be wide. Therefore the current invention may be formulated to supply from 1 to 60 mg/day over a period of 1 to 200 days. The advantage of an implanted dosage form is increased compliance, which with psychosis, is a major issue. In one embodiment, at least 50 mg of Risperidone is formulated into a single implantable dosage form by mixing the drug in powdered form with a CYSC polymer at a temperature above the Tm of the polymer, example at between 42° C. and 60° C. No solvent is required. The mixture is cooled and shaped into solid elongated or approximately spherical implants. In other embodiments, the amount of Risperidone formulated into a single implantable dosage form may be at least 100 mg, or at least 200 mg, or at least 500 mg, or at least 1000 mg, or at least 1500 mg, or at least 2000 mg. In some dosage forms, the total amount of drug may be up to 3, 4 or 5 grams.

The Risperidone implant is introduced subcutaneously into a subject using a trocar. The implant releases Risperidone at an average rate of between 1 and 60 mg (for example no more than 1, 2, 3, 4, 5, 7, 10, 20, 40, 80, 120, 200, or 300 mg) per day over a period of at least 5, 10, 15, 20, 25, 30, 40, 60 or 90 days. In one exemplary embodiment the implant releases Risperidone at an average rate of between 4 and 12 mg per day over a period of at least 7 days. During this period, a desired therapeutic effect is provided for at least 75% of the time. The implant is then removed, or may be left in to erode over time. If a larger bolus of drug is desired, the local area of skin above the implant may be heated by any convenient means.

In other embodiments the implant releases Risperidone at an average rate of between 1 and 20 mg per day, or 3 and 100 mg per day or 4 and 30 mg per day over a period of at least 7 days or at least 14, 21, 30, 45, 60 or 90 days.

In certain related embodiments, Risperidone may be pre-associated with a surfactant, PEG, human serum albumin or with proteins. In another embodiment, the CYSC polymer comprises side chains having an average length of, for example, between 6 and 50 monomer units. In another embodiment, the CYSC polymer has side chains with an average length of between about 12 and 50 alkyl ester acrylate or methacrylate monomer units.

In another embodiment, the proportion of drug to crystalline polymer is between 5% by weight and 30% by weight, or at least 5% by weight, at least 10% by weight, at least 15% by weight, at least 20% by weight, at least 25% by weight, at least 30% by weight, at least 35% by weight, at least 40% by weight, or at least 50% by weight, In certain embodiments, Risperidone is physically mixed with the polymer and no covalent or ionic bonds are formed between the drug and the polymer. In some embodiments, the drug associates with the polymer via hydrogen bonds and/or van der Waals forces. In various alternative embodiments Risperidone is associated with the CYSC polymer by electrostatic bonds, by hydrogen bonds, van der Waals forces or a combination of one or more of these effects. This exemplary embodiment may be applied to any number or drugs.

In another embodiment designed to release a drug to control pain, the drug of the formulation may be an opioid, opioid antagonist, synthetic opioid, morphine, fentanyl or sufentanyl, or any type of local or systemic analgesic acting on peripheral or central nervous pair receptors. In such embodiments, the polymer may be implanted under the skin such that the drug is released over a period of time to treat pain for a number of hours such as at least 3, at least 6 or at least 12 hours. The formulation may also be an oral formulation, transdermal formulation or depot.

In some embodiments, the formulation is part of a transdermal drug delivery device such as a patch, wherein the drug, mixed into the CYSC polymer, is released from a patch placed against the skin. The formulation may be made to release the drug steadily or increasingly or decreasingly over a period of time, or may be made to release drug in intermittent boluses in response to a stimulus such as heat. For sustained delivery a drug will not be released immediately as a bolus but will be released from the polymer over time in a generally sigmoid pattern, providing a desired therapeutic delivery, e.g. to treat pain over a desired time, such as over at least 1, at least 3, at least 6 or at least 12, 24, 36, or 48 hours. In other embodiments, the drug may be delivered with approximately first order kinetics, over at least a certain desired time (e.g., over at least 1, at least 3, at least 6, or at least 12, 24, 36 or 72 hours). In such embodiments, the drug is released from the polymer, and the polymer is not transported across the skin.

The release of drug may be induced or increased by the application of heat to the device. The device may be heated by a separate heating device or by an integral heating unit. The amount of drug released from the formulation will depend on the duration of heating and the temperature of the device. Heat-induced drug release may be controlled by the physician, either directly or remotely, or by the patient. This provides controlled self-administration of drug to treat pain and other conditions when needed. The drug released from the formulation may be released onto the surface of the skin, and will then penetrate the skin by various means. Generally transdermal delivery relies on passive diffusion across skin membranes, but penetration may also be improved by using solvents or enhancers such as water, ethanol (EtOH) and l-menthol (LM) that modify the properties of the outermost layers of the skin, or on the use of electrical or thermal technologies to "push" drugs through the skin. Any such means may be used in the present invention, either mixed with the polymer or separate from the polymer. Delivery rates of an opioid such as fentanyl may for example range from about 1.0 to 1000 ng/cm$^2$/hr following application of a transdermal patch.

A transdermal formulation may be made by mixing the CYSC polymer and drug, optionally with an adhesive component, and retaining the formulation produced in or on a flexible film to produce a patch. The flexible impermeable film forms the backing of the patch, and the formulation side to be applied to the skin may be covered with a removable cover, which is removed prior to application to the skin. The formulation side includes at least some adhesive portion, generally on the periphery of the patch so that when applied, the patch forms a seal against the skin, isolating the formulation from the environment. Such embodiments exclude "gating" devices wherein a drug is maintained in a reservoir and is separated from the skin by a polymer membrane the permeability of which may be altered to allow drug delivery. The present invention does not include a drug reservoir separated from the skin by a polymer firm. In the present invention, the drug is integrally mixed together with the CYSC polymer to form a drug-polymer formulation. Heat may be produced by chemical or electrical means, or even by physical means such as rubbing with the hand to produce friction-induced heat. The heating element may be functionally linked to a control (lock-out) element that prevents activation without permission, such as by use of a radio frequency signal to control the activation of an electrical heat-generating circuit.

TABLE 3

Polymer-Drug Formulations.

| | Polymer | | | | | | | | | |
|---|---|---|---|---|---|---|---|---|---|---|
| | I | II | III | IV | V | VI | VII | VIII | IX | X |
| Atorvastatin | N | H | H | I | I | I | I | N | N | H |
| Symvastatin | N | H | H | N | N | N | N | H | H | H |
| Celecoxib | N | H | H | H | H | H | H | N | N | N |
| Sertraline | N | I | I | N | N | H | H | N | N | N |
| Omeprazole | N | I | I | H | H | H | H | N | N | N |
| Esomeprazole | N | I | I | H | H | H | H | N | N | N |
| Pravastatin | N | H | H | I | I | I | I | N | N | H |
| Azithromycin | N | I | I | N | N | H | H | N | N | N |
| Quetiapine | N | I | I | N | N | H | H | N | N | N |
| Metoprolol | N | I | I | N | N | H | H | N | N | N |
| Budesonide | N | H | H | N | N | N | N | H | H | H |
| Clarithromycin | N | I | I | N | N | H | H | N | N | N |
| Paroxetine | N | I | I | N | N | H | H | N | N | N |
| Oxycodone | N | I | I | N | N | H | H | N | N | N |
| Risperidone | N | I | I | N | N | H | H | N | N | N |
| Alendronate | N | I | I | N | N | H | H | N | N | N |
| Venlafaxine | N | I | I | N | N | H | H | N | N | N |
| Amlodipine | N | I | I | N | N | H | H | N | N | N |
| Olanzapine | N | I | I | N | N | H | H | N | N | N |
| Lansoprazole | N | I | I | N | N | H | H | N | N | N |
| Fluoxetine | N | I | I | N | N | H | H | N | N | N |
| Finasteride | N | H | H | H | H | H | H | N | N | H |
| Sildenafil | N | I | I | N | N | H | H | N | N | N |
| Rosuvastatin | N | H | H | I | I | I | I | N | N | H |
| Methotrexate | N | I | I | I | I | I | I | N | N | H |
| Doxyrubicin | N | I | I | I | I | I | I | N | N | H |
| Nicotine | N | I | I | N | N | H | H | N | N | N |
| Fentanyl | N | I | I | N | N | H | H | N | N | N |
| Paclitaxel | N | H | H | H | H | H | H | N | N | H |
| Cis-platin | N | L | L | L | L | L | L | N | N | N |
| Fluorouracil | N | I | I | H | H | H | H | N | N | N |
| Ibuprofen | N | H | H | I | I | I | I | N | N | H |
| Aspirin | N | H | H | I | I | I | I | N | N | H |
| Dexamethasone | N | H | H | H | H | H | H | N | N | H |
| Leuprolide | N | I | I | I | I | I | I | N | N | H |

(N = neutral polymer-drug interaction; H = hydrogen bonded polymer-drug interaction; I = ionic polymer-drug attachment; L = ligand attached polymer-drug interaction)

EXAMPLES

The invention is illustrated in the following Examples. Many of the Examples are summarized in Tables 1A, 1B and 1C below. A detailed explanation of Tables 1A, 1B and 1C follows the tables.

TABLE 1A

| | Example No. | 1A | 2A | 3A | 4A | 5A | 6A | 7A |
|---|---|---|---|---|---|---|---|---|
| 1 | CYSC molar ratio | | | | | | | |
| | C18A | Only | 4 | 1 | 4 | 4 | 1.2 | 4 |
| | C22A | | | | | | 2.8 | |
| | AA | | 1 | 4 | 1 | | | |
| | PEG6A | | | | 1 | | | |
| | PEG6-MA | | | | | | 1 | |
| | DMAEA | | | | | 1 | | |
| | DMAEMA | | | | | | 1 | |
| | DMAEA quat | | | | | | | 1 |
| 2 | Mw | 3491 | 3012 | 4241 | 3310 | 8876 | 1294850 | 56,825 |
| 3 | Mn | 2546 | 2154 | 3376 | 2342 | 7917 | 304,300 | 49,275 |
| 4 | DSC 1st heat Tp | 50.64 | 51.83 | 44.24 | 45.50 | 46.90 | 55.07 | 56.35 |
| | 1st heat To | 48.26 | 49.11 | 37.88 | 41.68 | 45.39 | 49.91 | 53.83 |
| | 2nd heat Tp | 47.06 | 47.55 | 27.90 | 42.06 | 42.85 | 48.94 | 51.69 |
| | 2nd heat To | 42.22 | 42.92 | 9.6 | 33.39 | 37.70 | 36.07 | 47.62 |

| | Example No. | 1B | 2B | 3B | 4B | 5B | 6B | 7B |
|---|---|---|---|---|---|---|---|---|
| 5 | Sol. In Miglyol (18.97) | Yes | Yes | No | Yes | Yes | Yes | Yes |
| | EtAc (21.02) | Yes | Yes | Yes | Yes | Yes | Yes | Yes |
| | NMP (23.12) | Yes | Yes | Yes | Yes | Yes | Yes | Yes |
| | $H_2O$ (48.00) | No | No | Yes | No | No | No | No |
| 6 | Gel form'n in Miglyol | Yes | Yes | No | Yes | Yes | Yes | Yes |
| | EtAC | Yes | Yes | Yes | Yes | Yes | No | Yes |
| | NMP | Yes | Yes | No | Yes | Yes | Yes | Yes |
| | $H_2O$ | No | No | Yes | No | No | No | No |
| 7 | Solubility parameter | 17.17 | 17.31 | 19.14 | 17.50 | 17.31 | 17.43 | 18.09 |

| | Example No. | 1C | 2C | 3C | 4C | 5C | 6C | 7C |
|---|---|---|---|---|---|---|---|---|
| 8 | CYSC/dcl/IPA (9.1%) uniform? | No | Yes | Yes | Yes | No | Yes | Yes |
| 9 | DSC 1st heat Tp | | 49.6 | 42.8 | 47.2 | | 52.7 | 45.9 |
| | 1st heat To | | 45.3 | 40.5 | 43.9 | | 47.2 | 39.1 |
| | 2nd heat Tp | | 43.8 | 40.2 | 41.6 | | 49.4 | 48.3 |
| | 2nd heat To | | 38.7 | 29.1 | 32.9 | | 36.2 | 40.7 |

| | Example No. | 1D | 2D | 3D | 4D | 5D | 6D | 7D |
|---|---|---|---|---|---|---|---|---|
| 10 | dcl/CYSC/NMP10/50/50 (9.1%) uniform gel? | No | No | No | Yes | No | No | No |

| | Example No. | 1E | 2E | 3E | 4E | 5E | 6E | 7E |
|---|---|---|---|---|---|---|---|---|
| 11 | dcl/CYSC/NMP10/10/90 (9.1%) uniform gel? | No | No | No | No | No | No | No |

| | Example No. | 1F | 2F | 3F | 4F | 5F | 6F | 7F |
|---|---|---|---|---|---|---|---|---|
| 12 | dcl/CYSC/IPA 2/10/7 (16.7%) miscible? | No | Yes | Yes | Yes | No | Yes | Yes |
| 13 | dcl/CYSC/IPA 3/10/7 (23.1%) miscible? | | Yes | Yes | Yes | | No | No |

| | Example No. | 1I | 2I | 3I | 4I | 5I | 6I | 7I |
|---|---|---|---|---|---|---|---|---|
| 14 | Dcl/CYSC 1/10 (9.1%) uniform? | Yes | | | | Yes | | |

| | Example No. | 1J | 2J | 3J | 4J | 5J | 6J | 7J |
|---|---|---|---|---|---|---|---|---|
| 15 | rsp/CYSC/IPA 1/10/40 (9.1%) uniform? | No | Yes | Yes | Yes | No | No | No |
| 16 | DSC 1st heat Tp | | 50.0 | 38.0 | 45.4 | | | |
| | 1st heat To | | 45.0 | 30.6 | 40.3 | | | |
| | 2nd heat Tp | | 42.7 | 35.8 | 40.5 | | | |
| | 2nd heat To | | 36.8 | 28.9 | 32.3 | | | |

| | Example No. | 1K | 2K | 3K | 4K | 5K | 6K | 7K |
|---|---|---|---|---|---|---|---|---|
| 17 | rsp/CYSC/IPA 2/10/80 (16.7%) uniform? | | Yes | No | No | | | |

TABLE 1A-continued

| Example No. | | 1N | 2N | 3N | 4N | 5N | 6N | 7N |
|---|---|---|---|---|---|---|---|---|
| 18 | rsp/CYSC 10/90 melt (9.1%) uniform? | Yes | No | Yes | | Yes | | |

| Example No. | | 1S | 2S | 3S | 4S | 5S | 6S | 7S |
|---|---|---|---|---|---|---|---|---|
| 19 | prav/CYSC/IPA 1/10/40 (9.1%) uniform? | Yes | Yes | Yes | Yes | Yes | Yes | Yes |
| 20 | DSC 1st heat Tp | 47.80 | 51.09 | 44.56 | 46.85 | 48.25 | 55.09 | 54.84 |
|    | 1st heat To | 44.15 | 48.73 | 36.84 | 44.48 | 46.40 | 40.60 | 51.07 |
|    | 2nd heat Tp | 46.64 | 46.98 | 42.63 | 43.02 | 44.04 | 54.14 | 50.23 |
|    | 2nd heat To | 42.51 | 42.59 | 34.74 | 33.18 | 38.92 | 38.25 | 42.97 |

| Example No. | | 1T | 2T | 3T | 4T | 5T | 6T | 7T |
|---|---|---|---|---|---|---|---|---|
| 21 | dexa/CYSC/IPA 1/10/40 (10%) uniform? | No | No | Yes | No | No | No | No |
| 22 | DSC 1st heat Tp | | | 44.00 | | | | |
|    | 1st heat To | | | 36.01 | | | | |
|    | 2nd heat Tp | | | 19.84 | | | | |
|    | 2nd heat To | | | 6.43 | | | | |
| 23 | dexa/CYSC 1/10 (9.1%) melt. uniform? | | Yes | | Yes | | | Yes |
| 24 | DSC 1st heat Tp | | 49.41 | | 45.63 | | | 55.67 |
|    | 1st heat To | | 45.71 | | 41.78 | | | 50.26 |
|    | 2nd heat Tp | | 47.00 | | 42.35 | | | 52.94 |
|    | 2nd heat To | | 43.15 | | 33.02 | | | 47.02 |

| Example No. | | 1W | 2W | 3W | 4W | 5W | 6W | 7W |
|---|---|---|---|---|---|---|---|---|
| 25 | tacro/CYSC/IPA 1/10/40 (9.1%) uniform? | Yes | Yes | Yes | Yes | Yes | Yes | Yes |
| 26 | DSC 1st heat Tp | 49.42 | 50.46 | 43.67 | 47.37 | 48.71 | 54.55 | 53.44 |
|    | 1st heat To | 46.45 | 46.94 | 37.53 | 44.01 | 45.06 | 51.68 | 48.47 |
|    | 2nd heat Tp | 46.25 | 46.43 | 30.71 | 41.91 | 39.56 | 51.74 | 50.25 |
|    | 2nd heat To | 41.71 | 41.99 | 15.78 | 34.74 | 44.27 | 37.67 | 44.17 |

TABLE 1B

| Example No. | | 8A | 9A | 10A | 11A | 12A | 13A | 14A |
|---|---|---|---|---|---|---|---|---|
| 1 | CYSC molar ratio | | | | | | | |
|   | C18A | 4 | 3 | 4 | 3 | 2.5 | 3 | 2.8 |
|   | C16A | | | | | | | |
|   | C22A | | 1 | | 1 | 1.5 | 1 | 1.2 |
|   | PEG12-OCH3MA | | | | | | 1 | |
|   | PEG23-OCH3MA | | | | 1 | | | |
|   | PEG6MA | | 1 | | | | | |
|   | PEG25-C22MA | | | | | | | 1 |
|   | PEG46-OCH3MA | | | | | 1 | | |
|   | PEG9-OCH3MA | | | 1 | 1 | | | |
|   | DMAEMA quat | 1 | | | | | | |
| 2 | Mw | 67,545 | 3046 | 3459 | 60,845 | 17,785 | 3281 | 4597 |
| 3 | Mn | 49,745 | 2220 | 2490 | 21,378 | 6542 | 2064 | 2166 |
| 4 | DSC 1$^{st}$ heat Tp | 49.57 | 47.48 | 45.73 | 49.08 | 51.02 | 48.19 | 48.50 |
|   | 1$^{st}$ heat To | 47.00 | 45.76 | 42.08 | 41.74 | 45.04 | 45.30 | 41.98 |
|   | 2$^{nd}$ heat Tp | 45.41 | 40.57 | 41.87 | 45.61 | 48.86 | 42.38 | 45.96 |
|   | 2$^{nd}$ heat To | 37.33 | 33.03 | 32.55 | 34.17 | 45.26 | 34.30 | 34.26 |

| Example No. | | 8B | 9B | 10B | 11B | 12B | 13B | 14B |
|---|---|---|---|---|---|---|---|---|
| 5 | Sol. In Miglyol (18.97) | Yes | Yes | Yes | Yes | Yes | Yes | Yes |
|   | EtAc (21.02) | Yes | Yes | Yes | Yes | Yes | Yes | Yes |
|   | NMP (23.12) | Yes | Yes | Yes | Yes | Yes | Yes | Yes |
|   | H$_2$O (48.00) | Yes | No | No | Yes | Yes | No | No |
| 6 | Gel form'n in Miglyol | Yes | Yes | Yes | Yes | Yes | Yes | Yes |
|   | EtAC | Yes | No | Yes | No | No | Yes | Yes |
|   | NMP | Yes | Yes | Yes | Yes | Yes | Yes | Yes |
|   | H$_2$O | No | No | No | No | No | No | No |
| 7 | Solubility parameter | 18.06 | 17.36 | 17.32 | 17.49 | 17.61 | 17.40 | 17.38 |

| Example No. | | 8C | 9C | 10C | 11C | 12C | 13C | 14C |
|---|---|---|---|---|---|---|---|---|
| 8 | CYSC/dcl/IPA (9.1%) uniform? | Yes | Yes | Yes | Yes | Yes | Yes | Yes |

TABLE 1B-continued

| | | | | | | | | |
|---|---|---|---|---|---|---|---|---|
| 9 | DSC | 1st heat Tp | 46.3 | 47.2 | 45.4 | 48.6 | 49.9 | 47.7 | 49.8 |
| | | 1st heat To | 39.2 | 44.0 | 42.2 | 43.3 | 33.8 | 41.8 | 37.2 |
| | | 2nd heat Tp | 43.0 | 42.3 | 41.4 | 46.7 | 44.6 | 44.6 | 46.3 |
| | | 2nd heat To | 37.1 | 34.4 | 32.5 | 34.4 | 39.6 | 34.6 | 40.1 |
| Example No. | | | 8D | 9D | 10D | 11D | 12D | 13D | 14D |
| 10 | CYSC/dcl/NMP 10/50/50 (9.1%) uniform gel? | | Yes | No | No | Yes | Yes | Yes | Yes |
| Example No. | | | 8E | 9E | 10E | 11E | 12E | 13E | 14E |
| 11 | dcl/CYSC/NMP10/10/90 (9.1%) uniform gel? | | No | No | No | Yes | Yes | Yes | Yes |
| Example No. | | | 8F | 9F | 10F | 11F | 12F | 13F | 14F |
| 12 | dcl/CYSC/IPA 2/10/7 (16.7%) miscible? | | Yes | Yes | Yes | Yes | Yes | Yes | Yes |
| 13 | dcl/CYSC/IPA 3/10/7 (23.1%) miscible? | | Yes | Yes | Yes | Yes | Yes | Yes | Yes |
| Example No. | | | 8I | 9I | 10I | 11I | 12I | 13I | 14I |
| 14 | Dcl/CYSC 1/10 (9.1%) uniform? | | | | | | | | |
| Example No. | | | 8J | 9J | 10J | 11J | 12J | 13J | 14J |
| 15 | rsp/CYSC/IPA 1/10/40 (9.1%) uniform? | | No | No | No | No | No | No | No |
| 16 | DSC | 1st heat Tp | | | | | | | |
| | | 1st heat To | | | | | | | |
| | | 2nd heat Tp | | | | | | | |
| | | 2nd heat To | | | | | | | |
| Example No. | | | 8K | 9K | 10K | 11K | 12K | 13K | 14K |
| 17 | rsp/CYSC/IPA 2/10/80 (16.7%) uniform? | | | | | | | | |
| Example No. | | | 8N | 9N | 10N | 11N | 12N | 13N | 14N |
| 18 | rsp/CYSC 10/90 melt (9.1%) uniform? | | | | | | | | |
| Example No. | | | 8S | 9S | 10S | 11S | 12S | 13S | 14S |
| 19 | prav/CYSC/IPA 1/10/40 (9.1%) uniform? | | Yes | Yes | Yes | Yes | Yes | Yes | Yes |
| 20 | DSC | 1st heat Tp | 47.68 | 47.89 | 47.18 | 52.65 | 52.75 | 48.27 | 50.61 |
| | | 1st heat To | 39.15 | 42.52 | 35.17 | 34.04 | 37.26 | 37.68 | 46.22 |
| | | 2nd heat Tp | 44.41 | 44.65 | 44.20 | 51.16 | 53.17 | 45.46 | 47.59 |
| | | 2nd heat To | 32.24 | 35.37 | 32.65 | 38.06 | 36.46 | 35.98 | 35.63 |
| Example No. | | | 8T | 9T | 10T | 11T | 12T | 13T | 14T |
| 21 | dexa/CYSC/IPA 1/10/40 (10%) uniform? | | No | No | No | No | No | No | No |
| 22 | DSC | 1st heat Tp | | | | | | | |
| | | 1st heat To | | | | | | | |
| | | 2nd heat Tp | | | | | | | |
| | | 2nd heat To | | | | | | | |
| 23 | dexa/CYSC 1/10 (9.1%) melt. Uniform? | | | | Yes | | | | |
| 24 | DSC | 1st heat Tp | | | 44.39 | | | | |
| | | 1st heat To | | | 41.79 | | | | |
| | | 2nd heat Tp | | | 39.77 | | | | |
| | | 2nd heat To | | | 32.70 | | | | |
| Example No. | | | 8W | 9W | 10W | 11W | 12W | 13W | 14W |
| 25 | tacro/CYSC/IPA 1/10/40 (9.1%) uniform? | | Yes | Yes | Yes | Yes | Yes | Yes | Yes |
| 26 | DSC | 1st heat Tp | 50.20 | 47.85 | 44.69 | 48.22 | 42.87 | 46.89 | 49.49 |
| | | 1st heat To | 44.92 | 45.53 | 42.20 | 45.47 | 50.25 | 42.91 | 42.32 |
| | | 2nd heat Tp | 45.35 | 42.56 | 39.35 | 34.61 | 40.92 | 43.70 | 46.33 |
| | | 2nd heat To | 39.93 | 34.16 | 32.02 | 38.64 | 35.74 | 34.72 | 34.20 |

TABLE 1C

| | Example No. | 15A | 16A | 17A | 18A | 19A | 20A |
|---|---|---|---|---|---|---|---|
| 1 | CYSC molar ratio | | | | | | |
| | C18A | 4 | 4 | 4 | 4 | 1 | 4 |
| | AA | | | | | 1 | 1 |
| | PEG6-OH A | 1 | | | | | |
| | PPG6-OH A | | 1 | | | | |
| | PEG6MA | | | | | 1 | 1 |
| | 2-HEA | | | 1 | | | |
| | VP | | | | 1 | | |
| | HEMA | | | | | 1 | 1 |
| | Acrylamide | | | | | 1 | |
| 2 | Mw | 3155 | 2419 | 3058 | 3183 | 806 | 4563 |
| 3 | Mn | 1938 | 1568 | 2199 | 2318 | 464 | 3049 |
| 4 | DSC | | | | | | |
| | 1st heat Tp | 47.82 | 44.94 | 49.32 | 46.64 | 43.15 | 47.78 |
| | 1st heat To | 44.17 | 41.46 | 46.05 | 44.71 | 37.60 | 41.39 |
| | 2nd heat Tp | 43.33 | 42.17 | 45.77 | 43.96 | 41.96 | 44.08 |
| | 2nd heat To | 37.68 | 35.27 | 42.05 | 40.02 | 38.64 | 38.8 |

| | Example No. | 15B | 16B | 17B | 18B | 19B | 20B |
|---|---|---|---|---|---|---|---|
| 5 | Sol. in  Miglyol (18.97) | Yes | Yes | Yes | Yes | No | Yes |
| | EtAc (21.02) | Yes | Yes | Yes | Yes | Yes | Yes |
| | NMP (23.12) | Yes | Yes | Yes | Yes | Yes | Yes |
| | $H_2O$ (48.00) | No | No | No | No | No | No |
| 6 | Gel form'n in  Miglyol | Yes | Yes | Yes | Yes | No | Yes |
| | EtAC | Yes | Yes | Yes | Yes | Yes | Yes |
| | NMP | Yes | Yes | Yes | Yes | No | Yes |
| | $H_2O$ | No | No | No | No | No | No |
| 7 | Solubility parameter | 17.61 | 17.36 | 17.56 | 17.26 | 19.31 | 18.14 |

| | Example No. | 15C | 16C | 17C | 18C | 19C | 20C |
|---|---|---|---|---|---|---|---|
| 8 | CYSC/dcl/IPA (9.1%) uniform? | Yes | No | No | No | Yes | Yes |
| 9 | DSC  1st heat Tp | 46.9 | | | | 41.6 | 49.2 |
| | 1st heat To | 45.8 | | | | 35.5 | 43.5 |
| | 2nd heat Tp | 43.6 | | | | 41.1 | 44.1 |
| | 2nd heat To | 37.9 | | | | 37.8 | 39.2 |

| | Example No. | 15D | 16D | 17D | 18D | 19D | 20D |
|---|---|---|---|---|---|---|---|
| 10 | CYSC/dcl/NMP 10/50/50 (9.1%) uniform gel? | No | No | No | No | Yes | Yes |

| | Example No. | 15E | 16E | 17E | 18E | 19E | 20E |
|---|---|---|---|---|---|---|---|
| 11 | dcl/CYSC/NMP10/10/90 (9.1%) uniform gel? | No | No | No | No | No | Yes |

| | Example No. | 15F | 16F | 17F | 18F | 19F | 20F |
|---|---|---|---|---|---|---|---|
| 12 | dcl/CYSC/IPA 2/10/7 (16.7%) miscible? | Yes | | | | Yes | Yes |
| 13 | dcl/CYSC/IPA 3/10/7 (23.1%) miscible? | No | | | | Yes | Yes |

| | Example No. | 15I | 16I | 17I | 18I | 19I | 20I |
|---|---|---|---|---|---|---|---|
| 14 | Dcl/CYSC 1/10 (9.1%) uniform? | | Yes | Yes | Yes | | |

| | Example No. | 15J | 16J | 17J | 18J | 19J | 20J |
|---|---|---|---|---|---|---|---|
| 15 | rsp/CYSC/IPA 1/10/40 (9.1%) uniform? | No | No | No | No | Yes | Yes |
| 16 | DSC  1st heat Tp | | | | | 47.4 | 43.5 |
| | 1st heat To | | | | | 42.1 | 40.7 |
| | 2nd heat Tp | | | | | 43.6 | 42.2 |
| | 2nd heat To | | | | | 31.3 | 37.2 |

| | Example No. | 15K | 16K | 17K | 18K | 19K | 20K |
|---|---|---|---|---|---|---|---|
| 17 | rsp/CYSC/IPA 2/10/80 (16.7%) uniform? | | | | | No | No |

TABLE 1C-continued

| Example No. | | 15N | 16N | 17N | 18N | 19N | 20N |
|---|---|---|---|---|---|---|---|
| 18 rsp/CYSC 10/90 melt (9.1%) uniform? | | | Yes | | Yes | | |

| Example No. | | 15S | 16S | 17S | 18S | 19S | 20S |
|---|---|---|---|---|---|---|---|
| 19 prav/CYSC/IPA 1/10/40 (10%) uniform? | | Yes | Yes | Yes | Yes | Yes | Yes |
| 20 DSC | 1st heat Tp | 50.66 | 46.13 | 50.32 | 49.73 | 48.37 | 50.34 |
| | 1st heat To | 40.36 | 34.90 | 41.09 | 43.52 | 45.45 | 45.36 |
| | 2nd heat Tp | 44.65 | 45.54 | 48.68 | 45.83 | 43.73 | 45.56 |
| | 2nd heat To | 37.10 | 33.33 | 41.58 | 40.91 | 39.77 | 39.39 |

| Example No. | | 15T | 16T | 17T | 18T | 19T | 20T |
|---|---|---|---|---|---|---|---|
| 21 dexa/CYSC/IPA 1/10/40 (10%) uniform? | | No | No | No | No | Yes | No |
| 22 DSC | 1st heat Tp | | | | | 46.91 | |
| | 1st heat To | | | | | 43.35 | |
| | 2nd heat Tp | | | | | 49.24 | |
| | 2nd heat To | | | | | 39.31 | |
| 23 dexa/CYSC 1/10 (9.1%) melt | | | | Yes | Yes | | Yes |
| 24 DSC | 1st heat Tp | | | 48.99 | 48.41 | | 26.17 |
| | 1st heat To | | | 44.82 | 45.38 | | 42.67 |
| | 2nd heat Tp | | | 46.32 | 45.22 | | 44.31 |
| | 2nd heat To | | | 42.14 | 40.55 | | 37.44 |

| Example No. | | 15W | 16W | 17W | 18W | 19W | 20W |
|---|---|---|---|---|---|---|---|
| 25 tacro/CYSC/IPA 1/10/40 (9.1%) uniform? | | Yes | Yes | Yes | Yes | Yes | Yes |
| 26 DSC | 1st heat Tp | 46.34 | 45.75 | 47.88 | 49.12 | 45.95 | 47.14 |
| | 1st heat To | 43.17 | 43.40 | 46.36 | 44.33 | 42.28 | 36.21 |
| | 2nd heat Tp | 43.74 | 43.09 | 45.36 | 44.97 | 42.49 | 43.84 |
| | 2nd heat To | 38.48 | 36.33 | 41.11 | 40.39 | 39.97 | 39.69 |

The CYSC polymers described in the Examples were prepared by solution polymerization of the monomers in IPA at about 80° C. for 3 hours under a nitrogen blanket with 0.1% AIBN. BMP (6%) was used to control the molecular weight under 10,000, e.g. around 5000. IPA was removed under reduced pressure at elevated temperature. At the end of the reduced pressure stage, the internal temperature reached 120-130° C. and, in all the examples except Example 3A, 0.5 g of Trigonox was added. The reaction was continued at 120-130° C. for at least 1 hr, followed by 1 hr under reduced pressure. In Example 7A, one of the components of the polymer was DMAEA quat, and the polymer was prepared by converting the amine polymer of Example 5A into the quaternary ammonium salt by reaction with dimethyl sulphate in MiBK at 1/1 molar ratio (50-55° C., 3 hours) followed by removal of MiBK under reduced pressure at elevated temperature. Similarly, the polymer of Example 8A, which contains DMAEMA quat, was prepared by converting the amine polymer of Example 6 into the quaternary ammonium salt.

Tables 1A, 1B and 1C summarize the preparation and testing of 20 CYSC polymers 1A-20A. The polymers were prepared by the procedure described above, using the monomers, and the molar amounts thereof, shown in line 1 of Tables 1A, 1B and 1C.

Lines 2, 3 and 4 in Tables 1A, 1B and 1C show the values of Mw and Mn, and the DSC test results, for each of the 20 polymers. Lines 5 and 6 show shows the behavior of the polymers in four solvents with various polarities at 10% loading at 70° C. and room temperature (RT) respectively. The solubility parameters of the solvents are shown in parentheses in the Table. A typical procedure was to weigh 0.5 g of polymer and 4.5 g solvent into a 20 ml vial, followed by heating in a 70° C. oven for 10 to 15 min. The mixture was shaken by hand while warm. Lines 5, 6 and 7 (Examples 1B-20B) show respectively (line 5) whether the polymer dissolved at 70° C., (line 6) whether a uniform gel was formed after cooling to room temperature, and (line 7) the calculated solubility parameters of the CYSC polymers.

Lines 8 and 9 (Examples 1C-20C) in Tables 1A, 1B and 1C show the results of mixing the polymers with diclofenac sodium (dcl). The mixtures were prepared at 9.1% drug loading by mixing dcl with the polymer in IPA at the ratio of dcl/polymer/IPA=1/10/35 at 70° C., followed by evaporation of IPA in a 70° C. oven. A dry mixture was obtained by removing residual IPA under reduced pressure at 70° C. As noted in line 8, the mixtures were uniform except when using the polymers of Examples 1A, 5A, 16A, 17A and 18A. Line 9 shows the results of DSC examination of the uniform mixtures. A typical release sample of each of these 15 uniform mixtures and other mixtures in subsequent examples was prepared as a thin flat disc in a 20 ml scintillation vial (28×61 mm=OD×H) by loading 0.5 gram of the drug/polymer mixture into the vial and warming to 60-70° C., allowing the mixture to flow and fuse together. This resulted, after cooling, in a solid thin disc with a smooth uniform surface.

Line 10 (Examples 1D-20D) shows the results of preparing gel mixtures containing dcl, CYSC polymer and NMP at 10/50/50. Eight of the polymers formed uniform gels at RT.

Line 11 (Examples 1E-20E) shows the results of preparing mixtures containing dcl (9.1%), CYSC polymer NMP at the ratio of 10/10/90. Six of the 20 polymers (8A, 11A, 12A, 13A, 14A and 20A) formed a uniform gel at RT. Examples 1D-20D and 1E-20E demonstrate the effect of NMP on release rate.

Lines 12 and 13 (Examples 1F-20F) show the results of using the 15 polymers which formed uniform mixtures in Examples 1C to 20C, to prepare compositions containing more than 10% of dcl using the same process as in Examples 1C to 20C. For 16.7% and 23.1% loading, mixtures of dcl/

CYSC polymer/IPA in ratios of 2/10/70 and 3/10/100 respectively were prepared at 70° C. After IPA was removed, all the tested CYSC polymers were miscible with dcl at 16.7% and 12 of them at 23.1%. Polymers 6A, 7A and 15A were not miscible and did not yield uniform mixtures.

Examples 2F1-2F7

The polymer of Example 2A was used to produce uniform dry mixtures having loadings of up to 37.5% of dcl, using the same process as in Examples C1-C, as shown in Table F1 below.

TABLE F1

| Example | Dcl g | Ex 2A pol g | IPA g | % dcl on polymer | % dcl on composition |
|---|---|---|---|---|---|
| 1F | 0.15 | 3.0 | 5.25 | 5.0 | 4.8 |
| 2F | 0.30 | 3.0 | 10.50 | 10.0 | 9.1 |
| 3F | 0.60 | 3.0 | 21.00 | 20.0 | 16.7 |
| 4F | 0.90 | 3.0 | 31.50 | 30.0 | 23.1 |
| 5F | 1.20 | 3.0 | 42.00 | 40.0 | 28.6 |
| 6F | 1.50 | 3.0 | 52.50 | 50.0 | 33.3 |
| 7F | 1.80 | 3.0 | 63.00 | 60.0 | 37.5 |

Examples 1G-20G

Using the same process as in Examples 1C-20C, 4 mixtures were prepared by mixing dcl with polymers 2A and 3A, polymers 2A and 4A, polymers 2A and 19A, and polymers 2A and 20A, respectively, using the amounts (in grams) shown in Table G1. Dry mixtures G1, G2 and G4 were uniform.

TABLE G1

| Example | dcl | 2A | 3A | 4A | 19A | 20A | IPA |
|---|---|---|---|---|---|---|---|
| 1G | 0.5 | 2.5 | 2.5 | | | | 17.5 |
| 2G | 0.5 | 2.5 | | 2.5 | | | 17.5 |
| 3G | 0.5 | 2.5 | | | 2.5 | | 17.5 |
| 4G | 0.5 | 2.5 | | | | 2.5 | 17.5 |

Examples 1H-20H

Table H1 summarizes the preparation and testing of 4 CYSC polymers 1H-4H. The polymers were prepared by the procedure described above, using the monomers, and the molar amounts thereof, shown in lines 1 of Table H1. The Mw, Mn and DSC characteristics of the polymers are shown in lines 2, 3 and 4 of Table H1.

Uniform mixtures of dcl with these polymers were prepared in the same manner as in Examples 1C-20C.

TABLE H1

| | | | Example No. | | | |
|---|---|---|---|---|---|---|
| | | | 1H 328-57-5 | 2H 328-57-8 | 3H 327-42-3 | 4H 327-42-12 |
| 1 | CYSC pol units (molar) | | | | | |
| | C18A | | | 0.3 | | |
| | C22A | | 1 | 0.7 | 1 | 4 |
| | AA | | 4 | 4 | 1 | 1 |
| | PEG6MA | | | | 1 | 1 |
| | HEMA | | | | 1 | 1 |
| | Acrylamide | | | | 1 | 1 |

TABLE H1-continued

| | | | Example No. | | | |
|---|---|---|---|---|---|---|
| | | | 1H 328-57-5 | 2H 328-57-8 | 3H 327-42-3 | 4H 327-42-12 |
| 2 | Mw | | 2976 | 12,645 | 711 | 4736 |
| 3 | Mn | | 2140 | 7136 | 440 | 3115 |
| 4 | DSC | $1^{st}$ heat Tp | 66.73 | 60.70 | 62.88 | 63.74 |
| | | $1^{st}$ heat To | 57.49 | 49.10 | 59.24 | 59.97 |
| | | $2^{nd}$ heat Tp | 63.40 | 57.18 | 61.59 | 61.20 |
| | | $2^{nd}$ heat To | 57.44 | 50.13 | 59.56 | 55.14 |

Line 14 (Examples 1I-20I) of Tables 1A, 1B and 1C summarizes the preparation of uniform mixtures of dcl and each of the 5 polymers (1A, 5A, 16A, 17A and 18A) which did not yield uniform mixtures in Examples 1C-20C (in which IPA was used). Uniform 2-phase mixtures were prepared by mixing dcl into the molten polymer at the weight ratio of 1/10 at 50-70° C. using a homogenizer for 1 min. in a vial. During the cooling stage, the vial continued to rotate until the mixture in the vial was solidified.

Line 15 (Examples 1J-20J) of Tables 1A, 1B and 1C summarizes the preparation of mixtures of risp and the polymers of Examples 1A-20A by mixing risp, polymer and IPA at the ratio of risp/polymer/IPA of 1/10/40 at 70° C., followed by removing IPA in a 70° C. oven. The dry mixture was obtained by removing residual IPA under the reduced pressure at 70° C. Only 5 out of the 20 mixtures were uniform. In the uniform mixtures, the polymers were 2A, 3A, 4A, 19A and 20A, all containing carboxylic acid moieties. Line 16 reports the DSC characteristics of the uniform mixtures.

Line 17 (Examples 1K-20K) of Tables 1A, 1B and 1C summarizes the preparation of mixtures of risp and the polymers of Examples 1A-20A. The mixtures contain 16.7% of risperidone and were prepared by mixing risperidone with each of 5 polymers (2A, 3A, 4A, 19A and 20A) in IPA at the ratio of risp/polymer/IPA=2/10/80 at 70° C., followed by removing IPA in a 70° C. oven. The final dry mixtures were obtained by removing residual IPA under reduced pressure at 70° C. Only polymer 3A yielded a uniform mixture at 16.7% loading. As summarized in Table K1 below, compositions containing polymer 3A and a wider range of risperidone loading were prepared using the same process as in Examples 1J-20J. All the resulting mixtures were uniform. When the loading was higher than 25%, the mixture was more viscous and a temperature higher than 70° C. was used to prepare the disk.

TABLE K1

| Example | Risperidone | Polymer | IPA | % drug on polymer | % drug in composition |
|---|---|---|---|---|---|
| 1K | 0.25 | 5 | 10 | 5.0 | 4.8 |
| 2K | 0.5 | 5 | 20 | 10.0 | 9.1 |
| 3K | 1 | 5 | 40 | 20.0 | 16.7 |
| 4K | 1.5 | 5 | 60 | 30.0 | 23.1 |
| 5K | 2 | 5 | 80 | 40.0 | 28.6 |
| 6K | 2.5 | 5 | 100 | 50.0 | 33.3 |
| 7K | 3 | 5 | 120 | 60.0 | 37.5 |

Examples 1L-4L

Using the same process as in Examples 1J-20J, 4 mixtures were prepared by mixing risp with polymers 2A and 3A, polymers 2A and 4A, polymers 2A and 19A, and polymers 2A and 20A, respectively, using the amounts (in grams)

shown in Table L1. Dry mixtures L1, L2 and L4 were uniform. The dry mixture L3 was not uniform.

TABLE L1

| Example | Risp | Polymer 2A | Polymer 3A | Polymer 4A | Polymer 19A | Polymer 20A | IPA |
|---------|------|------------|------------|------------|-------------|-------------|-----|
| 1L | 0.5 | 2.5 | 2.5 | | | | 20 |
| 2L | 0.5 | 2.5 | | 2.5 | | | 20. |
| 3L | 0.5 | 2.5 | | | 2.5 | | 20 |
| 4L | 0.5 | 2.5 | | | | 2.5 | 20 |

Examples 1M-20M

Uniform mixtures of risperidone at 9.1% loading with polymers 1H, 2H, 3H and 4H were prepared in the same manner as in Examples 1J-20J.

Line 18 (Examples 1N-20N) of Tables 1A, 1B and 1C summarizes the preparation of uniform two-phase mixtures of risp and each of four polymers (1A, 5A, 16A and 18A) by mixing risperidone powder (0.5 g) into the molten polymer (5 g) at 50-70° C. using a homogenizer for 1 min in a vial. During the cooling stage, the vial continued to rotate until the mixture in the vial was solidified. Since risperidone was not miscible with these 4 polymers, it became uniformly distributed in the CYSC polymer as a discrete phase.

Examples 1O-20O

Five mixtures (2J, 3J, 4J, 19J and 20J) from Example 1J-20J were subjected to a hand grinding process to generate powder, and then passed through a 450 micron filter screen. Mixture 19J was sticky and agglomerated. Test articles for the release of risperidone from these particles were prepared by confining 0.5 gram of powder in a wine-bottle-shaped wire mesh (200×200 wires per linear inch—an opening of about 75 micron). The resulting article was then placed in the bottom of a 20 ml vial, ready for a release test.

Examples 1P-20P

Uniform mixture 2J from Examples 1 J-20J was prepared as a thin flat disc in a 20 ml scintillation vial (28×61 mm=OD×H) by loading 0.05 gram of mixture at the bottom and warming in a 70° C. oven so that the mixture flowed and fused together, resulting in, after cooling, a very thin disc with a uniform flat surface. Such a thin disk was prepared to speed up the risperidone release as well as probe the effect of temperature triggering on release rate. Once the temperature triggering conditions were established, 0.5 g scale discs were prepared using the same methods in Examples 1J-20J and the dynamic temperature triggered release tests were performed using the conditions established in Examples P-20P.

Example 20Q

A uniform two-phase mixture was obtained by mixing Polymer 20A with Bovine serum albumin (BSA, Fraction V, 99% from Aldrich, 66,000 Daltons). The BSA was mixed into the molten polymer at 50-70° C. using a homogenizer for one minute in a vial. During the cooling stage, the vial continued to rotate until the mixture in the vial was solid. Since BSA was not miscible with polymer 20A at the molecular level, it became uniformly distributed in the CYSC polymer as discrete phase.

Example 20R

The procedure of Example 20Q was followed, but replacing the BSA by Leuprorelin powder, which, like BSA, was not miscible with the polymer at the molecular level and was uniformly distributed in the CYSC polymer as a discrete phase.

Lines 19 and 20 (Examples 1S-20S) of Tables 1A, 1B and 1C summarize the preparation of mixtures of pravastatin sodium (9.1%) and the polymers of Examples 1A-20A, using the same method as in Examples 1J-20J. There was no phase separation in any of the mixtures. The DSC characteristics of the mixtures are shown in line 20.

Lines 21 and 22 (Examples 1T-20T) of Tables 1A, 1B and 1C summarize the preparation of mixtures of dexamethasone (9.1%) and the polymers of Examples 1A-20A, using the same method as in Examples 1J-20J. Only the mixtures containing polymers 3A and 19A showed no phase separation in any of the mixtures. The DSC characteristics of those mixtures are shown in line 22.

Lines 23 and 24 (Examples 1T-20T) of Tables 1A, 1B and 1C summarize the preparation of mixtures containing dexamethasone (9.1%). Using the same method as in Examples 1N-20N, uniform two-phase mixtures were prepared by mixing each of polymers 2A, 4A, 7A, 10A, 17A, 18A and 20A with dexamethasone powder. The dexamethasone was added to the molten polymer at 50-70° C. at a wt ratio of 1/10 using a homogenizer for 1 min. in a vial. During the cooling stage, the vial continued to rotate until the mixture in the vial was solidified. Since dexamethasone was not miscible with these 7 polymers at the molecular level, it became uniformly distributed in the CYSC polymer as discrete phase. Line 24 shows the DSC characteristics of the mixtures.

Examples 2U, 3U, 4U and 20U

Polymers 2U, 3U, 4U and 20U contain the same ingredients as polymers 2A, 3A, 4A and 20A respectively and were prepared in the same manner except for additional post treatment to remove residual monomers. For polymers 2U and 4U, an additional 0.25% AIBN was used before IPA was removed, followed by 2 washes with methanol. For polymer 4U, additional 0.25% AIBN, 0.5% L575 and 0.5% T42S was used to reduce the residual monomer. For polymer 20U, an additional 0.25% AIBN was used before IPA was removed, followed by 2 washes with DI water. The Mw, Mn and the DSC characteristics of the polymers are in Table U1.

TABLE U1

| | | Average (Mw) | Average (Mn) | First Heat (° C.) | | Second Heat (° C.) | |
|---------|------------------|--------------|--------------|-------|-------|-------|-------|
| Example | CYSC Reference | | | Tp | To | Tp | To |
| 2U | 332-129 purified 2A | 3,481 | 3,093 | 45.82 | 43.34 | 42.67 | 33.99 |
| 3U | 332-137 purified 3A | 2,865 | 2,571 | 50.00 | 46.79 | 47.40 | 43.42 |
| 4U | 332-128 purified 4A | 5,503 | 4,583 | 47.26 | 43.53 | 43.70 | 36.50 |
| 20U | 332-130 purified 20A | 16,605 | 5,391 | 41.94 | 34.95 | 37.34 | 30.64 |

Examples 2V, 3V, 4V and 20V

Using the method described in Examples 1J-20J, polymers 2U, 3U, 4U and 20U were converted into cylindrical articles (diameter 6 mm, length 20 mm) containing 9.1% risperidone. The articles were sterilized by cobalt radiation at greater than 25 KGy.

Lines 25 and 26 (Examples 1W-20W) of Tables 1A, 1B and 1C summarize the preparation of mixtures of Tacrolimus (9.1%) and the polymers of Examples 1A-20A. The mixtures were prepared by mixing tacrolimus with the polymer in IPA at a ratio of 1/10/40 at 50-70° C., followed by removal of IPA in a 70° C. oven. The final dry mixture was obtained by removing residual IPA under reduced pressure at 70° C. All the dry mixtures were uniform. Line 26 shows the DSC characteristics of the dry mixtures.

Examples 21-40

Preparation of C12A Analogs of Polymers 1A-20A as Control

Using the same process as in examples 1A-20A, all the C12A analogs in Table Ex21-40 were prepared. All are amorphous polymers at room temperature. These polymers were used as controls against polymers 1A-20A to study the effect of side chain crystallinity on drug release rate.

TABLE EX21-40

Formulation of 20 copolymers from 14 classes of CYSC polymers

| Example ID | CYSC ID | Class ID | CYSC copolymer composition $M_1/M_2$ (molar ratio) |
|---|---|---|---|
| 21 | 328-133-2 | I | $C_{12}A$ (4/0) |
| 22 | 326-1-2 | II | $C_{12}A/AA$ (4/1) |
| 23 | 326-2-2 | II | $C_{12}A/AA$ (1/4) |
| 24 | 326-3-2 | III | $C_{12}A/AA/PEG_6$ (4/1/1) |
| 25 | 326-5-2 | IV | $C_{12}A/DMAEA$ (4/1) |
| 26 | 327-1-2 | V | $C_{12}A/DMAEMA/PEG_6$ (4/1/1) |
| 27 | 327-39-2 | VI | $C_{12}A/Cation$ (4/1) |
| 28 | 327-40-2 | VII | $C_{12}A/Cation/PEG_6$ (4/1/1) |
| 29 | 326-8-2 | VIII | $C_{12}A/PEG_9$ (4/1) |
| 30 | 326-8-4 | VIII | $C_{12}A/PEG_6$ (4/1) |
| 31 | 327-3-2 | VIII | $C_{12}A/PEG_{23}$ (4/1) |
| 32 | 327-3-4 | VIII | $C_{12}A/PEG_{46}$ (4/1) |
| 33 | 327-137-2 | VIII | $C_{12}A/PEG_{12}$ (4/1) |
| 34 | 327-137-4 | IX | $C_{12}A/PEG_{25}$-$C_{22}$ (4/1) |
| 35 | 326-6-2 | X | $C_{12}A/PEG_6$-OH (4/1) |
| 36 | 326-6-4 | XI | $C_{12}A/PPG_6$-OH (4/1) |
| 37 | 326-9-2 | XII | $C_{12}A/2$-HEA (4/1) |
| 38 | 326-11-4 | XIII | $C_{12}A/VP$ (4/1) |
| 39 | 327-42-1 | XIV | $C_{12}A$/acrylamide/AA/HEMA/PEG$_6$ methacrylate (1/1/1/1/1) |

TABLE EX21-40-continued

Formulation of 20 copolymers from 14 classes of CYSC polymers

| Example ID | CYSC ID | Class ID | CYSC copolymer composition $M_1/M_2$ (molar ratio) |
|---|---|---|---|
| 40 | 327-42-10 | XIV | $C_{12}A$/acrylamide/AA/HEMA/PEG$_6$ methacrylate (4/1/1/1/1) |

Examples 21A-40A

Preparation of Uniform Mixtures of C12A Polymer Analogs of Polymers 1A-20A with 9.1% Diclofenac Sodium Mixtures of drug and polymers 31 to 40 were prepared at 9.1% drug loading by mixing diclofenac sodium with polymers in isopropyl alcohol (IPA) at the ratio of diclofenac sodium/polymer/IPA=1/10/35 (wt/wt/wt) at 50-70° C., followed by evaporation of IPA in a 70° C. oven. The final dry drug/polymer mixtures were obtained by removing residual IPA under reduced pressure at 70° C. It was found that 8 out of the 20 mixtures of diclofenac sodium with polymers in examples 31-40 yielded uniform mixtures. Polymers that yielded uniform mixtures with diclofenac sodium were #22, #24, #26, #27 #28, #29, #33 and #35. It was observed that uniform drug/polymer mixtures remained amorphous.

Examples 41-51

Preparation of Uniform Mixtures of 11 Commercial Polymers as Controls with 9.1% Diclofenac Sodium

Including PLGA and Pluronic Polymer

Various commercially available polymers in Table Ex41-51a were purchased from Aldrich Chemical and used as controls against CYSC polymers related to controlled release of diclofenac sodium. All these polymers in examples 41 to 48 are water soluble. The polymers in examples 42 and 48 are PLGA polymers, which are main chain crystalline polymers. All the mixture in examples 41 to 48 were prepared in the same manner as in examples 1C-20C and the resulting dry mixtures were uniform. Risperidone is not miscible with both types of PLGA polymers (#42 and #48)

Pluronic F127, F68 and F38 were also acquired as controls against CYSC polymers related to controlled release of risperidone from BASF Corporation. These polymers are also main chain crystalline polymers with melting temperatures of 56° C., 54° C. and 49° C., respectively, based on $2^{nd}$ heating by DSC at 10° C./min. Mixtures in Table Ex41-51b were also prepared in the same manner as 1C-20C and were uniform. Diclofenac sodium is not miscible with all three polymers (#49, #50 and #51).

TABLE Ex41-51a

Preparation of uniform mixtures of commercial polymers at 9.1% diclofenac sodium loading

| Example ID | Polymer description | amount of polymer g | Diclofenac sodium g | IPA g |
|---|---|---|---|---|
| 41 | Polypropylene glycol, Mw = 3500 | 1 | 0.1 | 4 |
| 42 | Poly(DL-lactide-co-glycolide), 50:50, Tg = 26° C., Mw = 5k-15k | 1 | 0.1 | 4 |
| 43 | polyethylenimine, Mw = 25000 | 1 | 0.1 | 4 |
| 44 | Polyethylene glycol, Tm = 43-46° C., Mn = 1400 | 1 | 0.1 | 4 |
| 45 | Polyethylene glycol, Tm = 57-61° C., Mn = 4600 | 1 | 0.1 | 4 |
| 46 | Polycaprolactone Tm = 60° C., Mw = 14000 | 1 | 0.1 | 4 |

TABLE Ex41-51a-continued

Preparation of uniform mixtures of commercial polymers at 9.1% diclofenac sodium loading

| Example ID | Polymer description | amount of polymer g | Diclofenac sodium g | IPA g |
|---|---|---|---|---|
| 47 | poly(HEMA) Hydrogel, Mv = 20K | 1 | 0.1 | 4 |
| 48 | Poly(DL-lactide-co-glycolide), Tg = 45-50° C., 85% mole LA, Mw = 50K-75K | 1 | 0.1 | 4 |

TABLE Ex41-51b

Preparation of uniform mixtures of commercial polymers at 9.1% risperidone loading

| Example ID | Polymers | Amount of polymer g | Risperidone g | IPA g |
|---|---|---|---|---|
| 49 | Pluronic F127 | 2 | 0.2 | 7 |
| 50 | Pluronic F68 | 2 | 0.2 | 7 |
| 51 | Pluronic F38 | 2 | 0.2 | 7 |

Examples 52-67

Sustained/Controlled Release of Diclofenac from Examples 1C-20C

Typical release testing involving diclofenac sodium was conducted by covering the polymer/drug disc with 5 grams of buffer solution with pH=7.4, which was removed and replaced by 5 grams of fresh buffer solution at the scheduled sampling time at min, 2 hr, 6 hr, daily, weekly, or as necessary. The amount of diclofenac sodium released into the sample solution was measured by UV-Vis against a standard curve established by using the absorption signal at λ=276.93 nm.

All 15 uniform mixtures in examples 1A to 20A were subjected to release testing in phosphate buffer solution (50 mM ionic strength, pH 7.4 made isotonic with 150 mM NaCl and containing 0.01% w/v Tween-20). The following describes the procedure used to prepare the buffer solution. To 100 ml DI water was added 0.16 g of monosodium phosphate monohydrate and 1.04 g disodium phosphate, followed by NaCl and Tween-20 to final concentration of 0.9% and 0.01% w/v, respectively. The pH value was adjusted to 7.4 with 0.1N HCl or 0.1N NaOH as necessary.

Examples 52 to 67 represent the controlled release profiles of diclofenac sodium using the 15 uniform mixtures in examples 1C-20C and are labelled as 330-91-XX, where the numbers XX correspond to the numbers in examples 1C-20C. FIGS. C1, C2 and C3 show the cumulative release of diclofenac sodium in buffer solution with pH of 7.4.

Examples 68 to 75

Sustained/Controlled Release of Diclofenac from Examples 1D-20D

Examples 68 to 75 represent the controlled release profiles of diclofenac sodium using the 8 uniform mixtures in examples 1D-20D and are labelled as 330-108-XX, where the numbers XX correspond to the numbers in examples 1D-20D. FIG. D1 shows the cumulative release of diclofenac sodium.

Examples 76 to 81

Sustained/Controlled Release of Diclofenac from Examples 1E-20E

Examples 76 to 81 represent the controlled release profiles of diclofenac sodium using the 6 uniform mixtures in examples 1E-20E and are labelled as 330-109-XX, where the numbers XX correspond to the numbers in examples 1E-20E. FIG. E1 shows the cumulative release of diclofenac sodium. Sustained release is no longer exist in Examples 76-81 due to the addition of larger amount of NMP Examples 82-115

Sustained/Controlled Release of Diclofenac from Examples 1F-20F

Examples 82 to 115 represent the controlled release profiles of diclofenac sodium using all the uniform mixtures in examples 1F-20F and are labelled as 332-23-XX and 332-24-XX for 16.7% and 23.1% loading, where the numbers XX correspond to the polymer numbers in examples 1A-20A and 336-R4-Y, where the number Y correspond to the number in Tables F1. FIGS. F1, F2 and F3 show the cumulative release of diclofenac sodium at 16.7% loading. FIGS. F4 and F5 show the cumulative release of diclofenac sodium at 23.1% loading. FIG. F6 summarizes the release profile of up to 37.5% diclofenac sodium from polymer 2A. In FIG. F6, the release IDs 336-R4-1 to −336-R4-7 corresponds to 2F1 to 2F7 in Table F1.

Examples 116 to 118

Sustained/Controlled Release of Diclofenac from Examples G1-G4

Examples 116-118 represent the controlled release profiles of diclofenac sodium using the 3 uniform mixtures in examples G1-G4 and are labelled as 336-7-X, where the number X corresponds to the number in Table G1. FIG. G1 summarizes the release profile of diclofenac sodium from mixtures of 2A with 3A, 4A and 20A, as well as from single polymers 2A, 3A, 4A and 20A as comparison.

Examples 119-122

Sustained/Controlled Release of Diclofenac from Examples H1-H4

Examples 119-122 represent the controlled release profiles of diclofenac sodium using the 4 uniform mixtures of examples H1-H4 and are labelled as 336-8R8-X, where the number X corresponds to the numbers in Table H1. FIG. H1 summarizes the release profile of diclofenac sodium from polymers with higher Tm.

Examples 123-127

Sustained/Controlled Release of Diclofenac from Examples 1I-20I

Examples 123-127 represent the controlled release profiles of diclofenac sodium using the 5 uniform 2 phase mixtures in Tables 1A, 1B & 1C in examples 1I-20I and are labelled as 336-2R2-X, where the number X corresponds to the polymer numbers in Table A1. FIG. I1 summarizes the release profile of diclofenac sodium.

Examples 128-132

Sustained/Controlled Release of Risperidone from Examples 1J-20J

Typical release testing involving risperidone was conducted by covering the polymer/drug disc with 12.6 grams of buffer solution with pH=5.5, which was removed and replaced by 12.6 grams of fresh buffer solution at the scheduled sampling times at min, 2 hr, 6 hr, daily, weekly, or as necessary. The amount of risperidone released into the sample solution was measured by UV-V is against a standard curve established by using the absorption signal at $\lambda=276.93$ nm.

All 5 uniform mixtures in examples 1J to 20J were subjected to release testing in phosphate buffer solution (50 mM ionic strength, pH 5.5 made isotonic with 150 mM NaCl and containing 0.01% w/v Tween-20). The following describes the procedure used to prepare the buffer solution. To 100 ml DI water was added 0.16 g of monosodium phosphate monohydrate and 1.04 g disodium phosphate, followed by NaCl and Tween-20 to final concentration of 0.9% and 0.01% w/v, respectively. The pH was adjusted to 5.5 with 0.1N HCl as necessary.

Examples 128 to 132 represent the controlled release profiles of risperidone using the 5 uniform mixtures in examples 1J-20J and are labelled as 330-117-XX, where the numbers XX correspond to the numbers in Tables 1A, 1B &1C. FIG. J1 shows the release profile of risperidone from the mixtures of 9.1% risperidone in 5 polymers.

Examples 133-139

Sustained/Controlled Release of Risperidone from Examples 1K-20K

Examples 133 to 139 represent the controlled release profiles of risperidone using all the 7 uniform mixtures in examples 1K-20K and are labelled as 336-5-X, where the number X corresponds to the numbers 3K1 to 3K7 in Table K1. FIG. K1 shows the cumulative release of up to 37.5% risperidone from polymer 3A.

Examples 140-142

Sustained/Controlled Release of Risperidone from Examples L1-L4

Examples 140-142 represent the controlled release profiles of risperidone using the 3 uniform mixtures in examples 1L-20L and are labelled as 336-R6-X, where the number X corresponds to the numbers L1 to L4 in Table L1. FIG. L1 summarizes the release profile of risperidone from mixtures of 2A with 3A, 4A and 20A, as well as from single polymers 2A, 3A, 4A and 20A as comparison.

Examples 143-146

Sustained/Controlled Release of Risperidone from Examples 1M-20M

Examples 143-146 represent the controlled release profiles of risperidone using the 4 uniform mixtures H1 to H4 in Table H1 in examples 1M-20M and are labelled as 336-R9-X, where the number X corresponds to the polymer numbers H1 to H4 in Table H1. FIG. M1 summarizes the release profile of risperidone from polymers with higher Tm.

Examples 147-150

Sustained/Controlled Release of Risperidone from Examples 1N-20N

Examples 147-150 represent the controlled release profiles of risperidone using the 4 uniform 2 phase mixtures in examples 1N-20N and are labelled as 336-3R3-X, where the number X corresponds to the numbers in Tables 1A, 1B &1C. FIG. N1 summarizes the release profile of risperidone from the 4 polymers.

Examples 151-154

Sustained/Controlled Release of Risperidone from Examples 1O-20O

Examples 151-154 represent the controlled release profiles of risperidone from polymers 2A, 3A, 4A and 20A in powder form in examples 1O-20O and are labelled as 335-31-XX, where the number XX corresponds to the number for the polymer IDs in Tables 1A, 1B & 1C. FIG. O1 summarizes the release profile of risperidone from the 4 polymers.

Examples 155-156

Static Temperature Triggered Release of Risperidone from Polymer 2A from Examples 1P-20P Examples 155 to 156 represent the controlled release profiles of risperidone from polymer 2A in examples 1P-20P as 0.05 gram scale thin discs at 37° C. and 60° C. The release IDs are labelled as 330-135-2 and 332-3-2 at 37° C. and 60° C., respectively. FIG. P1 summarizes the release profile of risperidone from polymer 2A as 0.05 gram scale thin disc at 37° C. and 60° C.

Examples 157-163

Dynamic Temperature Triggered Release of Risperidone from Polymer 2A from Examples 1P-20P Examples 157 and 163 represent the controlled release profiles of risperidone from polymer 2A in examples 1P-20P as 0.5 gram scale thicker discs than examples 155-156 at 37° C. and 60° C. bath at selected times and/or days.

FIG. P2 summarizes one version of the temperature triggered release profiles of risperidone from polymer 2A by exposing the 0.5 gram thick discs in buffer solution at pH of 5.5 to 60° C. bath daily for 0, 5, 15, 30 and 60 min (0=temperature switch OFF, 5, 15, 30 and 60 min=temperature switch ON for 5, 15, 30 and 30 min, respectively) and the remaining of time at 37° C. The release IDs were labelled as 332-27-XX.

FIG. P3 summarizes the another version of the temperature triggered release profiles of risperidone from polymer 2A by exposing the 0.5 gram thick discs in buffer solution at pH of 5.5 to 60° C. bath every other day for 0 (for temperature switch OFF position) and 60 min (for temperature switch ON position) and the remaining of time at 37° C. The release ID was labelled as 332-45-1,2,3.

FIG. P4 summarizes the 3rd version of the temperature triggered release profiles of risperidone from polymer 2A by exposing the 0.5 gram thick discs in buffer solution at pH of 5.5 to 60° C. bath every other 2 days for 0 (for temperature switch OFF position) and 60 min (for temperature switch ON position) and the remaining of time at 37° C. The release ID was labeled as 332-45-4,5,6.

Examples 164-166

Static pH Triggered Release of BSA from Examples 20Q

Examples 164-166 represent the controlled release profiles of BSA from polymer 20A (example 20Q in examples 1Q-20Q) in buffer solutions with pH=7.4, 5.5 and 2.5 at 37° C. FIG. Q1 summarizes static pH triggered release profiles of BSA from polymer 20A in these buffer solutions at 37° C. The release IDs are labelled as 334-19-20, 334-20-20 and 334-21-20 for release in pH 7.4, 5.5 and 2.5 buffer solution, respectively.

Examples 167

Dynamic pH Triggered Release of BSA from Examples 20Q

Example 167 represents the controlled release profile of BSA from polymer 20A (example 20Q in examples 1Q-20Q) in buffer solution with pH=2.5 for initial 3 hours and the remaining of time with pH=7.4 buffer solution at 37° C. FIG. Q2 summarizes the dynamic pH triggered release profile of BSA from polymer 20A in dynamic pH buffer solutions at 37° C. The release IDs were labelled as 334-52-20.

Examples 168-173

Static and Dynamic pH Triggered Release of Leuprorelin from Examples 20R

Examples 168-173 represent the controlled release profiles of Leuprorelin from polymer 20A in buffer solutions with pH=2.5 and 7.4 buffer solutions at 37° C. for static pH triggered release and with combination of pH=2.5 and 7.5 (initial 3 hours with pH=2.5 and the remaining of time with pH=7.4) for dynamic pH triggered release. FIG. R1 summarizes both static and dynamic pH triggered release profile of Leuprorelin from polymer 20A at 37° C.

Examples 174-179

Sustained/Controlled Release of Pravastatin Sodium from Examples 1S-20S

Examples 174 to 179 represent the controlled release profiles of pravastatin sodium from selected polymers 1A, 2A, 3A, 4A, 19A and 20A in buffer solutions with pH=7.4 at 37° C. FIG. S1 summarizes the release profile of pravastatin from example 1R, 2R, 3R, 4R, 19R and 20R in buffer solution with pH=7.4 at 37° C. The release IDs were labelled as 336-1-X, where the numbers X corresponds to the examples IDs in Tables 1A, 1B &1C. The release and sampling conditions are the same as in examples 1C-20C. The amount of pravastatin sodium released into the sample solution was measured by UV-Vis against a standard curve established by using the absorption signal at $\lambda$=238.5 nm.

Examples 180-181

Sustained/Controlled Release of Dexamethasone from examples 1T-20T

Examples 180 to 181 represent the controlled release profiles of dexamethasone from polymers 3A and 19A in buffer solutions with pH=7.4 at 37° C. FIG. T1 summarizes the release profile of pravastatin from polymer 3A and 19A in buffer solution with pH=7.4 in 37° C. bath. The release IDs are labelled as 336-35-XX, where the numbers XX correspond to examples IDs in Tables 1A, 1B &1C. The release and sampling conditions are the same as in examples 1C-20C. The amount of dexamethasone released into the sample solution was measured by UV-Vis against a standard curve established by using the absorption signal at $\lambda$=242 nm.

Examples 182-188

Sustained/Controlled Release of Dexamethasone from Examples 1T-20T

Uniform 2 Phase Mixture

Examples 182 to 188 represent the controlled release profiles of dexamethasone from polymers 2A, 4A, 7A, 10A, 17A, 18A and 20A in buffer solutions with pH=7.4 at 37° C. FIG. T2 summarizes the release profile of pravastatin from polymers 2A, 4A, 7A, 10A, 17A, 18A and 20A in buffer solution with pH=7.4 at 37° C. The release IDs are labelled as 336-35-XX, where the numbers XX correspond to examples IDs in Tables 1A, 1B &1C. The release and sampling conditions are the same as in examples 1C-20C. The amount of dexamethasone released into the sample solution was measured by UV-Vis against a standard curve established by using the absorption signal at $\lambda$=242 nm.

Examples 189-196

Sustained/Controlled Release of Diclofenac from Examples 21A-40A

C12A Analogs of Polymers 1A-20A as Control

Examples 189 to 196 represent the controlled release profiles of diclofenac sodium using the 8 uniform mixtures in examples 21A-40A and are labelled as 332-7-XX, where the numbers XX correspond to polymers IDs in Table Ex21-40. FIG. Ex21A-40A shows the cumulative release of diclofenac sodium in example 21A-40A.

Examples 197-207

Sustained/Controlled Release of Diclofenac Sodium and Risperidone from Examples 41-51

Commercial Polymers as Control

Examples 197-204 represent the controlled release profiles of diclofenac sodium using the 4 uniform mixtures in examples 41-51 and are labelled as 332-4-XX, where the numbers XX correspond to polymers IDs shown in FIG. Ex41-51a. FIG. Ex41-51a shows the cumulative release of diclofenac sodium in buffer solution with pH of 7.4. Typical release testing was conducted by covering the polymer/drug disc with 5 grams of buffer solution, which was removed and replaced by 5 grams of fresh buffer solution at the scheduled sampling times at 1 min, 2 hr, 6 hr, daily, weekly, or as necessary. The amount of diclofenac sodium released into the sample solution was measured by UV-Vis against a standard curve established by using the absorption signal at $\lambda=276.93$ nm.

Examples 205-207 represent the controlled release profiles of risperidone using the 3 uniform mixtures in examples 41-51 and are labelled as 332-75-X, where the number X corresponds to polymers IDs shown in FIG. Ex41-51b. FIG. Ex41-51b shows the cumulative release of risperidone in buffer solution with pH of 5.5. Typical release testing was conducted by covering the polymer/drug disc with 12.6 grams of buffer solution, which was removed and replaced by 12.6 grams of fresh buffer solution at the scheduled sampling times at 1 min, 2 hr, 6 hr, daily, weekly, or as necessary. The amount of risperidone released into the sample solution was measured by UV-Vis against a standard curve established by using the absorption signal at $\lambda=276.93$ nm.

Examples 208-212

In-Vivo Sustained/Controlled Release of Risperidone from Examples 1Y-20Y

Examples 206-210 represent the in-vivo release profiles of risperidone, and are shown in FIGS. Y1 to Y5. FIG. Y1 shows the in-vivo Control release profile. FIGS. Y2 to Y5 show the risperidone in-vivo release from each of the identified polymers.

Example 213

Preclinical Evaluation of Risperidone-Loaded Intelimer Polymers

Method: The sustained release properties of the polymers of the invention were evaluated in a healthy Sprague-Dawley rat subcutaneous (SC) implantation model. Implants were prepared as described below and were loaded with risperidone. Briefly, four different types of implants were prepared and evaluated: Group #2 (336-19-2), Group #4 (336-19-3), Group #3 (336-19-4), and Group #20 (336-19-20). In addition, implants devoid of the drug substance were prepared and evaluated as well: Group #6 (336-20-2) and Group #7 (336-20-20). A total of 10 replicates of each implant test article were provided, four of which were randomly selected for single implantation per animal. All systems were stored at room temperature before and after completion of the implantation.

An aqueous solution of risperidone was used as the Control Article. The risperidone solution was prepared at a drug concentration of 0.27 mg/mL in phosphate buffer pH 5.5 containing 0.01% w/v Tween-80, filtered through 0.45 micron polycarbonate membrane. The solution was injected SC at 0.2 mg/kg without additional dilutions.

Seven groups (N=6 for group 1 and N=4 for other 6 groups) of only male jugular vein cannulated (JVC) Sprague Dawley rats, weighing approximately 300 g at study initiation (Hilltop Lab Animals, Scottdale, Pa.) were defined. Surgical implantation of Landec's devices were performed on rats under light anesthesia. The implants were briefly rinsed with a PBS solution pH 7.4 with a single rinse and were inserted SC space of the rats.

TABLE 1

Experimental Design

| Group # | Test Article | Route | N | Type and volume | Blood Collection Timepoints |
|---|---|---|---|---|---|
| 1 | Control | IV | 6 | Solution, 0.75 µL | Predose, 5, 15, 30 min, 1, 2, 4, 6, 8 hrs |
| 2 | Implant #2: 336-19-2 | SQ implant | 4 | Drug-eluting implant | Predose, 15, 30, 60 min, 2, 4, 8 hrs, 1, 2, 4, |
| 3 | Implant #4: 336-19-4 | | 4 | | 7, 11, 14, 17, 21, 24 |
| 4 | Implant #3: 336-19-3 | | 4 | device | and 28 days |
| 5 | Implant #20: 336-19-20 | | 4 | | |
| 6 | Implant Control #2: 336-20-2 | | 4 | | |
| 7 | Implant Control #20: 336-20-20 | | 4 | | |

Blood (0.3 mL) samples were collected at specified time intervals as described in the Table above and were placed into labeled MICROTAINER tubes with EDTA as an anti-coagulant. The heparin blood samples were centrifuged, transferred into labeled Eppendorf tubes and frozen at −80° C. and were assayed by a validated LC-MS assay for riperidone and 9-hydroxy-risperidone. At the end of the study the animals were euthanized according to testing facility Standard Operating Procedures, followed by terminal bleeds via cardiocentesis. Device-implanted rats underwent gross necropsy while the tissue was scored macroscopically for irritation, erythema, edema using an established scale.

Results: The results shown in the graphs below represent total risperidone in plasma, including both the parent compound and the active metabolite (9-hydroxy-risperidone).

The invention claimed is:

1. A pharmaceutical formulation which (a) comprises (i) a side-chain crystalline (CYSC) polymer which has a polymer backbone and (ii) a single drug, the drug being associated with the CYSC polymer, (b) is free from oil, and (c) is in a dosage form which can be administered by ingestion, injection, subcutaneous implantation, intramuscular administration, intrathecal administration or inhalation, wherein the CYSC polymer, (A) comprises a plurality of moieties which
  (a) have the formula -b-Cy and (b) are present (i) as a part of a repeating unit which provides at least part of the polymeric backbone of the polymer, or (ii) as part of a terminal unit of the polymer backbone, or (iii) as both (i) and (ii), the repeating units having formula (1) below,

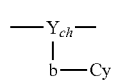 (1)

and the terminal units having formula (2) below

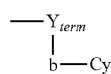 (2)

where
- in formula (1), $Y_{ch}$ is a moiety forming part of the backbone of the CYSC polymer,
- in formula (2), $Y_{term}$ is a moiety at the end of the backbone of the CYSC polymer,
- and in formula (1) and in formula (2), b is a bond or a moiety which (i) links the Cy moiety to the polymer backbone and (ii) is not an anhydride linkage, and
- Cy is a moiety which (i) comprises 6 to 50 substantially linear carbon atoms, and (ii) associates with other moieties to provide the CYSC polymer with crystallinity;

(B) comprises a plurality of repeating units of the formula

where Z is a moiety which forms part of the polymer backbone, and Rz is a moiety which (i) is not a -b-Cy moiety, and (ii) is a nitrogen-containing side chain, an oxygen-containing side chain, a fluorine-containing side chain, a phosphorus-containing side chain, a silicon-containing side chain or a ligand group which binds to target receptor sites; the percentage by weight of the repeating units of formula

being less than 50%;

(C) has a crystalline melting temperature, Tp, of 22 to 70° C., and an onset of melting point, To, such that (Tp–To) is less than 15° C.;

(D) has a heat of fusion of least 5 J/g which results from the association of the Cy moieties;

(E) is not cross-linked, and (F) has a number average molecular weight, Mn, of 1000 to 20,000 Daltons.

2. A pharmaceutical formulation according to claim 1 wherein at least some of the Cy moieties are present in repeating units having the formula

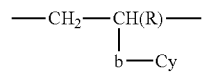

where R is hydrogen or methyl.

3. A pharmaceutical formulation according to claim 2 wherein b is a moiety having the formula

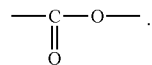

4. A pharmaceutical formulation according to claim 1 wherein at least some of the Cy moieties comprise 12 to 50 substantially linear carbon atoms.

5. A pharmaceutical formulation according to claim 1 wherein at least some of the Cy moieties comprise 18 linear carbon atoms.

6. A pharmaceutical formulation according to claim 1 wherein the repeating units of the formula

have the formula

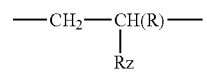

where R is hydrogen or methyl.

7. A pharmaceutical formulation according to claim 1 wherein the drug is a neurotransmitter agonist or antagonist.

8. A pharmaceutical formulation according to claim 1 wherein the drug is an antipsychotic.

9. A pharmaceutical formulation according to claim 1 wherein the drug is RISPERIDONE or a pharmacologically active metabolite thereof.

10. A pharmaceutical formulation according to claim 1 wherein the CYSC polymer is a copolymer comprising units derived from octadecyl acrylate (C18A) and acrylic acid (AA), and the drug is a neurotransmitter agonist or antagonist.

11. A pharmaceutical formulation according to claim 10 wherein the drug is RISPERIDONE.

12. A pharmaceutical formulation according to claim 1 wherein the CYSC polymer is a polyacrylate or polymethacrylate.

13. A pharmaceutical formulation according to claim 1 wherein the CYSC polymer is a polyester or a polycarbonate.

14. A pharmaceutical formulation according to claim 1 wherein the CYSC polymer has a number average molecular weight less than 10,000 Daltons.

15. A pharmaceutical formulation according to claim 1 wherein the CYSC polymer is a block copolymer.

16. A pharmaceutical formulation according to claim 1 which contains a first CYSC polymer having a first melting point Tp1 and a second CYSC polymer having a second melting point Tp2 which is at least 2° C. different from Tp1.

17. A pharmaceutical formulation according to claim 1
(A) which contains a compound which (i) contains Cy moieties, and (ii) is not a CYSC polymer, and
(B) in which the Cy moieties in the CYSC polymer and the Cy moieties in the compound which is not a CYSC polymer together form crystalline aggregates.

18. A pharmaceutical formulation according to claim 1 wherein at least some of the Cy moieties are present in the terminal units and comprise 12-50 substantially linear carbon atoms.

19. A pharmaceutical formulation according to claim 1 wherein at least some of the Cy moieties are present in the terminal units and comprise 18-22 substantially linear carbon atoms.

20. A pharmaceutical formulation according to claim 1 wherein at least some of the Cy moieties are present in the terminal units and comprise 18 substantially linear carbon atoms.

21. A pharmaceutical formulation according to claim 1 wherein at least some of the Cy moieties contain a polyoxyalkylene moiety.

22. A pharmaceutical formulation according to claim 1 wherein at least some of the Rz moieties contain a carboxyl group, or a hydroxyl group.

23. A pharmaceutical formulation according to claim 1 wherein the CYSC polymer is a graft copolymer which comprises a backbone which comprises one or more —Z(Rz)- moieties, and grafted side chains each of which comprises one or more —Y(Rc)- moieties.

24. A pharmaceutical formulation according to claim 1 wherein the drug is associated with the CYSC polymer through chemical bonds.

25. A pharmaceutical formulation according to claim 1 wherein the drug is an antipsychotic drug.

26. A pharmaceutical formulation according to claim 1 wherein the drug is RISPERIDONE or a pharmacologically active metabolite thereof.

27. A pharmaceutical formulation according to claim 1 which contains at least 5% by weight of the drug and which, when tested in vitro (elution into 1 L PBS, pH 7.2 at 37° C., stirred at 100 rpm), releases the drug in a way which has one or more of the following characteristics:
   (a) an average rate of release no greater than 50 milligrams per day averaged over any 24 hour period during the first 168 hours of elution;
   (b) an average rate no greater than 25 milligrams per day averaged over any 24 hour period during a period from 12 hours to 168 hours following inception of elution;
   (c) continuously releases between 1 milligram and 60 milligram of the drug per day over a period of at least 30 days;
   (d) continuously releases between 1 milligram and 60 milligrams of the drug per day averaged over any 24 hour period during a period from 12 hours to 168 hours following inception of elution;
   (e) releases no more than 10% by weight of the drug present in the formulation over a period of 24 hours; and,
   (f) continuously releases a therapeutic dose of drug over a period of at least 30 days wherein the average 24 hour drug release rate is within one standard deviation of the 30 day mean.

28. A pharmaceutical formulation which (a) is in a dosage form which can be administered by ingestion, injection, subcutaneous implantation, intramuscular administration, intrathecal administration or inhalation, and (b) comprises (i) a side-chain crystalline (CYSC) polymer which has a polymer backbone and (ii) a single drug which is associated with the CYSC polymer, wherein the CYSC polymer,
   (A) comprises a plurality of moieties which
      (a) have the formula -b-Cy and
      (b) are present (i) as a part of a repeating unit which provides at least part of the polymeric backbone of the polymer, or (ii) as part of a terminal unit of the polymer backbone, or (iii) as both (i) and (ii), the repeating units having formula (1) below,

and the terminal units having formula (2) below

where
      in formula (1), $Y_{ch}$ is a moiety forming part of the backbone of the CYSC polymer,
      in formula (2), $Y_{term}$ is a moiety at the end of the backbone of the CYSC polymer,
      and in formula (1) and in formula (2), b is a bond or a moiety which (i) links the Cy moiety to the polymer backbone and (ii) is not an anhydride linkage, and
      Cy is a moiety which (i) comprises 6 to 50 substantially linear carbon atoms, and (ii) associates with other moieties to provide the CYSC polymer with crystallinity;
      the polymer backbone consisting essentially of repeating units having the formula (1)
   (B) has a crystalline melting temperature, Tp, of 22 to 70° C., and an onset of melting point, To, such that (Tp−To) is less than 15° C.;
   (C) has a heat of fusion of least 5 J/g which results from the association of the Cy moieties; and
   (D) is not cross-linked.

29. A pharmaceutical formulation according to claim 28 wherein the CYSC polymer has a number average molecular weight, Mn, of 1,000 to 20,000 Daltons.

30. A pharmaceutical formulation according to claim 28 wherein the CYSC polymer has a number average molecular weight, Mn, of less than 10,000 Daltons.

31. A pharmaceutical formulation according to claim 28 wherein the CYSC polymer is a polyacrylate or polymethacrylate.

32. A pharmaceutical formulation according to claim 28 wherein the CYSC polymer is a polyester.

33. A pharmaceutical formulation according to claim 28 wherein the CYSC polymer is a polycarbonate.

34. A pharmaceutical formulation according to claim 1 wherein the CYSC polymer is a block copolymer.

35. A pharmaceutical formulation according to claim 1 which contains a first CYSC polymer having a first melting point Tp1 and a second CYSC polymer having a second melting point Tp2 which is at least 2° C. different from Tp1.

36. A pharmaceutical formulation according to claim 26
   (A) which contains a compound which (i) contains Cy moieties, and (ii) is not a CYSC polymer, and
   (B) in which the Cy moieties in the CYSC polymer and the Cy moieties in the compound which is not a CYSC polymer together form crystalline aggregates.

37. A pharmaceutical formulation according to claim 1 wherein at least some of the Cy moieties comprise 12-50 substantially linear carbon atoms.

38. A pharmaceutical formulation according to claim 1 wherein at least some of the Cy moieties comprise 18-22 substantially linear carbon atoms.

39. A pharmaceutical formulation according to claim 1 for use in therapy or diagnosis.

40. A method of making a pharmaceutical formulation as claimed in claim 1 which comprises melting the CYSC polymer, mixing the drug with the molten polymer in the absence of solvents, and cooling the mixture to below its melting point to cause crystallization and solidification of the formulation.

41. A pharmaceutical formulation according to claim 1 which is in a dosage form selected from liquids, tablets, pills and capsules.

42. A pharmaceutical formulation according to claim 28 which is in a dosage form selected from liquids, tablets, pills and capsules.

43. A pharmaceutical formulation according to claim 1 wherein the percentage by weight of the repeating units of the formula

is 5-25%.

44. A pharmaceutical formulation according to claim 1 wherein the percentage by weight of the repeating units of the formula

is less than 23%.

45. A pharmaceutical formulation according to claim 1 wherein, in each of the repeating units of formula (1), b is not an amide linkage, and the percentage by weight of the repeating units of the formula

is 5-25%.

46. A pharmaceutical formulation according to claim 1 wherein, in each of the repeating units of formula (1), the b moiety is selected from the group consisting of ester, carbonyl, amine oxide, hydrocarbon, amino, ether, polyoxyalkylene and ionic salt linkages, and the percentage by weight of the repeating units of the formula

is 5-25%.

47. A pharmaceutical formulation according to claim 1 wherein, in each of the repeating units of formula (1), the b moiety is an ester linkage, and the percentage by weight of the repeating units of the formula

is 5-25%.

48. A pharmaceutical formulation according to claim 1 wherein, in each of the repeating units of formula (1), the b moiety is a moiety selected from one or more of carbonyl, amine oxide, amino, polyoxyalkylene and ionic salt linkages.

49. A pharmaceutical formulation according to claim 1 wherein in each of the repeating units of the formula

Rz is a moiety selected from one or more of a nitrogen-containing side chain, a fluorine-containing side chain, a phosphorus-containing side chain, a silicone-containing side chain and a ligand group which binds to target receptor sites.

50. A pharmaceutical formulation which
(a) comprises (i) a side-chain crystalline (CYSC) polymer which has a polymer backbone, (ii) hyaluronic acid, and (ii), in addition to the hyaluronic acid, a single other drug which is associated with the CYSC polymer,
(b) is free from oil, and
(c) is in a dosage form which can be administered by ingestion, injection, subcutaneous implantation, intramuscular administration, intrathecal administration or inhalation,
wherein the CYSC polymer,
(A) comprises a plurality of moieties which
(a) have the formula -b-Cy and
(b) are present (i) as a part of a repeating unit which provides at least part of the polymeric backbone of the polymer, or (ii) as part of a terminal unit of the polymer backbone, or (iii) as both (i) and (ii), the repeating units having formula (1) below,

 (1)

and the terminal units having formula (2) below

 (2)

where
in formula (1), $Y_{ch}$ is a moiety forming part of the backbone of the CYSC polymer,
in formula (2), $Y_{term}$ is a moiety at the end of the backbone of the CYSC polymer,
and in formula (1) and in formula (2), b is a bond or a moiety which (i) links the Cy moiety to the polymer backbone and (ii) is not an anhydride linkage, and
Cy is a moiety which (i) comprises 6 to 50 substantially linear carbon atoms, and (ii) associates with other moieties to provide the CYSC polymer with crystallinity;
(B) comprises a plurality of repeating units of the formula

where Z is a moiety which forms part of the polymer backbone, and Rz is a moiety which (i) is not a -b-Cy moiety, and (ii) is a nitrogen-containing side chain, an oxygen-containing side chain, a fluorine-containing side chain, a phosphorus-containing side chain, a silicon-containing side chain or a ligand group which binds to target receptor sites; the percentage by weight of the repeating units of formula

being less than 50%;

(C) has a crystalline melting temperature, Tp, of 22 to 70° C., and an onset of melting point, To, such that (Tp−To) is less than 15° C.;

(D) has a heat of fusion of least 5 J/g which results from the association of the Cy moieties;

(E) is not cross-linked, and (F) has a number average molecular weight, Mn, of 1000 to 20,000 Daltons.

51. A pharmaceutical formulation according to claim 50 wherein the percentage by weight of the repeating units of the formula

is 5-25%.

52. A pharmaceutical formulation according to claim 50 wherein the percentage by weight of the repeating units of the formula

is less than 23%.

53. A pharmaceutical formulation according to claim 50 wherein, in each of the repeating units of formula (1), b is not an amide linkage, and the percentage by weight of the repeating units of the formula

is 5-25%.

54. A pharmaceutical formulation according to claim 50 wherein, in each of the repeating units of formula (1), the b moiety is selected from the group consisting of ester, carbonyl, amine oxide, hydrocarbon, amino, ether, polyoxyalkylene and ionic salt linkages, and the percentage by weight of the repeating units of the formula

is 5-25%.

55. A pharmaceutical formulation according to claim 50 wherein, in each of the repeating units of formula (1), the b moiety is an ester linkage, and the percentage by weight of the repeating units of the formula

is 5-25%.

56. A pharmaceutical formulation according to claim 50 wherein, in each of the repeating units of formula (1), the b moiety is a moiety selected from one or more of carbonyl, amine oxide, amino, polyoxyalkylene and ionic salt linkages.

57. A pharmaceutical formulation according to claim 50 wherein, in each of the repeating units of the formula $$-\underset{Rz}{Z}-$$

Rz is a moiety selected from one or more of a nitrogen-containing side chain, a fluorine-containing side chain, a phosphorus-containing side chain, a silicone-containing side chain and a ligand group which binds to target receptor sites.

58. A pharmaceutical formulation according to claim 28 which contains, in addition to the single drug, hyaluronic acid.

* * * * *